United States Patent
Blaesi et al.

(10) Patent No.: US 12,251,465 B2
(45) Date of Patent: Mar. 18, 2025

(54) DOSAGE FORM COMPRISING STRUCTURED SOLID-SOLUTION FRAMEWORK OF SPARINGLY-SOLUBLE DRUG AND METHOD FOR MANUFACTURE THEREOF

(71) Applicant: Aron H. Blaesi, Cambridge, MA (US)

(72) Inventors: Aron H. Blaesi, Cambridge, MA (US); Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 528 days.

(21) Appl. No.: 17/207,587

(22) Filed: Mar. 19, 2021

(65) Prior Publication Data

US 2021/0212943 A1  Jul. 15, 2021

Related U.S. Application Data

(63) Continuation of application No. PCT/US2019/052030, filed on Sep. 19, 2019.
(Continued)

(51) Int. Cl.
| | |
|---|---|
| *A61K 9/00* | (2006.01) |
| *A61K 9/107* | (2006.01) |
| *A61K 9/70* | (2006.01) |
| *A61K 31/192* | (2006.01) |
| *A61K 47/34* | (2017.01) |
| *A61K 47/38* | (2006.01) |
| *B29C 48/00* | (2019.01) |
| *B29K 105/00* | (2006.01) |

(52) U.S. Cl.
CPC ............ *A61K 9/0092* (2013.01); *A61K 9/107* (2013.01); *A61K 9/7007* (2013.01); *A61K 31/192* (2013.01); *A61K 47/34* (2013.01); *A61K 47/38* (2013.01); *B29C 48/001* (2019.02); *B29C 48/022* (2019.02); *B29K 2105/0035* (2013.01)

(58) Field of Classification Search
None
See application file for complete search history.

(56) References Cited

U.S. PATENT DOCUMENTS 7,491,407 B2 * 2/2009 Pourdeyhimi ........... A61K 9/70
424/443

FOREIGN PATENT DOCUMENTS

WO    WO-2017075096 A1 * 5/2017 ........... A61K 31/167

OTHER PUBLICATIONS

Moulton et al. (3-dimensional (3D) fabricated polymer based drug delivery system, Journal of Controlled Release, vol. 193, Nov. 10, 2014, pp. 27-34) (Year: 2014).*

* cited by examiner

*Primary Examiner* — Melissa S Mercier

(57) ABSTRACT

By the ingestion of dosage forms containing sparingly water-soluble drug particles, it is not possible to deliver drug into the blood stream at high rates, because the drug dissolution rate, and the absorption rate, are limited by solubility. Herein, therefore, dosage forms comprising a slender, three-dimensional structural framework of sparingly-soluble drug dissolved in an excipient matrix comprising at least a water-soluble polymer carrier and an amphiphilic polymer are disclosed. Upon immersion in a physiological fluid, said fluid wets the structural framework, interdiffuses with it, and the amphiphilic polymer self-assembles as micelles, thereby enhancing drug solubility. Concomitantly, the framework erodes and rapidly releases drug molecules, thus enhancing drug concentration in the fluid and the drug delivery rate into the blood stream.

34 Claims, 37 Drawing Sheets

Related U.S. Application Data

(60) Provisional application No. 62/733,624, filed on Sep. 19, 2018, provisional application No. 62/856,073, filed on Jun. 2, 2019, provisional application No. 62/893,178, filed on Aug. 28, 2019.

DOSAGE FORM COMPRISING STRUCTURED SOLID-SOLUTION FRAMEWORK OF SPARINGLY-SOLUBLE DRUG AND METHOD FOR MANUFACTURE THEREOF

CROSS-REFERENCE TO RELATED INVENTIONS

This application is a continuation of, and incorporates herein by reference in its entirety, the International Application No. PCT/US19/52030 filed on Sep. 19, 2019 and titled "Dosage form comprising structured solid-solution framework of sparingly-soluble drug and method for manufacture thereof", which claims priority to and the benefit of, the U.S. Provisional Application Nos. 62/733,624 filed on Sep. 19, 2018, 62/856,073 filed on Jun. 2, 2019, and 62/893,178 filed on Aug. 28, 2019. All foregoing applications are incorporated herein by reference in their entirety.

This application is related to, and incorporates herein by reference in their entirety, the U.S. application Ser. No. 15/482,776 filed on Apr. 9, 2017 and titled "Fibrous dosage form", the U.S. application Ser. No. 15/964,058 filed on Apr. 26, 2018 and titled "Method and apparatus for the manufacture of fibrous dosage forms", the U.S. application Ser. No. 15/964,063 filed on Apr. 26, 2018 and titled "Dosage form comprising two-dimensional structural elements", and the International Application No. PCT/US19/19004 filed on Feb. 21, 2019 and titled "Expanding structured dosage form".

BACKGROUND OF THE INVENTION

At present, the prevalent mode of drug delivery is by oral ingestion of solid dosage forms consisting of compacted drug and excipient particles. The ingested dosage form fragments into its constituents in the gastrointestinal fluid and the drug particles dissolve. The dissolved drug molecules are then absorbed by the gastrointestinal wall and its blood vessels, and are distributed to the disease-specific target sites in the human body.

The dissolution rate of the solid drug particles and the flux of drug molecules into the blood vessels generally are roughly proportional to the concentration gradients. The concentration gradients in turn are limited by the drug solubility. Thus, if the solubility is low the drug delivery rate is slow, and the efficacy of the drug therapy may be compromised.

Many target-specific drug compounds, however, are sparingly (or poorly) soluble in gastrointestinal fluid. Thus, over the years numerous techniques have been developed to alter the physical state of sparingly-soluble compounds. Such techniques include, for example, salt formation, phase transformation from crystalline to amorphous, polymorphic change, and formation of a solid solution.

For further details related to prior art techniques of formulating sparingly-soluble drugs, see, e.g., A. T. M. Serajuddin, Salt formation to improve drug solubility, Adv. Drug Del. Rev. 59 (2007) 603-616; B. C. Hancock, G. Zografi, Characteristics and significance of the amorphous state in pharmaceutical systems, J. Pharm. Sci. 86 (1997) 1-12; B. C. Hancock, M. Parks, What is the true solubility advantage for amorphous pharmaceuticals?, Pharm. Res. 17 (2000) 397-404; M. Pudipeddi, A. T. M. Serajuddin, Trends in solubility of polymorphs, J. Pharm. Sci. 94 (2005) 929-939.

Solid solutions of dispersed drug molecules in water-soluble excipient are especially promising. Upon contact with an aqueous fluid, the excipient dissolves rapidly. The drug molecules are released rapidly, too, as the surrounding excipient erodes.

Nonetheless, the design of dosage forms comprising a drug-excipient solid solution is fraught with numerous challenges both at the micro- and at the macro-scale.

Limitations of Present Technologies

For example, two limitations of the present solid-solution technologies are: (a) precipitation of drug molecules as particles upon exposure to a dissolution fluid, and (b) pore closing in the dosage form due to plasticization of the excipient. Both limitations can slow down the drug release rate. They are briefly discussed below.

Precipitation of Drug Molecules as Particles

FIG. 1a presents a non-limiting schematic of a microscopic element 110 (e.g., a particle, fiber, etc.) comprising sparingly-soluble drug molecules dissolved in a water-soluble, amorphous polymeric excipient. Upon immersion in an aqueous fluid 160 the excipient and the fluid 160 inter-diffuse to form a viscous layer 170 of drug, excipient, and water as shown in FIG. 1b. Within the viscous layer 170 the drug concentration may be greater than its solubility; thus drug particles may precipitate. At the exterior the layer 170 erodes into the dissolution fluid 160, thereby releasing drug molecules. Thus, if the fluid-penetrated element 170 is supersaturated and releases drug molecules faster than they precipitate in it, the drug concentration at the element-fluid interface 170 is greater than the solubility. The drug release rate then is enhanced compared with that of solid drug particles, and the dissolution fluid 160 may be supersaturated with drug (FIG. 1c). In the supersaturated fluid 160, however, the drug molecules may precipitate as particles until the solubility is reached (FIG. 1d). Thus, as shown in the non-limiting FIG. 1e the drug concentration in the dissolution fluid 160 after immersion of the solid-solution element 110 is enhanced somewhat compared with that after immersion of a solid drug particle. But due to particle precipitation both in the element 170 and in the dissolution fluid 160 the increase is limited.

Pore Closing in the Dosage Form

FIG. 2a presents an extant solid dosage form 210 comprising a porous, compacted mixture of particles of a drug-excipient solid solution and other granular excipients (such as insoluble spacers, water-swelling disintegrants, binders, and so on) after immersion in a dissolution fluid 260. As shown in FIG. 2b, the fluid percolates through the open pores and inter-diffuses with the water-soluble and water-swelling excipient. The bonds between the particles may then be severed and the particles may be released into the surrounding fluid 260.

The pores in the compacted microstructures, however, are small (a few micrometers in diameter) and not well connected. Thus, fluid percolation generally is non-uniform and slow, and the inter-particle bonds are not severed fast enough. As a result, if the volume fraction of the drug-excipient solid-solution particles is too large, due to the plasticization of the excipient a large fraction of the pores closes out. The dosage form may then form a thick viscous mass from which the drug cannot be released rapidly (FIGS.

2c and 2d). Thus, the volume fraction of the solid-solution particles in the dosage form is limited. This in turn limits the content (or mass) of sparingly-soluble drug and water-soluble excipient in the dosage form, and the drug delivery rate into the blood stream.

SUMMARY OF THE INVENTION

The dosage forms disclosed herein mitigate the present limitations. For example, to mitigate premature precipitation of drug particles a substantial amount of an amphiphilic polymer is embedded in the solid solution. The amphiphilic polymer self-assembles as micelles upon contact with a physiological fluid, thereby enhancing drug solubility. Moreover, to mitigate pore closing, the disclosed dosage forms comprise a substantially ordered microstructure comprising a three-dimensional structural framework of thin solid-solution elements with precisely controlled inter-element spacing and composition.

More specifically, in one aspect the disclosed pharmaceutical dosage form comprises a drug-containing solid having an outer surface and an internal three dimensional structural framework of one or more orderly arranged structural elements, said framework being contiguous with and terminating at said outer surface: said structural elements comprising particles, fibers, or sheets having segments spaced apart from adjoining segments, thereby defining free spaces, wherein a plurality of adjacent free spaces combine to define one or more interconnected free spaces forming an open pore network that extends over a length at least half the thickness of the drug-containing solid: said structural elements further comprising dissolved molecules or dispersed nanometer-scale aggregates of at least one sparingly-soluble active ingredient in an excipient matrix: wherein said excipient matrix comprises at least a water-soluble polymer carrier to carry the dissolved sparingly-soluble drug molecules and/or dispersed sparingly-soluble drug aggregates, and at least an amphiphilic polymer: whereby upon immersion in a physiological fluid, said open pore network enables wetting of the structural framework, so that the fluid interdiffuses with the framework, and the amphiphilic polymer enhances drug solubility.

In some embodiments, the surface composition of at least one element is hydrophilic.

In some embodiments, the surface composition of the three dimensional structural framework is hydrophilic.

In some embodiments, the surface composition of one or more elements or segments comprises silicon dioxide, talc, magnesium stearate, a polyol (e.g., mannitol, maltitol, erythritol, maltodextrin, lactitol, sorbitol, xylitol, isomalt, etc.), a sugar (e.g., glucose, fructose, sucrose, etc.), polyvinyl pyrrolidone, vinyl pyrrolidone, polyvinyl alcohol, polyethylene glycol, polyethylene oxide, and others.

In some embodiments, one or more free spaces are filled with a gas.

In some embodiments, free spaces are interconnected forming an open pore network that extends over a length at least equal to the thickness of the drug-containing solid.

In some embodiments, free spaces are interconnected forming an open pore network that extends over a length and width at least half the thickness of the drug-containing solid.

In some embodiments, free spaces are interconnected forming a three-dimensional open pore network that extends over a length, width, and thickness at least half the thickness of the drug-containing solid.

In some embodiments, free spaces are interconnected forming an open pore network that extends over the entire length, width, and thickness of the drug-containing solid.

In some embodiments, an open pore network comprises or occupies at least 40 percent (e.g., at least 50 percent, or at least 60 percent or at least 70 percent or at least 80 percent) of the free space of the drug-containing solid (e.g., at least 40 percent (e.g., at least 50 percent, or at least 60 percent or at least 70 percent or at least 80 percent or 100 percent) of the free space of the drug-containing solid are part of the same open pore network).

In some embodiments, the effective free spacing (e.g, the pore size or pore diameter) across the open pore network is greater than 5 µm (e.g., greater than 10 µm, or greater than 20 µm, or greater than 30 µm).

In some embodiments, the effective free spacing (e.g, the pore size or pore diameter) across the open pore network is in the range 5 µm-2.5 mm (e.g., 5 µm-2 mm, 5 µm-1.5 mm, or 5 µm-1.25 mm, or 5 µm-1 mm, or 10 µm-1.5 mm, or 20 µm-1.5 mm).

In some embodiments, the effective free spacing between segments across the one or more free spaces on average is in the range 1 µm-3 mm.

In some embodiments, the free spacing between segments of the structural elements is precisely controlled.

In some embodiments, one or more free spaces combine to form a channel having a cross section extending axially along its length from a first end to a second end, and wherein the length of the channel is greater than half the thickness of the drug-containing solid.

In some embodiments, the channel bifurcates into at least one other end (e.g., at least two other ends or at least three other ends or at least four other ends), and wherein the length of the channel from the first end to said other end is greater than half the thickness of the drug-containing solid.

In some embodiments, the cross section of a channel is greater than 10 µm×10 µm along the length of said channel.

In some embodiments, the three dimensional structural framework is solid.

In some embodiments, the three dimensional structural framework forms a continuous structure.

In some embodiments, at least one element or segment is bonded to another element or segment.

In some embodiments, one or more elements or segments are bonded to one or more other elements or segments at one or more point contacts.

In some embodiments, one or more elements or segments are bonded to one or more other elements or segments at one or more line contacts.

In some embodiments, the number of point contacts is greater than 100.

In some embodiments, the number of point contacts is precisely controlled.

In some embodiments, the number of line contacts is no greater than 10.

In some embodiments, the number of line contacts is greater than 10.

In some embodiments, the number of line contacts is precisely controlled.

In some embodiments, average contact width is no greater than 2 mm.

In some embodiments, average contact width is no greater than 0.9 times average thickness of the one or more structural elements.

In some embodiments, the three dimensional structural framework extends over a length, width, and thickness at least two (e.g., at least three, or at least four, or at least five, or at least six, or at least seven) times the average thickness of the one or more structural elements.

In some embodiments, the one or more elements comprise an average thickness in the range 1 µm-2 mm (e.g., 2 µm-2 mm, or 5 µm-2 mm, or 10 µm-2 mm).

In some embodiments, the thickness of the structural elements is precisely controlled.

In some embodiments, the three dimensional structural framework comprises stacked layers (or plies) of particles, fibers, or sheets, or any combinations thereof.

In some embodiments, one or more layers or plies are bonded to the layers or plies above or below said one or more layers.

In some embodiments, the three dimensional structural framework comprises stacked layers of one or more particles, and wherein a particle in a layer is bonded to at least one particle adjacent to said particle in said layer.

In some embodiments, the three dimensional structural framework comprises stacked layers of one or more particles, and wherein a particle in a layer is bonded to at least one particle in a plie above or below said layer.

In some embodiments, the three dimensional structural framework comprises stacked layers of one or more sheets, and wherein a sheet is separated from an adjacent sheet by one or more particles between said sheets.

In some embodiments, the three dimensional structural framework comprises stacked layers of one or more sheets, and wherein a sheet is separated from an adjacent sheet by at least one fiber between said sheets.

In some embodiments, the structural framework comprises a fibrous network having inter-fiber point contacts and fiber segments between adjacent contacts, and wherein the length of fiber segments between adjacent point contacts is precisely controlled.

In some embodiments, the structural framework comprises a fibrous network having inter-fiber point contacts and fiber segments between adjacent contacts, and wherein the length of fiber segments between adjacent point contacts is uniform across the fibrous network.

In some embodiments, the structural framework comprises a fibrous network having inter-fiber point contacts and fiber segments between adjacent contacts, and wherein the length of fiber segments between adjacent point contacts is between 20 µm and 2.5 mm (e.g., 20 µm-2 mm, or 30 µm-2 mm, or 30 µm-1.75 mm) on average.

In some embodiments, the structural framework comprises a fibrous network having inter-fiber contacts and fiber segments between adjacent contacts, and wherein the distance between adjacent point contacts is precisely controlled across said fibrous network.

In some embodiments, the structural framework comprises a fibrous network having inter-fiber contacts and fiber segments between such contacts, and wherein the distance between adjacent point contacts is uniform across said fibrous network.

In some embodiments, the structural framework comprises a fibrous network having inter-fiber contacts and fiber segments between such contacts, and wherein the distance between adjacent point contacts is between 20 µm and 2.5 mm (e.g., 20 µm-2 mm, or 30 µm-2 mm, or 30 µm-1.75 mm) on average.

In some embodiments, the structural framework comprises a fibrous network having inter-fiber point contacts defined by intersecting fibers or fiber segments, and wherein the angle of intersection at said point contacts is precisely controlled across said fibrous network.

In some embodiments, the structural framework comprises a fibrous network having inter-fiber point contacts defined by intersecting fibers or fiber segments, and wherein the angle of intersection at said point contacts is uniform across said fibrous network.

In some embodiments, the structural framework comprises a fibrous network having inter-fiber point contacts defined by intersecting fibers or fiber segments, and wherein the angle of intersection at said point contacts is between 40 and 90 (e.g., 50-90, or 60-90, or 70-90, or 80-90) degrees on average.

In some embodiments, the three dimensional structural framework comprises criss-crossed stacked layers of fibers.

In some embodiments, fibers in a layer intersect with fibers in the layers above or below, thereby defining point contacts, and wherein the layers are bonded at said point contacts.

In some embodiments, fibers in a layer contact fibers in the layers above or below, and wherein the layers are bonded at said contacts.

In some embodiments, one or more fibers or fiber segments in a layer are bonded to one or more fibers or fiber segments in the layer above or the layer below by one or more point contacts.

In some embodiments, at least 30 percent (e.g., at least 40 percent, or at least 50 percent, or at least 60 percent, or at least 70 percent) of the fiber length in a layer is aligned unidirectionally.

In some embodiments, at least 50 percent of the fiber length in a layer is aligned parallel to at least another fiber or fiber segment in said layer.

In some embodiments, one or more fibers or fiber segments in a layer are aligned parallel, and wherein the distance between adjacent, parallel fibers in said layer is uniform.

In some embodiments, the fibers or fiber segments of the layers above or below a layer are oriented at an angle greater than 25 degrees to the fibers or fiber segments in said layer.

In some embodiments, fibers in a layer intersect with fibers in the layers above or below, and wherein the angle of intersection is precisely controlled.

In some embodiments, fibers in a layer intersect with fibers in the layers above or below, and wherein the angle of intersection is greater than 25 degrees.

In some embodiments, the volume fraction of elements having at least one sparingly-soluble active ingredient dissolved as molecules or dispersed as nanometer-scale aggregates in a water-soluble excipient matrix is no greater than 0.8 (e.g., in the ranges 0.1-0.8, 0.2-0.8, 0.3-0.8, 0.35-0.8, 0.4-0.8) with respect to the volume of the drug-containing solid.

In some embodiments, the volume fraction of elements having at least one sparingly-soluble active ingredient dissolved as molecules or dispersed as nanometer-scale aggregates in a water-soluble excipient matrix that is further soluble in gastric acid is no greater than 0.8 (e.g., in the ranges 0.1-0.8, 0.2-0.8, 0.3-0.8, 0.35-0.8, 0.4-0.8) with respect to the volume of the drug-containing solid.

In some embodiments, the solubility of said sparingly-soluble drug in a physiological/body fluid under physiological conditions is no greater than 1 mg/ml.

In some embodiments, the weight fraction of sparingly-soluble drug in an element with respect to the total weight of said element is no greater than 0.65 (e.g., no greater than 0.6, or no greater than 0.5, or no greater than 0.45).

In some embodiments, the weight fraction of sparingly-soluble drug in the structural framework with respect to the total weight of said framework is no greater than 0.65 (e.g., no greater than 0.6, or no greater than 0.5, or no greater than 0.45).

In some embodiments, the concentration of sparingly-soluble drug is uniform (e.g., constant or almost constant or about constant) across the water-soluble or gastric acid-soluble excipient matrix.

In some embodiments, the concentration of sparingly-soluble drug is uniform across an element.

In some embodiments, the concentration of sparingly-soluble drug is uniform across the three dimensional structural framework.

In some embodiments, at least one water-soluble polymer carrier is absorptive of a physiological/body fluid, and wherein rate of penetration of the physiological/body fluid into an element or said absorptive excipient under physiological conditions is greater than the average fiber thickness divided by 3600 seconds.

In some embodiments, at least one water-soluble polymer carrier is absorptive of a physiological/body fluid, and wherein an effective diffusivity of physiological/body fluid in an element or said absorptive excipient is greater than $0.25 \times 10^{-11}$ m$^2$/s under physiological conditions.

In some embodiments, at least one water-soluble polymer carrier comprises an amorphous polymer.

In some embodiments, at least one water-soluble polymeric excipient comprises a solubility greater than 0.1 g/l in an aqueous physiological/body fluid under physiological conditions.

In some embodiments, dissolved molecules of the water-soluble polymer carrier comprise a diffusivity greater than $1 \times 10^{-12}$ m$^2$/s in a physiological/body fluid under physiological conditions.

In some embodiments, at least one water-soluble polymer carrier is selected from the group comprising hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, hydroxyethyl cellulose, methyl cellulose, hydroxypropyl methyl ether cellulose, starch, chitosan, pectin, polymethacrylates (e.g., poly(methacrylic acid, ethyl acrylate) 1:1, or butylmethacrylat-(2-dimethylaminocthyl)methacrylat-methylmathacrylat-copolymer), or vinylpyrrolidone-vinyl acetate copolymer.

In some embodiments, the molecular weight of at least one water-soluble polymer carrier is between 2 kg/mol and 700 kg/mol.

In some embodiments, the weight fraction of water-soluble polymer carrier in an element with respect to the total weight of said element is greater than 0.15.

In some embodiments, the weight fraction of water-soluble polymer carrier an element with respect to the total weight of said element is in the range 0.25-0.85.

In some embodiments, at least one amphiphilic polymer self-assembles in aqueous solutions to form regions of heterogeneous degree of hydrophobicity or hydrophilicity.

In some embodiments, the amphiphilic polymer self-assembles as micelles in aqueous solutions, and wherein the critical micelle concentration is smaller than 1 mg/ml.

In some embodiments, the molecular weight of at least one amphiphilic polymer is smaller than 500 kg/mol (e.g., smaller than 250 kg/mol, or smaller than 100 kg/mol, or smaller than 50 kg/mol, or smaller than 20 kg/mol, or smaller than 10 kg/mol).

In some embodiments, the molecular weight of at least one amphiphilic polymer is in the range 0.1 kg/mol-50 kg/mol (e.g., 0.1-25 kg/mol, 0.1-10 kg/mol, 0.1-5 kg/mol, 0.1-3 kg/mol, 0.1-2 kg/mol).

In some embodiments, a slope, a, of the drug solubility versus concentration of amphiphilic polymer in an aqueous solution (e.g., a physiological/body fluid under physiological conditions) is greater than 0.001.

In some embodiments, a slope, a, of the drug solubility versus concentration of amphiphilic polymer in an aqueous solution (e.g., a physiological/body fluid under physiological conditions) is greater than $0.05 \times c_0$, 0.05 times the drug solubility in said aqueous solution without excipient.

In some embodiments, at least one amphiphilic polymer is selected from the group comprising polyoxyl stearate, polyethylene glycol methyl ether-block-polylactide-co-glycolide, polyethylene glycol-polylactic acid (PEG-PLA) copolymer, poloxamer, lauroyl macrogol-32 glycerides, dendrimers (e.g., polyamidoamine dendrimer or a dendrimer consisting of an ethylene diamine core or a dendrimer comprising a repetitive branching of amido amine or a dendrimer comprising a primary amine surface), and others.

In some embodiments, the weight fraction of amphiphilic polymer in at least one element is between 0.05 and 0.7.

In some embodiments, the weight fraction of amphiphilic polymer in the three dimensional structural framework is between 0.05 and 0.7 (e.g., 0.1-0.7, 0.15-0.7, 0.2-0.7, 0.25-0.7, 0.2-0.6).

In some embodiments, the amphiphilic polymer is dissolved as molecules or dispersed as nanometer-scale aggregates in a water-soluble polymer carrier.

In some embodiments, the amphiphilic polymer is dispersed as particles of number-average size no greater than 50 μm (e.g., no greater than 40 μm, or no greater than 30 μm, or no greater than 20 μm, or no greater than 15 μm, or no greater than 10 μm) in a water-soluble polymer carrier.

In some embodiments, the concentration of amphiphilic polymer is uniform across an element.

In some embodiments, the concentration of amphiphilic polymer is uniform across the water-soluble or gastric-acid-soluble excipient matrix.

In some embodiments, the concentration of amphiphilic polymer is uniform across a region of an element comprising a composition of a sparingly-soluble drug and a water-soluble polymer carrier.

In some embodiments, the concentration of amphiphilic polymer is uniform across the three dimensional structural framework.

In some embodiments, the concentration of amphiphilic polymer is uniform across a region of the three dimensional structural framework comprising a composition of a sparingly-soluble drug and a water-soluble polymer carrier.

In some embodiments, at least a sparingly-soluble drug, at least a water-soluble polymer carrier, and at least an amphiphilic excipient are blended through the body of one or more elements.

In some embodiments, at least a sparingly-soluble drug, at least a water-soluble polymer carrier, and at least an amphiphilic excipient are blended through the body of the structural framework.

In some embodiments, upon immersion of the drug-containing solid in a physiological fluid, said fluid percolates more than 40 percent of the free spaces of said drug-containing solid in no more than 600 seconds of immersion.

In some embodiments, upon immersion of the drug-containing solid in a physiological fluid, said fluid percolates more than 60 percent of the free spaces of said drug-containing solid in no more than 300 seconds of immersion.

In some embodiments, upon immersion of the drug-containing solid in a physiological fluid, said fluid percolates more than 50 percent of the free spaces of said drug-containing solid in no more than 100 seconds of immersion.

In some embodiments, upon immersion in a physiological/body fluid the drug-containing solid transitions to a viscous medium, thereby expanding in all dimensions.

In some embodiments, the drug-containing solid expands due to the penetration of physiological or body fluid into the three dimensional structural framework of one or more elements.

In some embodiments, the drug-containing solid expands due to the penetration of physiological or body fluid into a water-soluble polymer carrier.

In some embodiments, at least one dimension of the drug-containing solid expands to at least 1.1 times its initial length while transitioning to a viscous medium.

In some embodiments, the drug-containing solid expands to at least 1.3 times its initial volume while transitioning to a viscous medium.

In some embodiments, at least one dimension of the drug-containing solid expands to at least 1.1 times its initial length within no more than 20 minutes of immersing in a physiological or body fluid.

In some embodiments, the drug-containing solid expands to at least 1.3 times its initial volume within no more than 20 minutes of immersing in a physiological or body fluid.

In some embodiments, the drug-containing solid expands isotropically while transitioning to a viscous medium.

In some embodiments, the drug-containing solid dissolves or disintegrates during or after transitioning to a viscous medium.

In some embodiments, a sparingly-soluble drug supersaturates in a physiological/body fluid upon immersion of the dosage form in said fluid under physiological conditions, where the mass of said sparingly-soluble drug in the dosage form is greater than the product of solubility and fluid volume.

In some embodiments, a sparingly-soluble drug supersaturates in a physiological/body fluid to a maximum supersaturation at least 1.5 upon immersion of the dosage form in said fluid under physiological conditions where the product of solubility and fluid volume is smaller than 0.5 times the mass of said sparingly-soluble drug in the dosage form.

In some embodiments, the tensile strength of at least one element is greater than 0.01 MPa (e.g., greater than 0.05 MPa or greater than 0.1 MPa).

In some embodiments, the tensile strength of the drug containing solid or three dimensional structural framework is greater than 0.01 MPa (e.g., greater than 0.05 MPa or greater than 0.1 MPa).

In some embodiments, the dosage form further comprises another drug-containing solid.

In another aspect, a pharmaceutical dosage form herein comprises a drug-containing solid having an outer surface and an internal three dimensional structural framework comprising a plurality of criss-crossed stacked layers of one or more fibrous structural elements, said framework contiguous with and terminating at said outer surface: said fibrous structural elements further having segments spaced apart from like segments of adjoining elements, thereby defining free spaces, wherein a plurality of adjacent free spaces of successive layers combine to define one or more interconnected free spaces forming an open pore network: said fibrous structural elements further comprising at least one sparingly-soluble active ingredient dissolved as molecules or dispersed as nanometer-scale aggregates in an excipient matrix: said excipient matrix comprising least a water-soluble polymer carrier to carry the dissolved sparingly-soluble drug molecules and/or dispersed sparingly-soluble drug aggregates, and at least an amphiphilic polymer: whereby upon immersion in a physiological fluid, said open pore network enables wetting of the structural framework, so that the fluid interdiffuses with the framework, and the amphiphilic polymer self-assembles as micelles, thereby enhancing drug solubility: the thickness of the fibrous structural elements is precisely controlled, and the average fiber thickness is in the range 10 µm-2 mm; and the free spacing between segments of the fibrous structural elements is precisely controlled, and the average free spacing between segments across the free spaces is in the range 10 µm-3 mm.

An aspect of a method of manufacturing pharmaceutical solid dosage forms according to the invention herein comprises the steps of injecting (e.g., feeding) at least one sparingly-soluble drug, at least one water-soluble excipient in which said sparingly-soluble drug is soluble, at least one amphiphilic excipient, and at least one solvent into an extrusion channel having a cross section extending along its length inside a housing; forming a plasticized solution by solvating at least one water-soluble excipient and dissolving at least one sparingly-soluble drug; conveying the plasticized solution towards an exit port of the extrusion channel by applying mechanical work on the plasticized solution; extruding the plasticized solution through an exit port to form at least one plasticized element; structuring at least one plasticized element to a three dimensional structural framework of one or more drug-containing elements; and solidifying one or more drug-containing elements to form a solid solution or a solid dispersion.

In another aspect, a method of manufacturing pharmaceutical solid dosage forms herein comprises the steps of injecting at least one sparingly-soluble drug and at least one thermoplastic, water-soluble excipient in which said sparingly-soluble drug is soluble into an extrusion channel having a cross section extending along its length inside a housing; heating the injected ingredients to form a plasticized solution by plasticizing at least one excipient and dissolving at least one sparingly-soluble active ingredient in said plasticized excipient; conveying the plasticized solution towards an exit port of the extrusion channel by applying mechanical work on the plasticized solution; extruding the plasticized solution through an exit port to form at least one plasticized element; structuring at least one plasticized element to a three dimensional structural framework of one or more drug-containing elements; and solidifying one or more drug-containing elements to form a solid solution or a solid dispersion.

In another aspect, a method of manufacturing pharmaceutical solid dosage forms herein comprises the steps of injecting granules of at least one water-soluble excipient into an extrusion channel having a cross section extending along its length inside a housing; injecting at least a first solvent in which at least one injected excipient is soluble into said extrusion channel; injecting at least a drug-solvent solution comprising dissolved molecules of sparingly-soluble drug and a second solvent into said extrusion channel to form a drug-excipient plasticized solution or dispersion; conveying the plasticized solution or dispersion towards an exit port of the extrusion channel by applying mechanical work on the plasticized solution or dispersion; extruding the plasticized solution or dispersion through an exit port to form at least one plasticized element; structuring at least one plasticized element to a three dimensional structural framework of one or more drug-containing elements; and solidifying one or more drug-containing elements to form a solid solution or a solid dispersion.

In some embodiments, the method herein further comprises feeding at least one amphiphilic polymer into an extrusion channel.

In some embodiments, the method herein further comprises blending at least a water-soluble polymer carrier, at least an amphiphilic polymer, and at least a sparingly-soluble drug to form a uniform mixture or plasticized solution.

In some embodiments, plasticized solution or dispersion is extruded through at least one exit port of the extrusion channel designed to form a fibrous extrudate comprising at least one plasticized fiber having a fiber thickness less than 2.5 mm (e.g., less than 2 mm, or less than 1.5 mm, or in the ranges 1 µm-2.5 mm; 2.5 µm-2 mm; 5 µm-1.5 mm; or 10 µm-1.5 mm).

In some embodiments, plasticized solution or dispersion is extruded through at least one exit port of the extrusion channel by an advancing piston.

In some embodiments, the structuring of at least one plasticized element to a three dimensional structural network of one or more elements is performed by 3D-patterning said at least one plasticized fiber on a substrate.

In some embodiments, the substrate is defined by or attached to a movable stage.

In some embodiments, the stage is movable (e.g., translatable) in at least two directions relative to the at least one exit port for depositing one or more plasticized fibers along a path defined by the motion of said stage.

In some embodiments, the stage is movable (e.g., translatable) in at least three directions relative to the at least one exit port for depositing one or more plasticized fibers along a path defined by the motion of said stage.

In some embodiments, two directions in which the stage is movable span a plane oriented at an angle to the central axis of the extruded fiber to pattern said fiber on a substrate defined by or attached to said stage, and wherein said stage is further movable in a third direction oriented at an angle to said plane to control the distance between said substrate and an exit port.

In some embodiments, the conveying is performed using a screw.

Elements of embodiments described with respect to one aspect of the invention can be applied with respect to another aspect. By way of example but not by way of limitation, certain embodiments of the claims described with respect to the first aspect can include features of the claims described with respect to the second or third aspect, and vice versa.

This invention may be better understood by reference to the accompanying drawings, attention being called to the fact that the drawings are primarily for illustration, and should not be regarded as limiting.

BRIEF DESCRIPTION OF THE DRAWINGS

The objects, embodiments, features, and advantages of the present invention are more fully understood when considered in conjunction with the following accompanying drawings.

DEFINITIONS

Figure 1:
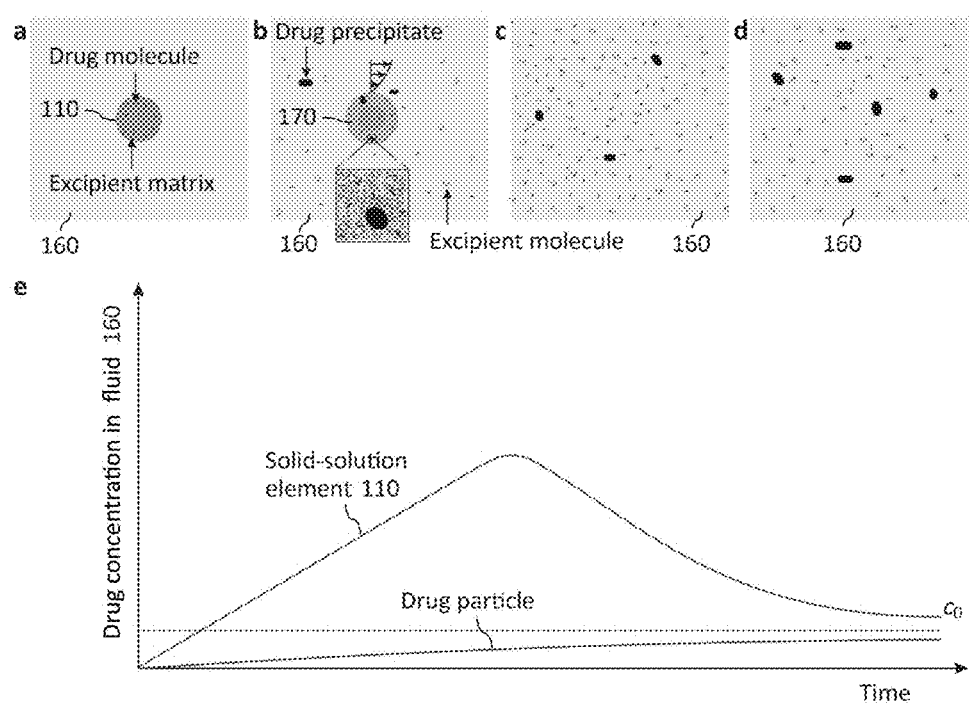
FIG. 1 shows a solid-solution element comprising sparingly-soluble drug molecules dispersed in a water-soluble excipient after immersion in a dissolution fluid.
Figure 2:
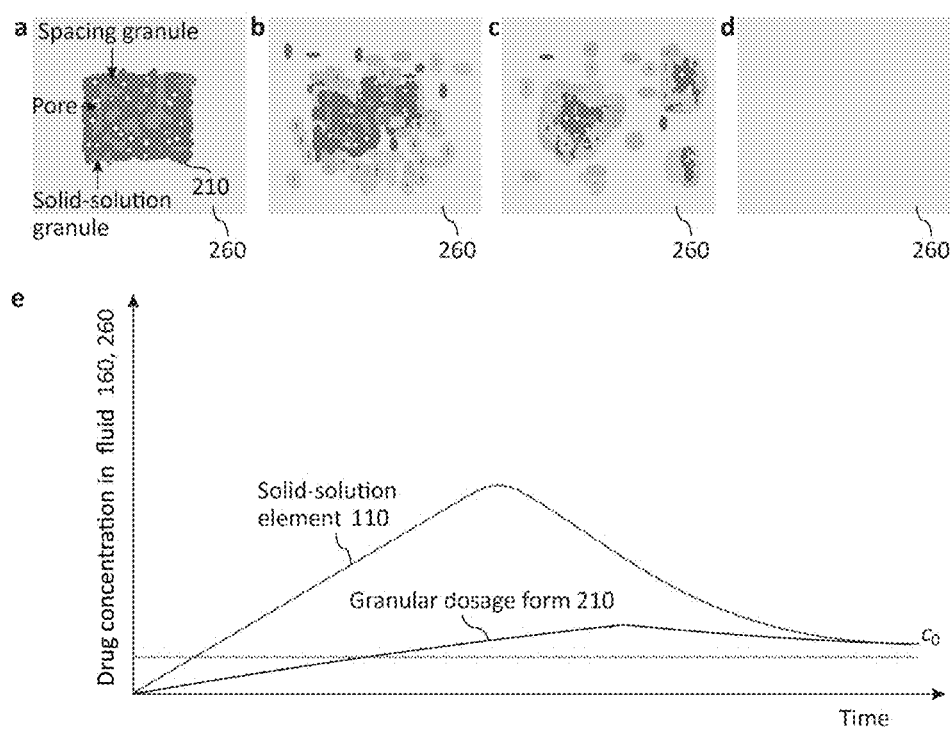
FIG. 2 illustrates the disintegration process of a state-of-the-art dosage form comprising a compacted mixture of solid-solution granules and other granular excipients after immersion in a dissolution fluid.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients" and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

Furthermore, in the context of some embodiments herein where the average thickness of one or more elements is greater than about 30-100 µm, a three dimensional structural framework (or network) of one or more elements comprises a drug-containing structure (e.g., an assembly or an assemblage or an arrangement of one or more drug-containing elements) that extends over a length, width, and thickness greater than 100 µm. This includes, but is not limited to, drug-containing structures that extend over a length, width, and thickness greater than 200 µm, or greater than 300 µm, or greater than 500 µm, or greater than 700 µm, or greater than 1 mm, or greater than 1.25 mm, or greater than 1.5 mm, or greater than 2 mm.

In some embodiments where the average thickness of one or more elements is smaller than about 30-100 µm, a three dimensional structural framework (or network) of drug-containing elements may comprise a drug-containing structure (e.g., an assembly or an assemblage of one or more elements) that extends over a length, width, and thickness greater than the average thickness of at least one element (or at least one segment) in the three dimensional structural framework (or network) of elements. This includes, but is not limited to drug-containing structures that extend over a length, width, and thickness greater than 1.5, or greater than 2, or greater than 2.5, or greater than 3, or greater than 3.5, or greater than 4 times the average thickness of at least one element (or at least one segment) in the three dimensional structural framework (or network) of elements.

In some embodiments, a three dimensional structural framework (or network) of drug-containing elements is continuous. Furthermore, in some embodiments, the drug-containing elements are bonded to each other or interpenetrating.

It may be noted that the terms "three dimensional structural network" and "three dimensional structural framework" are used interchangeably herein. Also, the terms "three dimensional structural framework of drug-containing elements", "three dimensional structural framework of elements", "three dimensional structural framework of one or more elements", "three dimensional structural framework of one or more drug-containing elements", "three dimensional framework of elements" and "three dimensional framework", and "structural framework" are used interchangeably herein.

In the invention herein, a "structural element" or "element" is refers to a two-dimensional element (or 2-dimensional structural element), or a one-dimensional element (or 1-dimensional structural element), or a zero-dimensional element (or 0-dimensional structural element).

As used herein, a two-dimensional structural element is referred to as having a length and width much greater than its thickness. In the present disclosure, the length and width of a two-dimensional structural element are greater than 2 times its thickness. An example of such an element is a "sheet". A one-dimensional structural element is referred to as having a length much greater than its width or thickness. In the present disclosure, the length of a one-dimensional structural element is greater than 2 times its width and thickness. An example of such an element is a "fiber". A zero-dimensional structural element is referred to as having a length and width of the order of its thickness. In the present disclosure, the length and width of a zero-dimensional structural element are no greater than 2 times its thickness. Furthermore, the thickness of a zero-dimensional element is less than 2.5 mm. Examples of such zero-dimensional elements are "particles" or "beads" and include polyhedra, spheroids, ellipsoids, or clusters thereof.

Moreover, in the invention herein, a segment of a one-dimensional element is a fraction of said element along its length. A segment of a two-dimensional element is a fraction of said element along its length and/or width. A segment of a zero-dimensional element is a fraction of said element along its length and/or width and/or thickness. The terms "segment of a one-dimensional element", "fiber segment", "segment of a fiber", and "segment" are used interchangeably herein. Also, the terms "segment of a two-dimensional element" and "segment" are used interchangeably herein. Also, the terms "segment of a zero-dimensional element" and "segment" are used interchangeably herein.

As used herein, the terms "fiber", "fibers", "one or more fibers", "one or more drug-containing fibers", and "drug-containing fibers", are used interchangeably. They are understood as the solid, drug-containing structural elements (or building blocks) that make up the three dimensional structural network (e.g., the dosage form structure or the structure of a drug-containing solid). A fiber has a length much greater than its width and thickness. In the present disclosure, a fiber is referred to as having a length greater than 2 times its width and thickness (e.g., the length is greater than 2 times the fiber width and the length is greater than 2 times the fiber thickness). This includes, but is not limited to a fiber length greater than 3 times, or greater than 4 times, or greater than 5 times, or greater than 6 times, or greater than 8 times, or greater than 10 times, or greater than 12 times the fiber width and thickness. In other embodiments that are included but not limiting in the disclosure herein, the length of a fiber may be greater than 0.3 mm, or greater than 0.5 mm, or greater than 1 mm, or greater than 2.5 mm.

Moreover, as used herein, the term "fiber segment" or "segment" refers to a fraction of a fiber along the length of said fiber.

In the invention herein, fibers (or fiber segments) may be bonded, and thus they may serve as building blocks of "assembled structural elements" with a geometry different from that of the original fibers. Such assembled structural elements include two-dimensional elements, one-dimensional elements, or zero-dimensional elements.

In the invention herein, drug release from a solid element (or a solid dosage form, or a solid matrix, or a drug-containing solid) refers to the conversion of drug (e.g., one or more drug particles, or drug molecules, or clusters thereof, etc.) that is/are embedded in or attached to the solid element (or the solid dosage form, or the solid matrix, or the drug-containing solid) to drug in a dissolution medium.

A sparingly-soluble drug herein comprises an active ingredient or drug with a solubility in physiological fluid or body fluids (or a dissolution medium or an aqueous solution) smaller than 1 mg/ml under physiological conditions. This includes, but is not limited to a solubility in physiological fluid or body fluid under physiological conditions smaller than 0.5 mg/ml, or smaller than 0.2 mg/ml, or smaller than 0.1 mg/ml, or smaller than 0.05 mg/ml, or even smaller. It may be noted that the terms "sparingly-soluble drug", "sparingly water-soluble drug", and "poorly-soluble drug" are used interchangeably herein.

In the invention herein, a solid solution of a drug and an excipient is a solid material comprising dissolved molecules of said drug in said excipient. Typically, the mass of said drug that is molecularly dissolved in said excipient is greater than 20 percent of the total mass of said drug dissolved or dispersed in said excipient. This includes, but is not limited to a mass of said drug that is molecularly dissolved in said excipient greater than 30 percent, or greater than 40 percent, or greater than 50 percent, or greater than 60 percent, or greater than 70 percent or greater than 80 percent, or greater than 90 percent, or greater than 95 percent of the total mass of said drug dissolved or dispersed in said excipient.

In the invention herein, a "drug nano-particle" or "drug nano-particles" or "nanometer-scale agglomerates of drug" or "nanometer-scale agglomerates of drug and excipient" or "nanometer-scale aggregates of drug" are referred to as particles or agglomerates of drug or drug molecules with an average size (e.g., a length, width, diameter, etc.) no greater than 5 µm. This includes, but is not limited to particles or agglomerates of drug or drug molecules with an average size no greater than 4 µm, or no greater than 3 µm, or no greater than 2 µm, or no greater than 1 µm.

In the invention herein, a drug is understood "soluble" in an excipient (e.g., a water-soluble polymer carrier, etc.) if at least 0.5 weight percent of said drug can be dissolved as molecules in a solid solution of said drug and excipient (e.g., the weight fraction of said drug in the form of dissolved molecules is at least 0.005 with respect to the total weight of drug and excipient). This includes, but is not limited to a drug being soluble in an excipient if more than 1 wt %, or more than 2 wt %, or more than 5 wt % of said drug can be dissolved as molecules in a solid solution of said drug and excipient.

A viscous medium may be referred to a viscous solution, viscous dispersion, or viscous mass having a shear viscosity much smaller than the "viscosity" of a solid, but greater than the shear viscosity of "the" or "a" dissolution fluid. Thus, in some embodiments the shear viscosity of a viscous medium is much less than that of a solid but greater than 2, or greater than 4, or greater than 5, or greater than 6, or greater than 7, or greater than 8, or greater than 10, or greater than 12, or greater than 15 times the viscosity of "the" or "a" dissolution fluid.

Finally, as used herein, the terms "dissolution medium", "physiological fluid", "body fluid", "dissolution fluid", "medium", "fluid", "aqueous solution", and "penetrant" are used interchangeably. They are understood as any fluid produced by or contained in a human body under physiological conditions, or any fluid that resembles a fluid produced by or contained in a human body under physiological conditions. Examples include, but are not limited to: water, saliva, stomach fluid, gastrointestinal fluid, saline, etc, at a temperature of 37° C., and a pH value adjusted to the relevant physiological condition.

DETAILED DESCRIPTION OF THE INVENTION

Aspects of the Dosage Form

Figure 3:
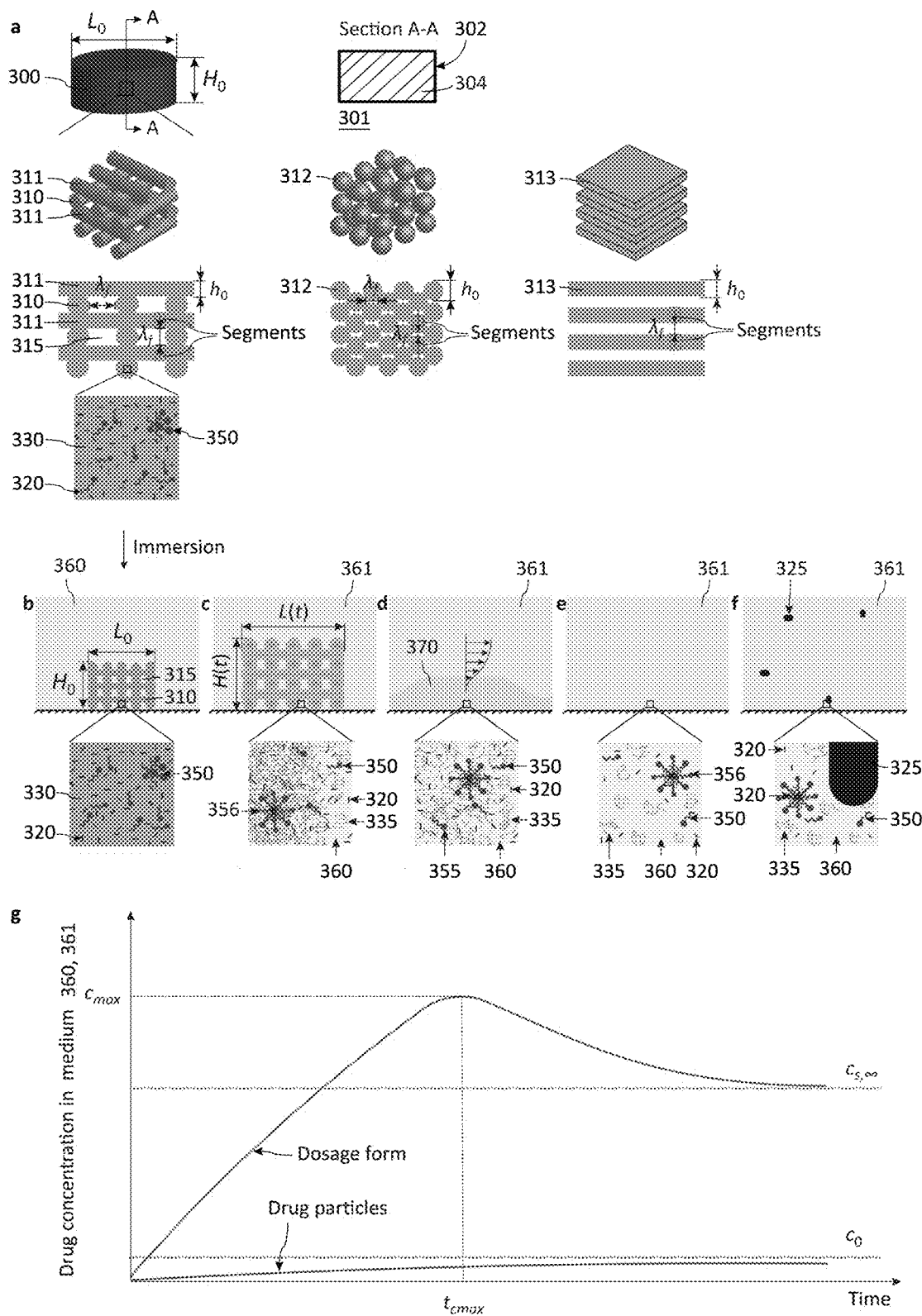
FIG. 3 shows (a) a non-limiting schematic of a dosage form according to the invention herein, (b)-(f) the evolution of its macro-, and microstructure after immersion in a dissolution fluid, and (g) the evolution of drug concentration in said dissolution fluid.

FIG. 3a presents a non-limiting example of a pharmaceutical dosage form according to the invention herein. The dosage form 300 comprises a drug-containing solid 301 having an outer surface 302 and an internal three dimensional structural framework 304 (e.g., a continuous, three-dimensional skeletal structure, or a three dimensional network, or a three dimensional skeleton) of one or more substantially orderly arranged structural elements 310, 311, 312, 313 (e.g., the elements are fixed or non-movable within the framework). The framework 304 is contiguous with and terminates at said outer surface 302.

Figure 12:
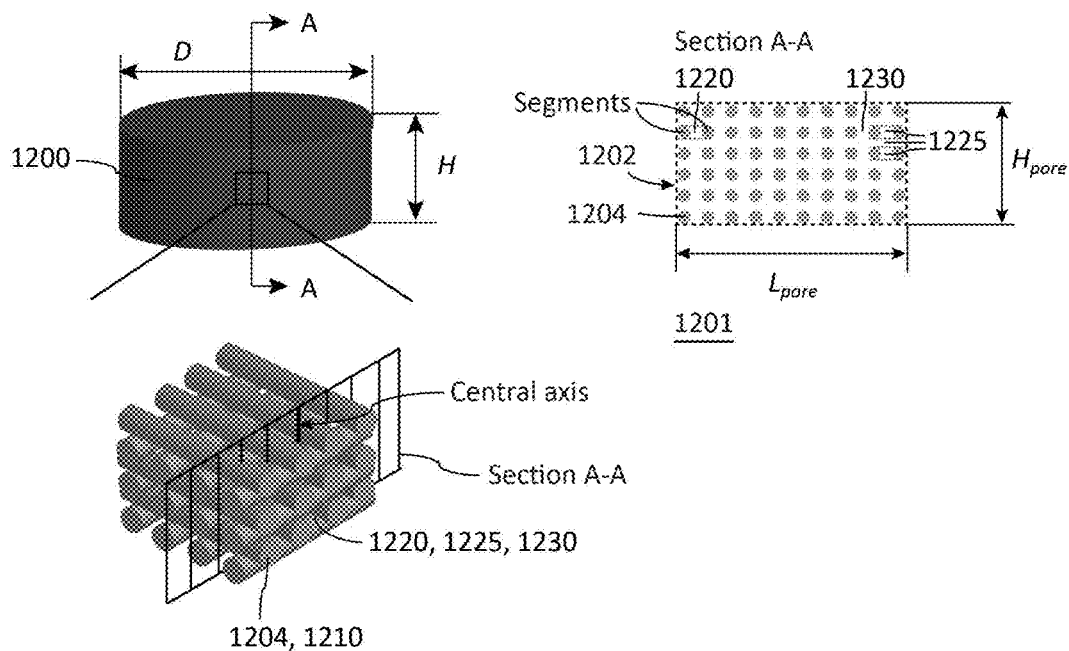
FIG. 12 is a non-limiting schematic of a fibrous dosage form according to the invention herein and its microstructure.

The structural elements 310, 311, 312 may comprise fibers 310, beads (also referred to herein as "particles") 311, sheets 312, or any combinations thereof. The elements 310, 311, 312, 313 further comprise segments spaced apart from segments of adjoining elements (or segments) 310, 311, 312, thereby defining free spaces 315. A plurality of adjacent free spaces 315 combine to define one or more interconnected free spaces 315 forming an open pore network (e.g., at least one open channel, or a network of open channels, or connected open channels, or a network comprising channels wherein each channel or point in the network is accessible from another channel or point in the network, or a network comprising channels wherein a continuous, open path exists from any channel or point in the network to any other channel or point in the network) that extends over a length at least half the thickness of the drug-containing solid 301. Further details about how interconnected free spaces are defined herein and how the length of the open pore network may be measured are provided in FIGS. 12 and 13, and subsection b "Geometry of drug-containing solid and three dimensional structural framework" of section "Embodiments of the dosage form". Moreover, free space may be filled with a gas, a solid that is removable by a physiological fluid, and so on. For further information related to the composition of a free space, see, e.g., the U.S. Application Ser. No. 15/482,776 titled "Fibrous dosage form".

In some preferred embodiments, the internal three dimensional structural framework 304 comprises a plurality of criss-crossed stacked layers of fibrous structural elements 310, 311. Herein criss-crossed stacked layers of fibrous structural elements 310, 311 are referred to as plies (e.g., "layers" or "planes") of fibers 310, 311 or fiber segments that are stacked in a cross-ply arrangement. In cross-ply arrangements, fibers 310 (or fiber segments) in a ply (or "layer" or "plane") are oriented transversely or at an angle to the fibers 311 in the ply above or below. Moreover, in cross-ply structures an open pore network 315 typically extends over the entire length, width, and thickness of the drug-containing solid 301. All free spaces 315 are open and interconnected forming a single interconnected pore network 315.

In other non-limiting embodiments the internal three dimensional structural framework 304 may comprise a plurality of stacked, bonded layers of beads (e.g., particles) 312 or stacked layers of sheets 313 (or sheet-shaped segments). The sheets may be aligned parallel or almost parallel to each other.

The structural elements 310, 311, 312, 313 further comprise at least one sparingly-soluble active ingredient (e.g., at least one sparingly-soluble drug) dissolved as drug molecules 320 or dispersed as nanometer-scale aggregates in an excipient matrix 330, 350. Thus the drug forms a solid solution or a solid dispersion with said excipient matrix 330, 350.

The excipient matrix comprises at least a water-soluble polymer carrier 330 to carry (e.g., to embed, or to accommodate, or to fix, or to freeze, or to hold) the dispersed sparingly-soluble drug molecules 320 or aggregates in the three dimensional structural framework of elements 310, 311, 312, 313. The water-soluble polymer carrier 330 is also referred to herein as "water-soluble polymeric carrier", "water-soluble carrier", "water-soluble carrier excipient" or "strength-enhancing excipient".

The excipient matrix 330, 350 further comprises at least an amphiphilic polymer 350 for enhancing drug solubility in aqueous solutions. In the invention herein, an amphiphilic polymer molecule is referred to a molecule (e.g., a copolymer) comprising at least one hydrophilic branch (or block) and at least one hydrophobic branch (or block). The amphiphilic polymer is also referred to herein as "amphiphilic excipient" or "solubility-enhancing excipient".

As shown schematically in FIG. 3b, upon immersion of the dosage form 300 in a dissolution fluid 360, 361, the dissolution fluid 360, 361 percolates an open pore network 315. After percolation the dissolution fluid partially or entirely wets the three dimensional structural framework 310, 311, 312, 313. In the invention herein, a fluid is referred to as "wetting" a solid body, such as the three dimensional structural framework, if said fluid covers (e.g., is in direct contact with) the (or a) surface of said solid body. A fluid is referred to as "partially wetting" a solid body, such as the three dimensional structural framework, if said fluid covers (e.g., is in direct contact with) at least 25 percent of the surface of said solid body. This includes, but is not limited to covering at least 30 percent, or at least 40 percent, or at least 50 percent or at least 60 percent, or at least 70 percent, or at least 75 percent, or at least 80 percent of the surface of said solid body.

At the contact surface, also referred to herein as "interface", of the dissolution fluid 360, 361 and the three-dimensional structural framework, the dissolution fluid 360, 361 may diffuse into the framework 310, 311, 312, 313. Thus the water concentration in the structural framework may increase from the contact surface inwards. Accordingly, as shown schematically in the non-limiting FIG. 3c, from the contact surface inwards the structural framework may transition from solid to a viscous medium 370. The viscous medium is also referred to herein as "viscous solution".

At the macro-scale, due to the absorption of water the solid, three-dimensional structural framework may expand in all dimensions while transitioning to viscous (FIG. 3c). Herein a body or sample is understood as "expanding in all dimensions" if at least a length of said sample (e.g., the length, and/or width, and/or thickness, etc. of said sample) and the volume of said sample are increasing. In a structure that expands in all dimensions the pores or free spaces 315 may remain entirely or at least partially or temporarily open during expansion. Thus, during the solid-to-viscous transition the dissolution fluid 360, 361 may continue to flow into the free spaces 315 between the structural elements 310, 311, 312, 313 of the expanding framework. The expanding framework may absorb more water, and the concentration of excipient molecules (e.g., the concentration of fluidized excipient molecules) in the viscous dosage form structure (e.g., the viscous part of the structural framework during and after the solid-to-viscous transition) decreases. As a result, the viscosity of an expanding viscous dosage form structure ever decreases, and the deformation, break up, and disintegration or dissolution of the structure are promoted.

At the micro- or nano-scale, as shown schematically in the non-limiting inset of FIG. 3c the interior of the viscous medium consists of plasticized carrier excipient molecules 335, drug molecules 320, and amphiphilic excipient molecules 355. Within the viscous medium, moreover, the amphiphilic polymer molecules 355 may form self-assemblages 356 (e.g., micelles, emulsions, etc.). The solubility of drug molecules 320 within such assemblages 356 may be far greater than within the remainder of the viscous medium. Thus, drug molecules 320 may accumulate in such self-assemblages 356, thereby increasing the "solubility" (e.g., the average solubility or the overall solubility) of drug. Thus, due to the presence of amphiphilic excipient 355, 356 the drug solubility may be substantially greater in the viscous medium than in the "pure" dissolution fluid 360 (e.g., the dissolution fluid without any dissolved amphiphilic excipient molecules).

Nonetheless, if the concentration of drug molecules 320 in the viscous medium is greater than the solubility, drug particles may nucleate and grow. The terms "nucleate and grow" and "precipitate" are used as equivalents herein.

At the contact surface of the dissolution fluid 360, 361 and the three-dimensional structural framework 310, moreover, the composition of the framework (e.g., the water-soluble polymeric carrier 330, 335 drug 320, amphiphilic polymer 350, 355, 356 etc.) may diffuse into the dissolution fluid 360, 361. Thus drug 320 and excipient 330, 335, 350, 355, 356 may be released from the framework or drug-containing solid into the dissolution fluid 360, 361. Within the dissolution fluid 360, 361, therefore, the concentration of drug and excipient molecules 350, 355 356 increases.

Eventually, as shown schematically in FIG. 3d, fibers or elements may coalesce or the viscosity of the structure may be so low that it collapses or deforms to form a low-viscosity medium (also referred to herein as "viscous solution") 370. The low-viscosity medium 370 may erode or dissolve into the dissolution fluid 361, thereby continuing to release drug 320 and excipient molecules 335, 355 or assemblages (e.g., micelles) 356.

If the low-viscosity medium is supersaturated with drug molecules, and the drug molecules 320 are released into the dissolution fluid faster than they precipitate in the low-viscosity medium, excessive precipitation of drug in the low-viscosity medium may be prevented kinetically. Also, if drug molecules are released from a supersaturated low-viscosity (or viscous) medium into a dissolution fluid 361, 361, and the immersed drug mass per unit volume of the dissolution fluid is greater than the solubility of drug in the terminal drug-excipient-dissolution fluid solution, the dissolution fluid 361, too, may supersaturate with drug (e.g., the drug concentration in the dissolution fluid 361 may reach a concentration greater than the solubility). Within the supersaturated dissolution fluid 361, however, as shown in the non-limiting FIGS. 3e and 3f drug particles may nucleate and grow with time until the solubility in the terminal drug-excipient-dissolution fluid solution is reached.

FIG. 3g presents a schematic of the drug concentration versus time after immersion of a non-limiting disclosed dosage form 300 and non-limiting conventional drug particles in a dissolution fluid 360, 361 of small volume. In the invention herein, a dissolution fluid of small volume is also referred to as a system where the immersed drug mass per unit volume of the dissolution fluid is greater than the solubility in the terminal drug-excipient-dissolution fluid solution. The drug particles may release drug slowly: the drug concentration in the dissolution fluid may increase slowly and plateau towards the solubility of drug in the pure dissolution fluid. The dosage form 300, by contrast, may release drug much faster. Moreover, because drug molecules may be kinetically retained and released, the dissolution fluid may supersaturate with drug and reached a maximum concentration, $c_{max}$, corresponding to the maximum supersaturation, $S_{max}$. The drug concentration may then drop to the solubility in the terminal drug-excipient-dissolution fluid solution. Due to the large amount of solubility-enhancing excipient released into the dissolution fluid the terminal solubility may be greater than the solubility of drug in the pure dissolution fluid (e.g., the dissolution fluid without excipient). Thus, due to kinetic and thermodynamic effects the disclosed dosage form may enable to greatly enhance the drug concentration in a dissolution fluid, for enhancing the drug delivery rate into the blood stream.

It may be noted that in some embodiments, the dosage forms disclosed herein further comprise another drug-containing solid. Additional embodiments of the dosage forms disclosed herein are described throughout this specification.

Dosage Form Design Considerations

The following examples present non-limiting ways by which the drug release and disintegration behavior of the disclosed dosage forms may be modeled. The non-limiting models presented refer to a pharmaceutical dosage form comprising a drug-containing solid having an outer surface and an internal structure contiguous with and terminating at said outer surface. The internal structure comprises a three dimensional structural framework of at least one solid element.

The design considerations, models, and design examples will enable one of skill in the art to more readily understand the details and advantages of the invention. They are for illustrative purposes and are not meant to be limiting in any way.

(a) Drug Weight Fraction in Elements

Figure 4:
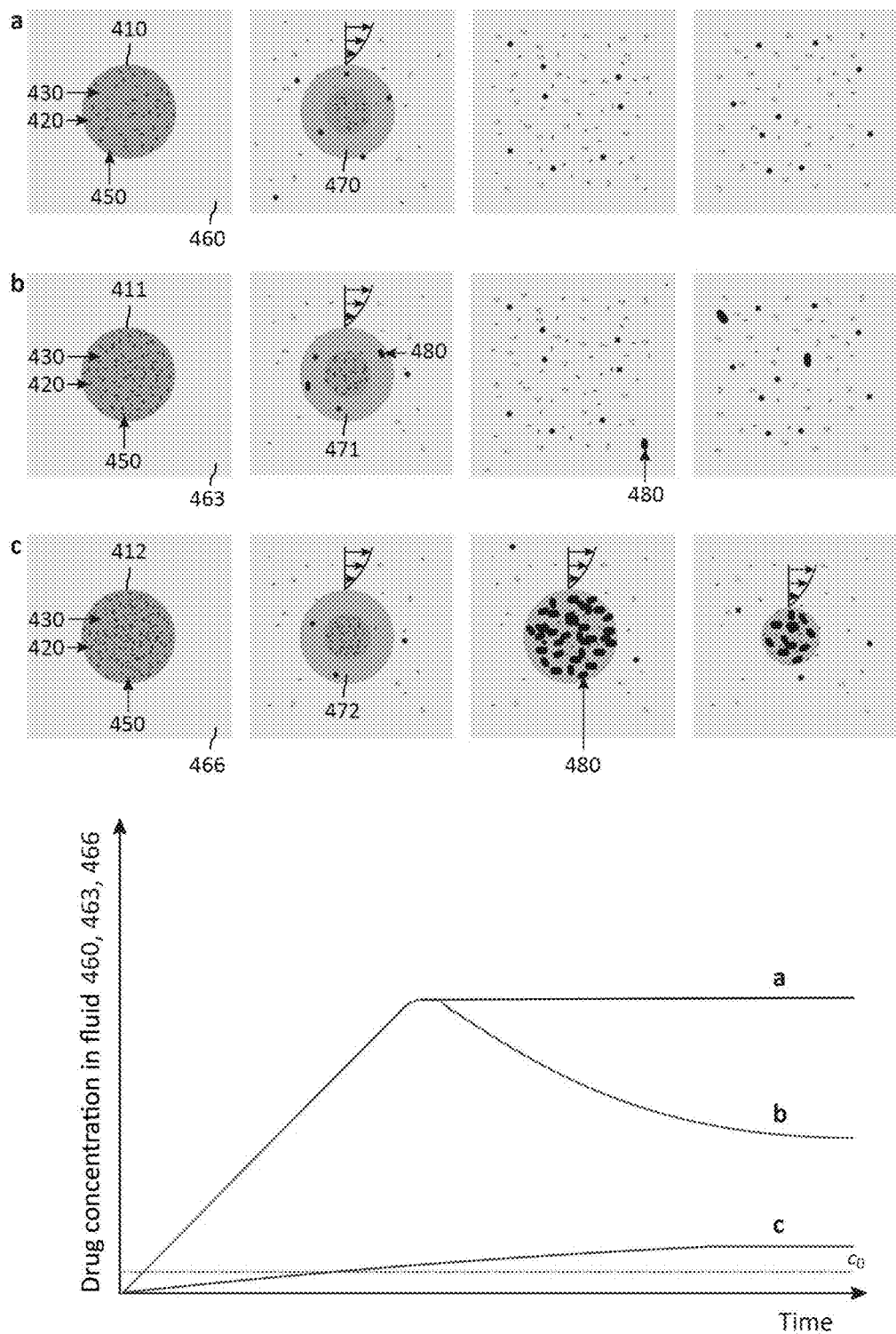
FIG. 4 schematically shows three solid-solution elements with different weight fractions of drug and excipient after immersion in a dissolution fluid, and the corresponding profiles of the drug concentration in the fluid versus time.

FIG. 4 presents non-limiting illustrations of single elements 410, 411, 412 after immersion in a dissolution fluid 460, 463, 466 and the corresponding profiles of drug concentration in the dissolution fluid 460, 463, 466 versus time. The elements 410, 411, 412 comprise at least sparingly water-soluble drug molecules 420 dissolved in a water-soluble polymeric carrier excipient 430. The elements 410, 411, 412 further comprise an amphiphilic excipient 450 for enhancing drug solubility in aqueous solutions 460, 463, 466. The three illustrations and curves a, b, and c represent different weight fractions of drug molecules 420 in the elements 410, 411, 412.

As described above, initially all three elements 410, 411, 412 are solid solutions of the drug 420 and excipient 430, 450 molecules. As the dissolution fluid 460, 463, 466 penetrates the interior of an element 410, 411, 412, however, a viscous drug-excipient-water solution 470, 471, 472 forms at the surface and propagates inwards. The mobility of drug 420 and excipient 430, 450 molecules in the viscous solution 470, 471, 472 is greater and the drug solubility smaller than in the dry element 410, 411, 412. Thus, depending on the drug weight fraction, $w_d$, in the solid-solution dry element 410, 411, 412 three types of microstructural evolution may be differentiated.

In the first type, represented by illustration and curve a, $w_d$ is so small that the drug concentration in the viscous solution 470 is smaller than its solubility at any time. The element 410, 470 simply erodes due to the convection of drug 420 and excipient 430, 450 molecules from the element surface 470 into the dissolution fluid 460. In the dissolution fluid 460, too, the drug concentration remains below solubility. The drug concentration increases steadily and plateaus to the terminal value (curve a).

In the second type, represented by illustration and curve b, $w_d$ is greater: the viscous solution 471 supersaturates with drug molecules, and drug particles 480 are likely to precipitate in the element 411, 471. If the supersaturation is small, however, the precipitation rate within the element 411, 471 will be much slower than the drug release rate from the element 411, 471 into the dissolution fluid 463. As a result, virtually all drug is released as molecules, much as in the previous case. The drug concentration in the dissolution fluid 463 raises quickly to a maximum greater than the solubility in the terminal solution. Past the maximum, therefore, drug particles 480 precipitate in the dissolution fluid and the drug concentration drops until the solubility in the terminal drug-excipient-dissolution fluid solution is reached (curve b).

In the third type, represented by illustration and curve c, $w_d$ is very large. Thus, the supersaturation in the fluid-penetrated annulus 472 will be far greater than unity, and the precipitation rate within the element 412, 472 will be greater than the drug release rate. Consequently, drug particles 480 precipitate and accumulate in the element 412, 472. The drug particles 480 block erosion of the element 412, 472, and hence the element's 412, 472 erosion rate is reduced greatly compared with the previous cases. Also, the release rate of drug molecules 420 is reduced. The drug concentration raises slowly to about the solubility in the terminal solution. The solubility in the terminal solution is smaller than in the previous cases because the amount of solubility-enhancing excipient 450 in the element 412 initially (e.g., the concentration of solubility-enhancing excipient in the terminal solution) is smaller (curve c).

Thus, for delivering a desired amount of sparingly-soluble drug with a dosage form of limited volume, the weight fractions of drug and excipient in the elements are crucial and should be optimized. More specifically, the drug weight fraction (e.g., the weight fraction of dissolved drug molecules or dispersed nanometer-scale aggregates) should be smaller than a critical value for releasing drug as molecules (e.g., the drug weight fraction should be less than a critical value above which drug particle precipitation in the framework, or an element, is excessive).

Figure 5:
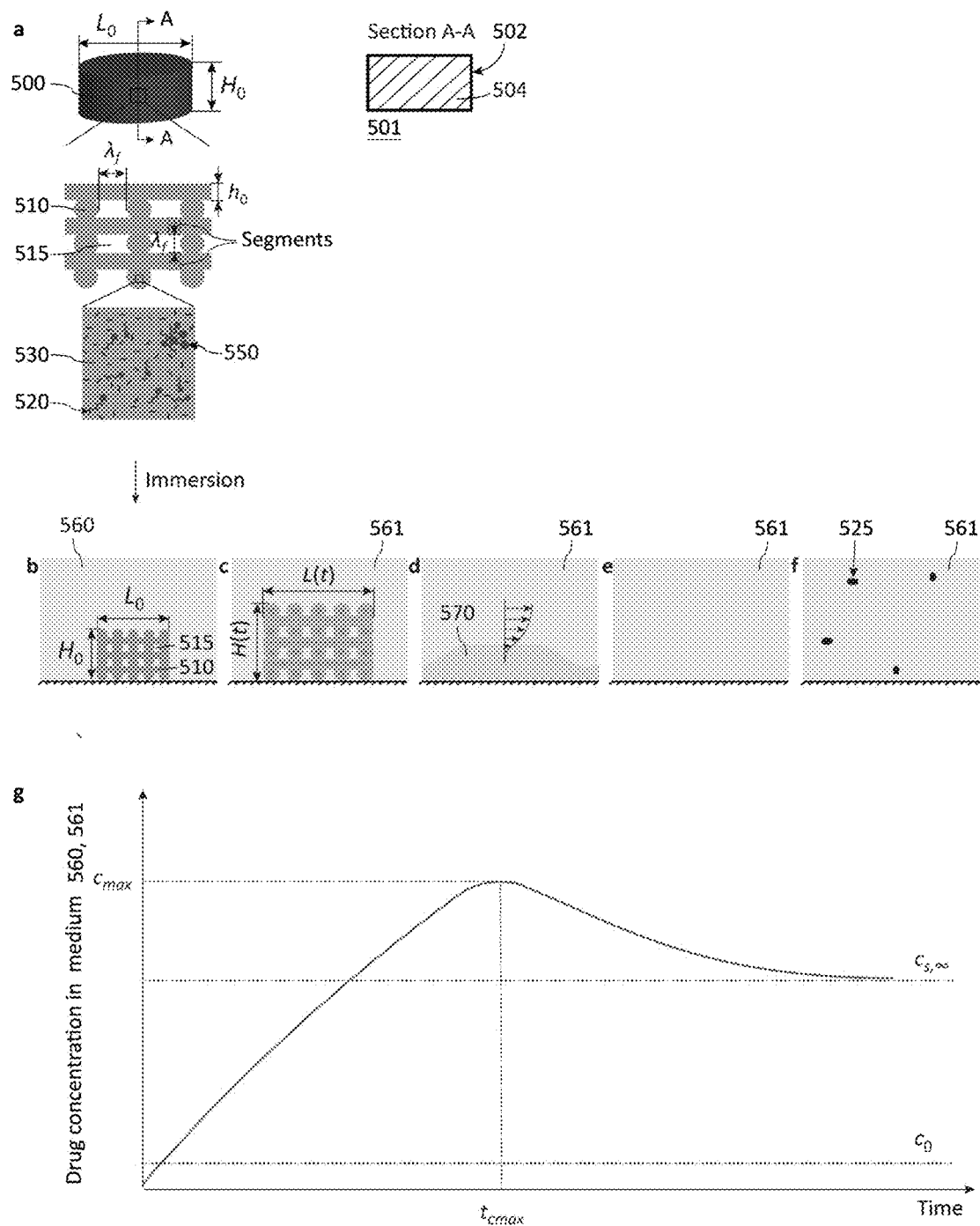
FIG. 5 presents (a) a non-limiting schematic of a fibrous dosage form according to the invention herein, (b)-(f) the evolution of its macro-, and microstructure after immersion in a dissolution fluid, and (g) the evolution of drug concentration in said dissolution fluid.

(b) Dosage Form Disintegration and Evolution of Drug Concentration in a Dissolution Fluid (b1) Microstructural Design FIG. 5 presents a non-limiting example of a pharmaceutical dosage form 500 comprising a drug-containing solid 501 having an outer surface 502 and an internal three dimensional structural framework 504 of one or more substantially orderly arranged structural elements 510. The framework 504 is contiguous with and terminates at said outer surface 502. The structural elements 510 comprise fibers 510 stacked layer-by-layer in a cross-ply arrangement (e.g., criss-crossed stacked layers of fibers). The fibers 510 comprise segments spaced apart from segments of adjoining fibers (or segments) 510, thereby defining free spaces 515. A plurality of adjacent free spaces 515 combine to define one or more interconnected free spaces 515 forming an open pore network that extends over the length, width, and thickness of the drug-containing solid 501. The structural elements 510 further comprise at least one sparingly-soluble active ingredient (e.g., at least one sparingly soluble drug) dissolved as drug molecules 520 or dispersed as nanometer-scale aggregates in an excipient matrix 530, 550. Thus the drug forms a solid solution or a solid dispersion with said excipient matrix 530, 550. The excipient matrix 530, 550 comprises at least a water-soluble polymer 530 to carry the sparingly-soluble drug molecules 520 or aggregates in the three dimensional structural framework of elements 510. The excipient matrix 530, 550 further comprises at least an amphiphilic polymer 550 for enhancing drug solubility in aqueous solutions.

(b2) Percolation of Dissolution Fluid into the Dosage Form

Without wishing to be bound to a particular theory, it is believed that a gas-filled free space 515, channel, network of channels, or open pore network is percolated rapidly by a dissolution fluid if (a) at least two (open) ends of said gas-filled free space 515, channel, network of channels, or open pore network are in contact (e.g., in direct contact) with said dissolution fluid 560, 561, (b) the surface of said gas-filled free space 515, channel, network of channels, or open pore network is hydrophilic or highly hydrophilic, and (c) the channel width (e.g., the channel diameter, or the width of the free space, or the width or diameter of the pores in the open pore network) is at the micro- or macro-scale. In the invention herein, a channel width or diameter is understood as "at the micro- or macro-scale" if it is greater than 1 µm. This includes but is not limited to a channel width or diameter greater than 2 µm, or greater than 5 µm, or greater than 7 µm, or greater than 10 µm, or greater than 15 µm, or greater than 20 µm, or greater than 25 µm, or greater than 30 µm.

(b3) Diffusion of Dissolution Fluid into the Fibrous Structural Elements and Expansion After percolation, dissolution fluid (e.g., water) partially or entirely wets (e.g., is in direct contact with) the three dimensional structural framework of elements. Then the dissolution fluid and the fibers interdiffuse and the structure may expand. The derivation of an exact solution for the expansion of the three dimensional fibrous framework is a complex problem. Herein, therefore, rough predictions of dosage form expansion are made based on the expansion of a single fiber.

To our knowledge, even for the single fiber a simple analytical solution of the coupled diffusion-expansion problem is not available at present. An order of magnitude estimate may, however, be obtained if the water concentration in the fiber and the expansion are assumed small. For small times the ratio of the mass of water in the fiber at time t, $M_w(t)$ and that at "infinite" time, $M_{w,\infty}$, may then be estimated as (see, e.g., J. Crank, "The Mathematics of Diffusion", second edition, Oxford University Press, 1975):

$$\frac{M_W(c)}{M_{W,\infty}} \cong \frac{4}{\sqrt{\pi}}\left(\frac{D_W t}{R_0^2}\right)^{1/2} \tag{1}$$

where $D_w$ is the water diffusivity in the fiber and $R_0$ the fiber radius. The mass and volume of water in the fiber may be related by:

$$M_w(t) = \rho_w V_w(t) \tag{2a}$$

where $\rho_w$ is the water density and $V_w$ the water volume in the fiber. Also, for small expansions.

$$M_{w,\infty} = c_b V_0 \tag{2b}$$

where $c_b$ is the boundary concentration of water and $V_0$ the initial fiber volume.

Substituting Eqs. (2a) and (2b) in Eq. (1) and rearranging gives:

$$\frac{V_w(t)}{V_0} = \frac{4}{\sqrt{\pi}} \frac{c_b}{\rho_w}\left(\frac{D_w t}{R_0^2}\right)^{1/2} \tag{3}$$

where $V_w(t)/V_0 = \Delta V/V_0$ is the normalized volumetric expansion (volumetric strain) of the fiber.

Thus, for isotropic expansion the normalized radial and longitudinal expansions may be estimated by:

$$\frac{\Delta R}{R_0} \cong \frac{\Delta L}{L_0} \cong \frac{4}{3\sqrt{\pi}}\left(\frac{D_w t}{R_0^2}\right)^{1/2} \tag{4}$$

By way of example but not by way of limitation, if $c_b \sim 930$ mg/ml, $\rho_w = 1000$ kg/m³, $D_w \sim 2.7 \times 10^{-11}$ m²/s, and $R_0 \sim 100$ µm, the calculated normalized radial and longitudinal expansions of the single fiber after two minutes, $\Delta R_2/R_0 \sim \Delta L_2/L_0 \sim 0.4$.

Figure 6:
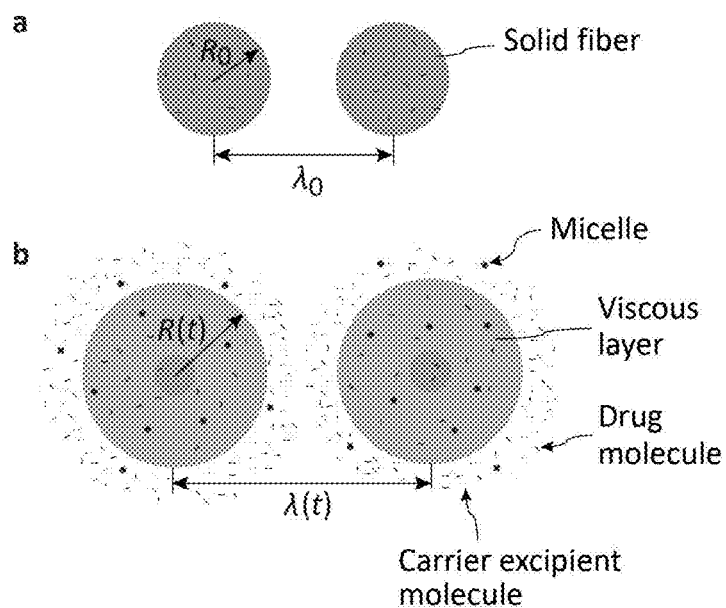
FIG. 6 schematically illustrates expansion of fibrous dosage forms: (a) front view of two fibers in a layer initially, and (b) front view of two fibers in a layer at time t after immersion in a dissolution fluid.

Further, as shown schematically in the non-limiting FIG. 6, in dosage forms with isotropically expanding fibers the void space may remain contiguous (i.e., the fibers may not coalesce) during water absorption, and the dissolution fluid may continue to percolate through and diffuse into the fiber. The radial and axial expansions of the fibers in the dosage form may then be about the same as that of the single fiber.

(b4) Formation of a Viscous Medium

Figure 7:
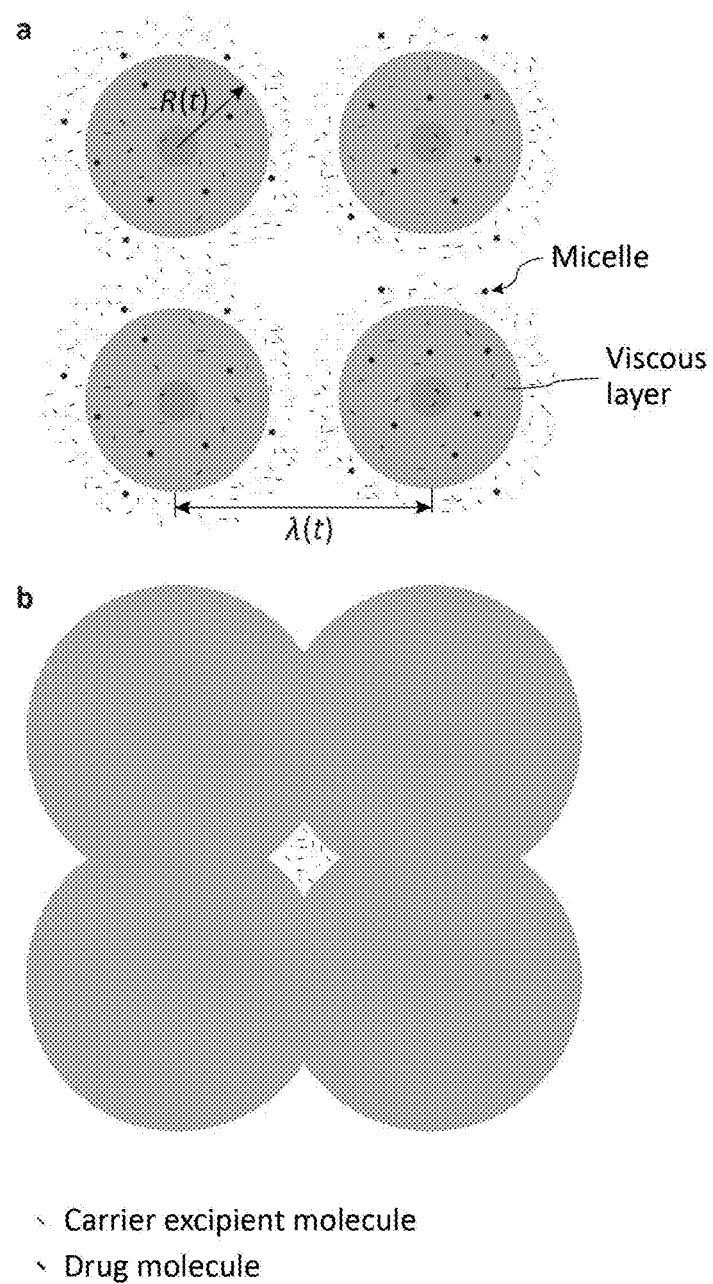
FIG. 7 schematically illustrates formation of a viscous medium: (a) microstructure at time $t < t_v$, the time to form a viscous medium and (b) microstructure at time $t \geq t_v$.

Eventually, however, the entire (or a large fraction of) the fibrous framework may have transitioned to viscous, and the surface layers of neighboring fibers may coalesce forming a viscous medium, FIG. 7. The time to form a viscous medium is about:

$$t_v \sim \frac{R_0^2}{D_w} \tag{5}$$

Eq. (5) shows that the thinner the one or more elements, the faster water penetrates to the center. Also, the greater the diffusivity of water, the shorter is the penetration time. Thus, thin elements in which the diffusivity of water is large are rapidly penetrated and transition to viscous. For the non-limiting parameter values $R_0 \sim 100$ µm and $D_w \sim 2.7 \times 10^{-11}$ m²/s, $t_v \sim 6$ min.

The viscosity of the viscous medium depends on the concentration, $c_{pe,v}$, of the predominant water-soluble excipient (typically the excipient with greatest molecular weight):

$$c_{pe,v} = \frac{M_{pe,v}}{V_v} \tag{i}$$

where $M_{pe,v}$ is the mass of the predominant water-soluble excipient in the viscous medium (or dosage form) and $V_v$ the volume of the viscous medium.

The mass of predominant water-soluble excipient in the viscous medium may be approximated, roughly, by:

$$M_{pe,v} = w_{pe} \rho_s \phi_s V_{sdf} \tag{7}$$

where $w_{pe}$ is the weight fraction of the predominant water-soluble excipient in the dry solid dosage form, $\rho_s$ the density of the solid fibers, $\phi_s$ the volume fraction of the solid fibers, and $V_{sdf}$ the nominal volume of the dry solid dosage form.

Similarly, for "small", isotropic expansions the volume of the viscous medium may be written, roughly, as:

$$V_v = V_{sdf}(1 + 3\Delta L_v/L_0) \tag{8}$$

where $\Delta L_v = L_v - L_0$; $L_v$ is the side length of the viscous medium and $L_0$ the initial length of the solid dosage form.

Substituting Eqs. (7) and (8) in Eq. (6), $$c_{pe,v} = \frac{w_{pe}\phi_s}{1 + 3\Delta L_v/L_0}\rho_s \quad (9)$$

Thus the concentration and viscosity of the viscous medium increase with the weight fraction of water-soluble excipient in the fibers and the volume fraction of fibers in the solid dosage form. The concentration and viscosity of the viscous medium decrease with increasing $\Delta L_v/L_0$ or normalized expansion of the dosage form.

Shown below are the calculated values of $c_{pe,v}$ and the corresponding viscosities, $\mu_v$, of the viscous media for the non-limiting experimental dosage forms presented later in section "EXPERIMENTAL EXAMPLES". The viscosities of the media were 50 to 6100 times that of water.

| Dosage form | $c_{pe,v}$ (mg/ml) | $\mu_v$ (Pa · s) |
|---|---|---|
| A | 77 | 0.05 |
| B | 167 | 1.2 |
| C | 250 | 6.1 |

$c_{pe,v}$ is calculated by Eq. (9) substituting $w_{pe} = 0.6$, $\rho_s = 1200$, and $\phi_s$ and $\Delta L_v/L_0 \approx \Delta L_2/L_0$ from Table 4 later.
$\mu_v$ is obtained from the viscosity-concentration data of FIG. 43.

(b5) Deformation of the Viscous Medium

Because the viscous media are subjected to shear stresses due to fluid flow, gravity, and so on, they deform with time. For simple shear a rough estimate of the deformation time (e.g, the time to deform the viscous medium to a thin sheet, or the time to "break" the viscous medium apart) is:

$$t_{def} \sim \frac{\mu_v}{\tau} \quad (10)$$

where $\tau$ is the shear stress acting on the surface of the viscous medium. Using the non-limiting value $\tau \sim 2.6 \times 10^{-3}$ Pa·s and the viscosities of the experimental dosage forms above, the calculated deformation time of the non-limiting experimental dosage forms A, B, and C, respectively, are 0.3, 8, and 39 min.

(b6) Erosion of the Viscous Medium by Convective Mass Transfer

Concomitant with the viscous deformation, the excipient and the drug in the viscous medium inter-diffuse with the dissolution fluid. The erosion rate by convective diffusion may be estimated from that of a rotating, solid disk as:

$$E = 0.62\left(\frac{c_{pe}^*}{c_{pe,v}}\right)\left(\frac{\mu_f}{D_{pe}\rho_f}\right)^{1/3}\left(\frac{D_{pe}^2\rho_f\Omega}{\mu_f}\right)^{1/2} \quad (11)$$

where $c_{pe}^*$ is the disentanglement concentration and $D_{pe}$ the diffusivity of the predominant water-soluble excipient, $\mu_f$ is the viscosity of the dissolution fluid, and $\Omega$ the rotation rate of the paddle (or stirrer or rotating disk).

The time to erode a viscous medium of initial thickness, $H_v$, by convective diffusion alone (without any deformation) may be estimated as:

$$t_{er} = \frac{H_v}{E} \quad (12)$$

Using the non-limiting parameters for $c_{pe,v}$ above and $c_{pe}^* \sim 66$ kg/m$^3$, $\mu_f \sim 0.001$ Pa·s, $D_{pe} \sim 1.5 \times 10^{-10}$ m$^2$/s, $\rho_f \sim 1000$ kg/m$^3$, $\Omega \sim 5.24$ rad/s, and $H_v \sim 3.6$ mm, $t_{er} \sim 18$, 38, and 57 minutes for dosage forms A, B, and C, respectively.

(b7) Dissolution Time of Dosage Forms

Because percolation and viscous mass formation are serial processes, and viscous deformation and erosion are parallel processes, the dosage form dissolution time may be expressed, roughly, as:

$$t_d = t_{perc} + t_v + \frac{t_{def}t_{er}}{t_{def} + t_{er}} \quad (13)$$

where $t_v$, $t_{def}$, and $t_{er}$ may be obtained from Eqs. (3), (8), (16), and (18). The percolation time, $t_{perc}$, is generally much smaller than the dissolution time, and thus may be assumed equal to zero. Inserting the relevant values of the non-limiting experimental dosage forms A, B, and C, respectively, $t_d$=6, 12, and 29 minutes.

(b8) Drug Concentration Versus Time in a Small Volume of Dissolution Fluid

Drug is released as the dosage form or viscous medium erodes. Initially, as mentioned above, the drug is dispersed as molecules in the drug-excipient framework. In the viscous drug-excipient-water medium, however, the mobility of drug molecules will be greater and the drug solubility smaller than in the solid structure. Thus, drug particles may nucleate and grow.

If the precipitation rate within the viscous medium is slower than the drug release rate from the medium into the dissolution fluid, virtually all drug may be released as molecules. The drug concentration in the dissolution fluid, ca, then increases rapidly and the dissolution fluid may supersaturate. Past the maximum supersaturation, however, drug particles may precipitate in the dissolution fluid. As a result, the drug concentration may decrease and eventually approach the terminal solubility, $c_{s,\infty}$.

The drug solubility in the terminal dissolution fluid is affected by the concentration of excipient. A heuristic estimation of the solubility may be written as:

$$c_{s,\infty} = ac_{e,\infty} + c_0 \quad (14)$$

where a is the slope of drug solubility versus excipient concentration, $c_{e,\infty}$ the excipient concentration in the terminal dissolution fluid, and co the solubility of ibuprofen in water with 0.1 M HCl (no excipient).

Substituting the excipient concentration $$c_{e,\infty} = \frac{M_e}{V_{fluid}} = \frac{\phi_s w_e \rho_s V_{sdf}}{V_{fluid}} \quad (15)$$

the solubility may be expressed as:

$$c_{s,\infty} = a\frac{\phi_s w_e \rho_s V_{sdf}}{V_{fluid}} + c_0 \quad (16)$$

where $M_e$ is the mass of water-soluble (or solubility-enhancing) excipient in the dosage form, $V_{fluid}$ the volume of the dissolution fluid, $w_e$ the weight fraction of water-soluble (or solubility-enhancing) excipient in the dosage form, $\rho_s$ the solid fiber density, and $V_{sdf}$ the volume of the solid dosage form.

A significant increase in drug solubility may be effected by a large amount of water-soluble (or amphiphilic or solubility-enhancing) excipient. Thus, dense packing of solid-solution fibers with large content or weight fraction of solubility-enhancing excipient is desirable for maximizing solubility in a dissolution fluid.

(c) Nano-Scale Considerations

Fiber packing even up to fairly large fiber volume fractions (e.g., greater than 0.5) does not significantly lessen the dissolution rate of the disclosed dosage form if the fibers expand isotropically, forming a low-viscosity medium that deforms and dissolves rapidly. Thus, rapid expansion of the structure upon immersion is crucial for achieving fast dissolution of densely-packed solid-solution structures. The following considerations at the nano-scale show how isotropic expansion of fibers and fibrous dosage forms (or any dosage form disclosed herein) may be promoted.

Figure 8:
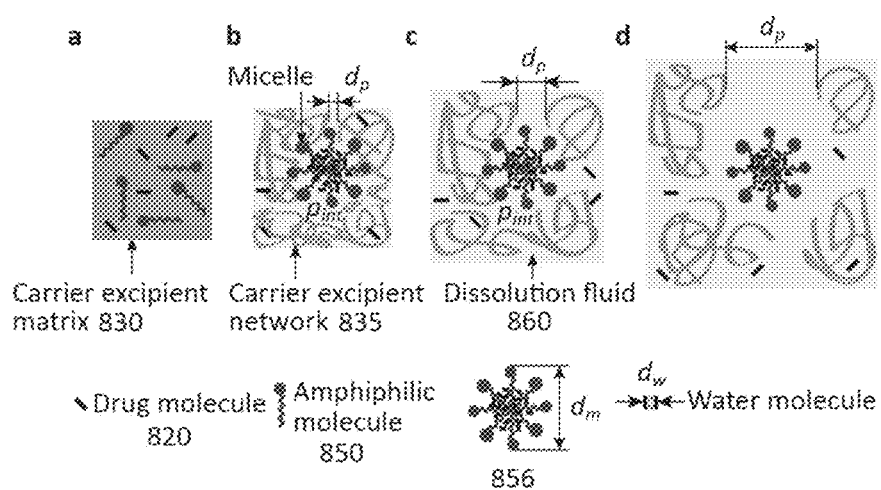
FIG. 8 presents idealized schematics of the molecular structure of an expanding polymeric element: (a) initial structure, (b) formation of cells after exposure to water, (c) cell expansion at larger times, and (d) at time so large that the pore size, $d_p$, in the cellular network is greater than the diameter, $d_m$, of the micelles.

As illustrated schematically in FIG. 8a, initially the nano-structure of the fibers comprises a solid solution of dispersed drug molecules 820 and amphiphilic excipient molecules 850 in a matrix of the carrier excipient 830. As dissolution fluid 860 (water) diffuses into the fiber, the initial solid structure transitions to an aqueous, viscous medium, FIG. 8b. In the viscous medium the amphiphilic excipient molecules 850 assemble as micelles 856 and the drug molecules 820 accumulate in the micelle core. The carrier excipient molecules 835 may form a flexible, cellular network enclosing the micelles 856.

The "opening size" in the cell walls, $d_{cw}$, of the cellular carrier excipient network 835 may be greater than the size of water molecules, $d_w$, but smaller than the diameter, $d_m$, of the micelles 856. Thus, water molecules may pass through the network into the cell, but passage of the micelles 856 out of the cells may be hindered. As a result, an internal pressure, $p_{int}$, may develop in the cells due to the inward diffusive, or osmotic, flux of water. The internal pressure may cause the cells, the fibers, and the dosage form to expand isotropically, as shown schematically in FIG. 8c.

Eventually, as shown in FIG. 8d, the carrier excipient network 835 may have expanded so much that $d_{cw}$ is greater than $d_m$. Thus, the micelles 856 may then diffuse out of the cellular network 835. The internal pressure may be relieved and the cellular excipient network may not expand any further.

Thus, provided the fiber structure is isotropic, the osmotic pressure in the fibers may promote isotropic expansion. The amphiphilic excipient 850 may have the following dual function: increasing drug solubility by entrapping drug molecules in micelles, and promoting isotropic fiber expansion for faster dissolution of densely-packed drug-excipient frameworks.

d) Embodiments of Micro- and Nanostructural Designs

The following non-limiting embodiments provide examples to illustrate effects of macro-, micro- and nano-structural design of the dosage forms on dosage form disintegration/dissolution, drug release, and drug concentration in a dissolution fluid versus time.

Figure 9:
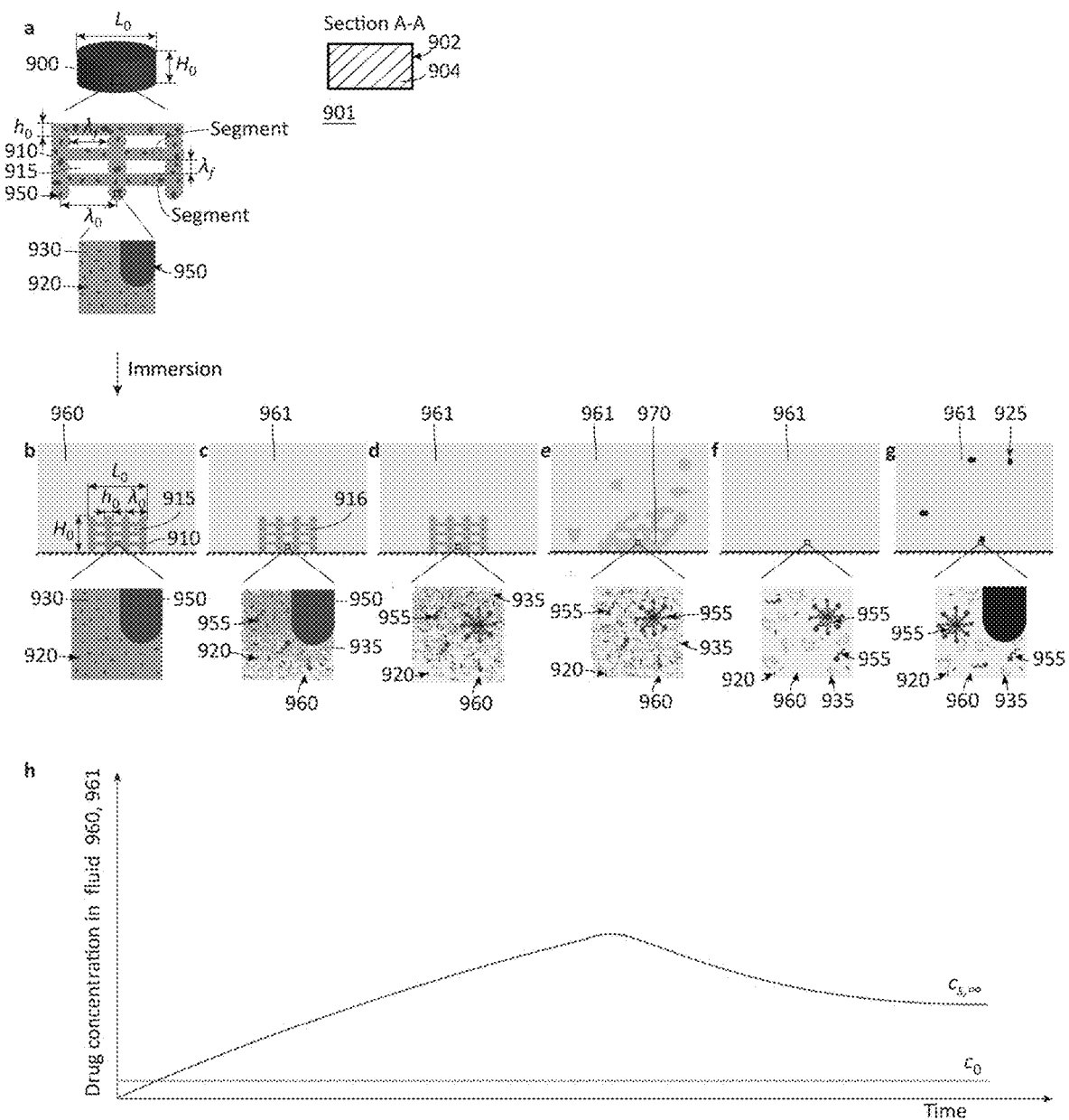
FIG. 9 shows (a) a non-limiting schematic of a dosage form comprising dispersed, large particles of amphiphilic excipient in a loosely-packed structural framework, (b)-(g) the evolution of its macro-, micro-, and nano-structure after immersion in a dissolution fluid, and (h) the evolution of drug concentration in said dissolution fluid.

FIG. 9a shows a non-limiting pharmaceutical dosage form 900 comprising a drug-containing solid 901 having an outer surface 902 and an internal three dimensional structural framework 904 of one or more criss-crossed stacked layers of fibrous structural elements 910 that are spaced fairly far apart. Said framework 904 is contiguous with and terminates at said outer surface 901. Said fibrous structural elements 910 comprise segments spaced apart from adjoining segments, thereby defining free spaces 915, wherein a plurality of adjacent free spaces combine to define an interconnected free space 915 forming an open pore network 915 that is contiguous with (e.g., in direct contact with or connected to) the outer surface 902 and extends over the length, width, and thickness of the drug-containing solid 901. The fibrous structural elements 910 further comprise at least one sparingly-soluble active ingredient (e.g., at least one sparingly soluble drug) 920 dissolved (e.g., molecularly dispersed) in an amorphous, water-soluble polymeric carrier 930 to form a solid solution with said polymeric excipient 930. The weight fraction of dissolved sparingly-soluble drug is so that the drug supersaturates in the fibrous structural elements 910 upon contact with water. The composition of the fibrous structural elements 910 further comprises at least an amphiphilic excipient 950 for enhancing drug solubility in aqueous solutions. Said amphiphilic excipient 950 is dispersed as particles in the fibrous structural elements 950. The particle size is greater than about 10-50 µm.

As shown schematically in the non-limiting FIG. 9b, upon immersion in a dissolution fluid 960 the fluid 960 percolates rapidly into the open pore network 915. The fluid 960, 961 then diffuses into the fibrous structural elements 910 and drug molecules 920 and amorphous, water-soluble polymeric excipient molecules 935, diffuse out into the dissolution fluid 960, 961 or fluid-filled void spaces 916 (FIG. 9c). A diffuse layer of excipient molecules 935, drug molecules 920, and dissolution fluid 960 is formed at the fiber-fluid interface. The layer grows inwards and outwards as shown in FIG. 9d. Also, as the water content in the fiber increases the amphiphilic excipient particles 950 dissolve (FIGS. 9c and 9d). The dissolved amphiphilic excipient molecules 955 self-assemble to form micelles 956. However, because the size of amphiphilic particles is fairly large, they dissolve slowly. Thus, initially the concentration of solubility-enhancing micelles is fairly small. The drug in the fibers supersaturates, accordingly, and drug particles nucleate and grow.

Eventually, as shown in the non-limiting FIG. 9e, a viscous solution or dispersion 970 is formed. Because the concentration of water-soluble carrier 930, 935 in the solution 970 is fairly small (water content in the solution 970 is very large), its viscosity is small. Thus the solution 970 deforms and dissolves rapidly in the dissolution fluid 961, thereby releasing drug molecules 920, excipient molecules 935, 955 and drug-excipient micelles 956 into the dissolution fluid 961. After dissolution of the solution 970, as shown in the non-limiting FIG. 9e a homogenous solution 961 of drug molecules 920, excipient molecules 935, 955, and drug-excipient micelles 956 may be formed. If the drug concentration in the solution 961 is greater than the solubility, however, drug particles 925 may precipitate (e.g., nucleate, and/or grow, and/or coalesce) until terminal solubility is reached (FIG. 9f).

FIG. 9g presents a schematic of drug concentration (e.g., the concentration of drug molecules) in said dissolution fluid 960, 961 of small volume versus time after immersion of said non-limiting dosage form 900. The dosage form releases drug faster than particles precipitate in the viscous solution, thus the dissolution fluid supersaturates. Moreover, the amphiphilic, solubility-enhancing excipient enhances the terminal solubility. Because particles precipitate in the fibers, however, and the fibers are spaced fairly far apart, which limits the mass of amphiphilic excipient in the dosage form, the drug concentration increase (e.g., the increase of drug release rate, supersaturation, and terminal solubility) is limited.

Figure 10:
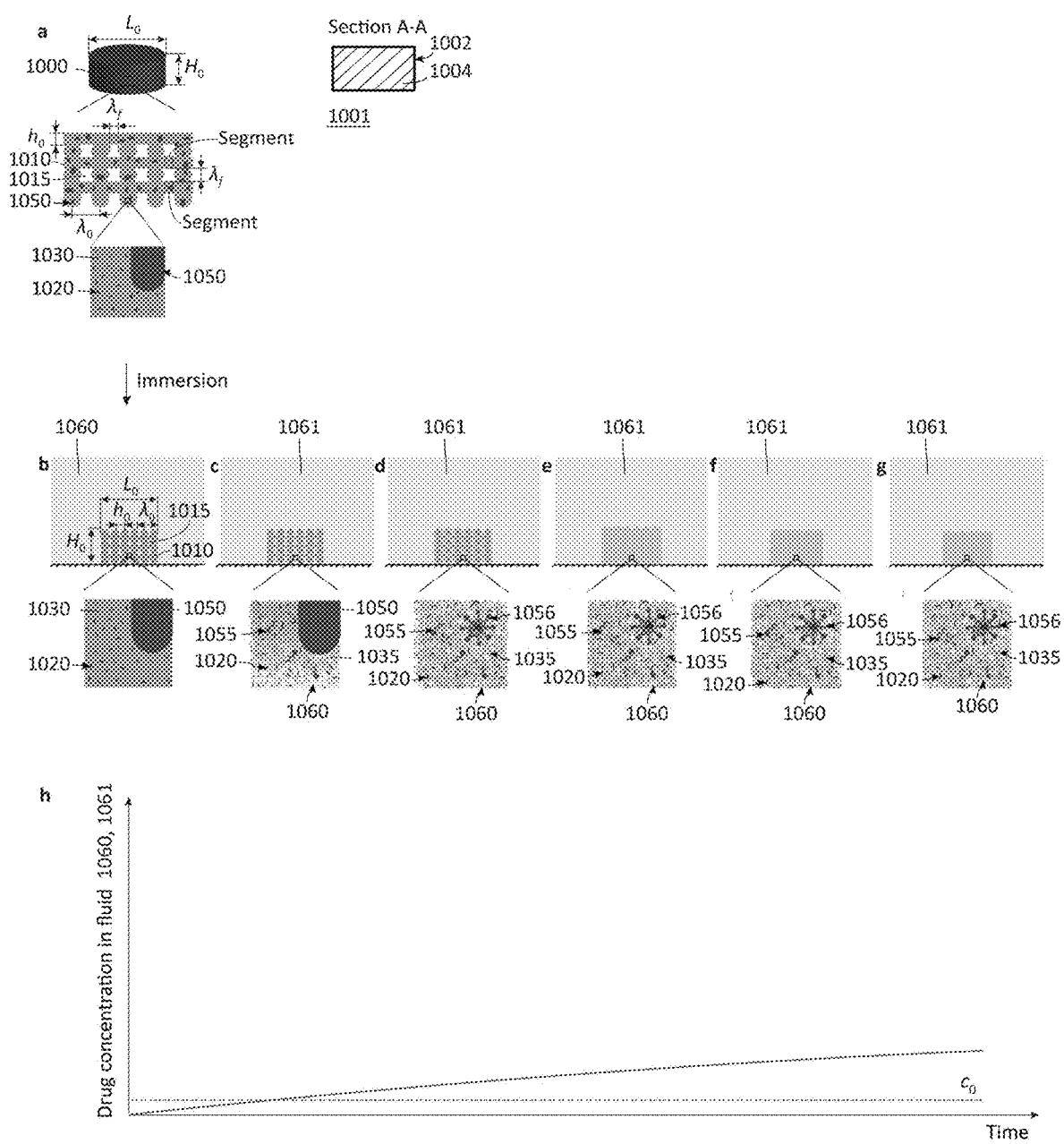
FIG. 10 shows (a) a non-limiting schematic of a dosage form comprising dispersed, large particles of amphiphilic excipient in a densely-packed structural framework, (b)-(g) the evolution of its macro-, micro-, and nano-structure after immersion in a dissolution fluid, and (h) the evolution of drug concentration in said dissolution fluid.

FIG. 10a shows another non-limiting pharmaceutical dosage form 1000 comprising a drug-containing solid 1001 having an outer surface 1002 and an internal three dimensional structural framework 1004 of one or more criss-crossed stacked layers of fibrous structural elements 1010 that are more closely-packed. Said framework 1004 is contiguous with and terminates at said outer surface 1001. Said fibrous structural elements 1010 comprise segments spaced apart from adjoining segments, thereby defining free spaces 1015, wherein a plurality of adjacent free spaces combine to define an interconnected free space 1015 forming an open pore network 1015 that is contiguous with (e.g., in direct contact with or connected to) the outer surface 1002 and extends over the length, width, and thickness of the drug-containing solid 1001. The fibrous structural elements 1010 further comprise at least one sparingly-soluble active ingredient (e.g., at least one sparingly soluble drug) 1020 dissolved (e.g., molecularly dispersed) in an amorphous, water-soluble polymeric excipient 1030 to form a solid solution with said polymeric excipient 1030. The weight fraction of dissolved sparingly-soluble drug is so that the drug supersaturates in the fibrous structural elements 1010 upon contact with water. The composition of the fibrous structural elements 1010 further comprises at least an amphiphilic excipient 1050 for enhancing drug solubility in aqueous solutions. Said amphiphilic excipient 1050 is dispersed as particles in the fibrous structural elements 1050. The particle size is greater than about 10-50 µm.

As shown schematically in the non-limiting FIG. 10b, upon immersion in a dissolution fluid 1060 the fluid 1060 percolates rapidly into the open pore network 1015. The fluid 1060, 1061 then diffuses into the fibrous structural elements 1010 and drug molecules 1020 and amorphous, water-soluble polymeric excipient molecules 1035, diffuse out (FIG. 10c). A diffuse layer of excipient molecules 1035, drug molecules 1020, and dissolution fluid 1060 is formed at the fiber-fluid interface. The layer grows inwards and outwards as shown in FIG. 10d. Also, as the water content in the fiber increases the amphiphilic excipient particles 1050 dissolve (FIGS. 10c and 10d). The dissolved amphiphilic excipient molecules 1055 self-assemble to form micelles 1056. However, because the size of amphiphilic particles is fairly large, they dissolve slowly. Thus, initially the concentration of solubility-enhancing micelles is fairly small. The drug in the fibers supersaturates, accordingly, and drug particles nucleate and grow. Moreover, because the fibers are closely-packed, they coalesce as water diffuses in, forming a high-viscosity gel. The gel dissolves slowly, and slowly releases drug, water-soluble carrier, and solubility-enhancing excipient.

FIG. 10g presents a schematic of drug concentration (e.g., the concentration of drug molecules) in said dissolution fluid 1060, 1061 of small volume versus time after immersion of said non-limiting dosage form 1000. Because the drug release rate is compromised the drug concentration raises slowly. The dissolution fluid may not supersaturate.

The trade-off between fast dosage form disintegration (or dissolution) and dense packing of solid-solution fibers (e.g., fibers with large content of water-soluble carrier) may be overcome, however, if the dosage form expands (e.g., expands isotropically) while transitioning to a viscous medium.

Figure 11:
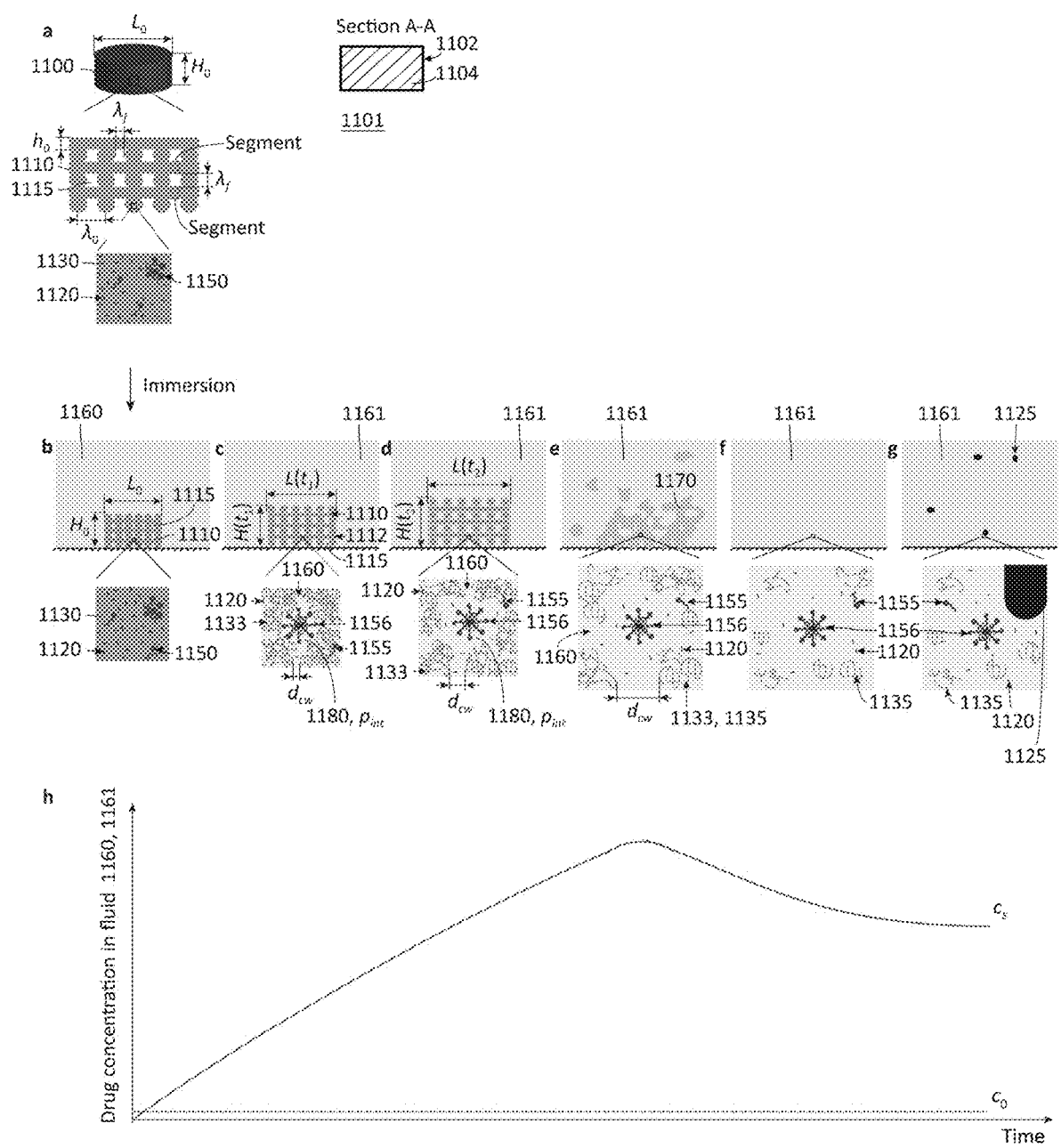
FIG. 11 shows (a) a non-limiting schematic of a dosage form comprising dissolved molecules or dispersed nanometer-scale aggregates of amphiphilic excipient in a densely-packed structural framework, (b)-(g) the evolution of its macro-, micro-, and nano-structure after immersion in a dissolution fluid, and (h) the evolution of drug concentration in said dissolution fluid.

Thus, FIG. 11a schematically shows another non-limiting pharmaceutical dosage form 1100 comprising a drug-containing solid 1101 having an outer surface 1102 and an internal three dimensional structural framework 1104 of one or more criss-crossed stacked layers of fibrous structural elements 1110 that are closely-packed. Said framework 1104 is contiguous with and terminates at said outer surface 1101. Said fibrous structural elements 1110 comprise segments spaced apart from adjoining segments, thereby defining free spaces 1115, wherein a plurality of adjacent free spaces combine to define an interconnected free space 1115 forming an open pore network 1115 that is contiguous with (e.g., in direct contact with or connected to) the outer surface 1102 and extends over the length, width, and thickness of the drug-containing solid 1101. The fibrous structural elements 1110 further comprise at least one sparingly-soluble active ingredient (e.g., at least one sparingly soluble drug) 1120 dissolved (e.g., molecularly dispersed) in an amorphous, water-soluble polymeric excipient 1130 to form a solid solution with said polymeric excipient 1130. The weight fraction of dissolved sparingly-soluble drug is so that the drug supersaturates in the fibrous structural elements 1110 upon contact with water. The composition of the fibrous structural elements 1110 further comprises at least an amphiphilic excipient 1150 for enhancing drug solubility in aqueous solutions. Said amphiphilic excipient 1150 is dissolved as molecules or dispersed as nanometer-scale aggregates (or dispersed as particles with size smaller than about 10-50 µm) in the fibrous structural elements 1150. The concentration of said amphiphilic excipient 1150 is uniform across the structural framework 1104.

As shown schematically in the non-limiting FIG. 11b, upon immersion in a dissolution fluid 1160 the fluid 1160 percolates rapidly into the open pore network 1115. The fluid 1160 then diffuses into the initial solid structure 1110, and the structure 910 transitions to an aqueous, viscous medium 1112 from the surface inwards (FIG. 11c). In the viscous medium 1112 the amphiphilic excipient particles or aggregates rapidly dissolve, resulting in a large and fairly uniform concentration of amphiphilic excipient molecules 1155 across the framework. The amphiphilic excipient molecules 1155 assemble as micelles 1156 and the drug molecules 1120 accumulate in the micelle 1156 core. As a result, drug solubility in the viscous medium 1112 is enhanced and drug particle precipitation is mitigated.

Moreover, the carrier excipient 1130 forms a flexible, cellular network 1133 enclosing the micelles 1156. The opening size in the walls of the cellular network 1133, $d_{cw}$, is greater than the size of water molecules, $d_w$, but smaller than the diameter, $d_m$, of the micelles 1156. Thus, water molecules can pass through the network 1133 into the cell 980, but passage of the micelles 1156 out of the cells 1180 is hindered. As a result, an internal pressure, $p_{int}$, develops in the cells 1180 due to the inward diffusive, or osmotic, flux of water. The internal pressure causes the cell walls 1133 to expand as shown schematically in FIG. 11d. Moreover, the internal pressure promotes isotropic expansion of fibers 1110, 1112 in both radial and longitudinal direction. Consequently, the free spaces 1115 remain open, dissolution fluid 1160, 1161 can continue to flow in, and dilute the dosage form.

Eventually, as shown in FIG. 11e, the carrier excipient network 1133 has expanded so much that $d_{cw}$ is greater than $d_m$. Thus, the micelles 1156 can then diffuse out of the cells 1180. The membrane effect is lost.

A viscous solution 1170 may then be formed. Because the concentration of water-soluble excipient molecules 1135 in the solution 1170 is fairly small (water content in the solution 1170 is very large), its viscosity is small. Thus the solution 1170 deforms and dissolves rapidly in the dissolution fluid 1161, thereby releasing drug molecules 1120, excipient molecules 1135, 1155 and drug-excipient micelles 1156 into the dissolution fluid 1161. After dissolution of the solution 1170, as shown in the non-limiting FIG. 11e a homogeneous solution 1161 of drug molecules 1120, excipient molecules 1135, 1155, and drug-excipient micelles 1156 may be formed. If the drug concentration in the solution 1161 is greater than the solubility, however, drug particles 1125 may precipitate (e.g., nucleate, and/or grow, and/or coalesce) until terminal solubility is reached (FIG. 11f).

Thus, provided the fiber structure is isotropic, the osmotic pressure in the fibers promotes isotropic expansion. The uniformly distributed amphiphilic excipient molecules (or small aggregates) have the following dual function: increasing drug solubility by entrapping drug molecules in micelles, and promoting isotropic expansion of fibers for faster dissolution of densely-packed drug-excipient fibrous frameworks.

FIG. 11g presents a non-limiting schematic of drug concentration (e.g., concentration of drug molecules) in said dissolution fluid 1160, 1161 of small volume versus time after immersion of said non-limiting dosage form 1100. The dosage form 1100 releases drug faster than particles precipitate in the viscous solution, thus the dissolution fluid supersaturates. Because particle precipitation in the fibers and the viscous medium is mitigated, and the fiber spacing is tight (which maximizes the mass of amphiphilic excipient in the dosage form), the drug concentration increase (e.g., the increase of drug release rate, supersaturation, and terminal solubility) may be maximized.

Embodiments of the Dosage Form

In view of the design considerations, theoretical models and non-limiting examples above, which are suggestive and approximate rather than exact, the dosage forms disclosed herein may further comprise the following embodiments.

a) Surface Composition of Elements and Segments

In some embodiments, for enabling rapid percolation of dissolution fluid into the interior of the dosage form structure (e.g., into the free spaces of the drug-containing solid), the surface composition of at least one element is hydrophilic. Such embodiments include, but are not limited to embodiments where the surface composition of one or more structural elements and/or the surface composition of one or more segments and/or the surface composition of the three dimensional structural framework is hydrophilic. In this disclosure, a surface or surface composition is hydrophilic, also referred to as "wettable by a physiological fluid", if the contact angle of a droplet of physiological fluid on said surface in air is no more than 90 degrees. This includes, but is not limited to a contact angle of a droplet of said fluid on said solid surface in air no more than 80 degrees, or no more than 70 degrees, or no more than 60 degrees, or no more than 50 degrees, or no more than 40 degrees, or no more than 30 degrees. It may be noted that in some embodiments the contact angle may not be stationary. In this case, a solid surface may be understood "hydrophilic" if the contact angle of a droplet of physiological fluid on said solid surface in air is no more than 90 degrees (including but not limiting to no more than 80 degrees, or no more than 70 degrees, or no more than 60 degrees, or no more than 50 degrees, or no more than 40 degrees) at least 20-360 seconds after the droplet has been deposited on said surface. A non-limiting illustration of a droplet on a surface is presented in U.S. application Ser. No. 15/482,776 titled "Fibrous dosage form".

Generally, the percolation rate of physiological fluid into the interconnected free spaces is increased if the contact angle between said fluid and the surface of the three dimensional structural framework of one or more elements is decreased. Thus, in some embodiments, at least one element or at least one segment of an element or the three dimensional structural framework of elements comprises a hydrophilic or highly hydrophilic coating for enhancing the rate of fluid percolation into the dosage form structure. In the context herein, a solid surface (e.g., a solid material or a solid compound or a surface or a coating) is understood "highly hydrophilic" if the contact angle of a droplet of physiological fluid on the surface of said solid in air is no more is no more than 45 degrees. This includes, but is not limited to a contact angle of a droplet of said fluid on said solid surface in air no more than 35 degrees, or no more than 30 degrees, or no more than 25 degrees, or no more than 20 degrees, or no more than 15 degrees.

Non-limiting examples of hydrophilic (or highly hydrophilic) compounds that may serve as coating of elements (or segments of elements) include polyethylene glycol, polyvinyl alcohol, polyvinyl alcohol-polyethylene glycol copolymer, polyvinyl pyrrolidone, silicon dioxide, talc, magnesium stearate, polyols (e.g., mannitol, maltitol, xylitol, maltitol, isomalt, lactitol, sucrose, glucose, erythritol, maltodextrin, etc.), and so on.

b) Geometry of Drug-Containing Solid and Three Dimensional Structural Framework

In some embodiments, moreover, dissolution fluid may only percolate into the interior of the structure (e.g., into at least one free space or into the free spaces) if the drug-containing solid comprises at least a continuous channel or free space having at least two openings in contact with said fluid. The more such channels exist with at least two ends in contact with a dissolution fluid the more uniformly may the structure be percolated. Also, the greater the space over which a continuous channel having at least two ends in contact with a dissolution fluid extends, the more uniformly may the structure be percolated. Uniform percolation generally is desirable in the invention herein.

Thus, in the invention herein a plurality of adjacent free spaces combine to define one or more interconnected free spaces (e.g., free spaces that are "contiguous" or "in direct contact" or "merged" or "without any wall in between") forming an open pore network that extends over a length at least half the thickness of the drug-containing solid. This includes, but is not limited to a plurality of adjacent free spaces combining to define one or more interconnected free spaces forming an open pore network that extends over a length at least two thirds the thickness of the drug-containing solid, or over a length at least equal to the thickness of the drug-containing solid, or over a length at least equal to the side length of the drug-containing solid, or over a length and width at least equal to half the thickness of the drug-containing solid, or over a length and width at least equal to the thickness of the drug-containing solid, or over a length, width, and thickness at least equal to half the thickness of the drug-containing solid, or over the entire length, width, and thickness of the drug-containing solid.

Moreover, in some embodiments one or more free spaces combine to form a channel having a cross section extending axially along its length from a first end to a second end. The length of said channel may be greater than half the thickness of the drug-containing solid. This includes, but is not limited to a channel having a cross section extending axially along its length from a first end to a second end and having a length at least equal to the thickness of the drug-containing solid, or at least equal to the width of the drug-containing solid, or at least equal to the length of the drug-containing solid. In some embodiments, furthermore, the channel bifurcates into at least one other end (e.g., at least two other ends or at least three other ends or at least four other ends or at least five other ends or at least six other ends), and wherein the length of the channel from the first end to one or more other ends is greater than half the thickness of the drug-containing solid. The cross section of said one or more channels may be greater than 5 μm×5 μm along the length of said one or more channels. This includes, but is not limited to a cross section of said one or more channels greater than 10 μm×10 μm along the length of said one or more channels, or a cross section of said one or more channels greater than 15 μm×15 μm along the length of said one or more channels, or a cross section of said one or more channels greater than 20 μm×20 μm along the length of said one or more channels.

Also, in some embodiments an open pore network comprises or occupies at least 30 percent (e.g., at least 40 percent, or at least 50 percent, or at least 60 percent, or at least 70 percent, or at least 80 percent, or 100 percent) of the free space of the drug-containing solid (e.g., at least 30 percent (e.g., at least 40 percent, or at least 50 percent, or at least 60 percent, or at least 70 percent, or at least 80 percent, or 100 percent) of the free space of the drug-containing solid are part of the same open pore network).

In preferred embodiments, all free spaces are interconnected forming a continuous, single open pore network. In the invention herein, if all free spaces of a drug-containing solid are interconnected the free space of said drug-containing solid is also referred to as "contiguous". In drug-containing solids with contiguous free space, no walls (e.g., walls comprising the three dimensional structural framework of elements) must be ruptured to obtain an interconnected cluster of free space (e.g., an open channel of free space) from the outer surface of the drug-containing solid to a point (or to any point) in the free space within the internal structure. The entire free space or essentially all free spaces is/are accessible from (e.g., connected to) the outer surface of the drug-containing solid.

FIG. 12a schematically illustrates a pharmaceutical dosage form 1200 comprising a drug-containing solid 1201 having an outer surface 1202 and an internal three dimensional structural framework 1204 comprising a plurality of criss-crossed stacked layers of one or more fibrous structural elements 1210. Said framework 1204 is contiguous with and terminates at said outer surface 1202. The fibrous structural elements 1210 further have segments spaced apart from segments of adjoining elements, thereby defining free spaces 1220. A plurality of adjacent free spaces 1225 combine to define one or more interconnected free spaces forming an open pore network 1230.

As shown in the non-limiting schematic of section A-A said open pore network 1230 extends over the entire length and thickness of the drug-containing solid 1201 or the dosage form 1200. In other words, the length, $L_{pore}$, over which the open pore network 1230 extends is the same as the length or diameter, D), of the dosage form 1200 or drug-containing solid 1201: the thickness, $H_{pore}$, over which the open pore network 1230 extends is the same as the thickness, H, of the dosage form 1200 or drug-containing solid 1201. It may be noted that the term "section" is understood herein as "plane" or "surface". Thus a "section" is not a "projection" or "projected view".

Moreover, in the non-limiting example of FIG. 12a the microstructure is rotationally symmetric. If the plane or section A-A is rotated by 90 degrees about the central axis the microstructure (e.g., the microstructural details) is/are the same. Thus, the open pore network 1230 also extends over the entire width of the drug-containing solid 1201 or the dosage form 1200. In other words, the width over which the open pore network 1230 extends is the same as the length or diameter. D, of the dosage form 1200 or drug-containing solid 1201.

Furthermore, in the non-limiting microstructure of FIG. 12a, as shown in section A-A the open pore network 1230 or free space 1220 or free spaces 1225 is/are contiguous. No walls (e.g., walls comprising the three dimensional structural framework 1204 of elements) must be ruptured to obtain an interconnected cluster of free spaces (e.g., an open channel of free space) from the outer surface 1202 of the drug-containing solid 1201 to a point (or to any point or position) in the free space 1220, 1225, 1230, Also, no walls (e.g., walls comprising the three dimensional structural framework 1204 of elements) must be ruptured to obtain an interconnected cluster of free space (e.g., an open channel of free space) from any point or position within the free space 1220, 1225, 1230 to any other point or position in the free space 1220, 1225, 1230, The entire free space 1220, 1225, 1230 is accessible from the outer surface 1202 of the drug-containing solid 1001. In addition, the entire free space 1220, 1225, 1230 is accessible from any point, location, or position within the free space 1220, 1225, 1230.

More examples of fibrous structures according to the invention herein would be obvious to a person of ordinary skill in the art. All of them are within the scope of this disclosure. Furthermore, many of the above features and characteristics also apply to (e.g., the features or characteristics are identical to the features or characteristics of) three-dimensional structural frameworks of stacked layers of beads (or particles) shown in the foregoing non-limiting FIG. 3. Such features or characteristics are obvious to a person of ordinary skill in the art who is given all information disclosed in this specification. Application of such features or characteristics to three-dimensional structural frameworks of stacked layers of beads (or particles) is included in the invention herein.

Figure 13:
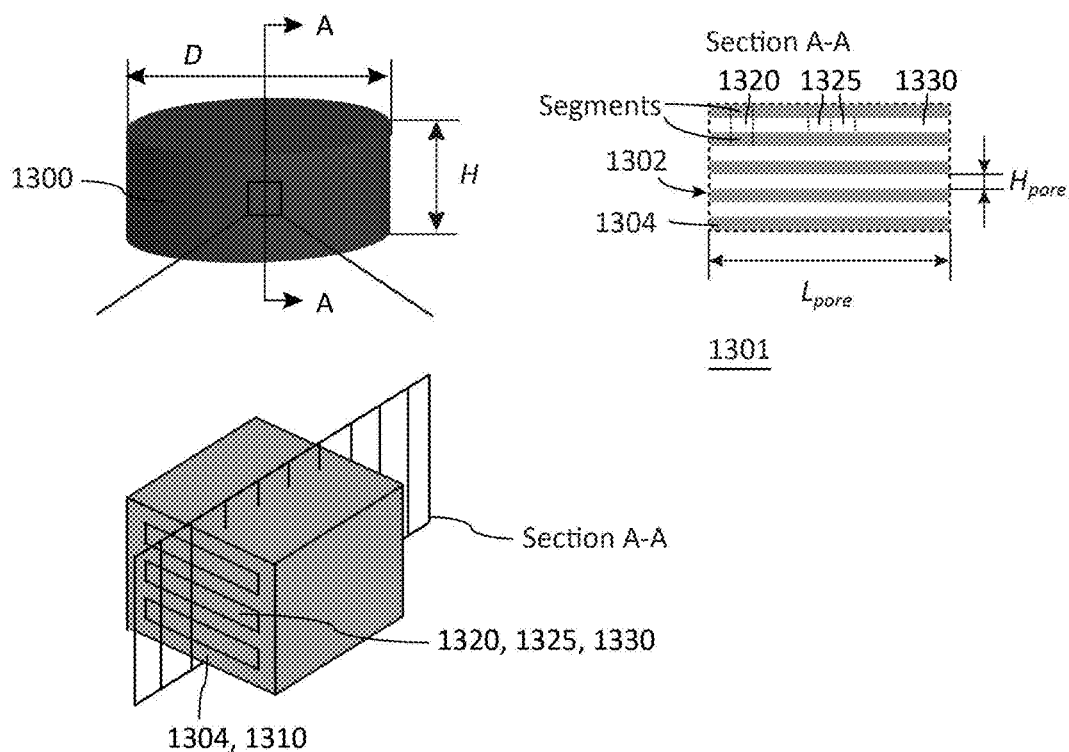
FIG. 13 is another non-limiting schematic of a dosage form according to the invention herein and its microstructure.

FIG. 13 schematically illustrates another pharmaceutical dosage form 1350 comprising a drug-containing solid 1351 having an outer surface 1352 and an internal three dimensional structural framework 1354 comprising a plurality of stacked sheets 1360. Said framework 1354 is contiguous with and terminates at said outer surface 1302. The sheets 1310 further have segments spaced apart from segments of adjoining sheets, thereby defining free spaces 1370. A plurality of adjacent free spaces 1375 combine to define one or more interconnected free spaces forming at least one open pore network 1380. Said at least one open pore network 1380 extends over the entire length of the drug-containing solid 1351 or dosage form 1350. Thus the length, $L_{pore}$, over which said at least one open pore network 1380 extends is the same as the length or diameter, D, of the dosage form 1350 or drug-containing solid 1351. The thickness, $H_{pore}$, however, over which said at least one open pore network 1380 extends is much smaller than the thickness, H, of the dosage form 1350 or drug-containing solid 1351. No walls (e.g., walls comprising the three dimensional structural framework 1354 of elements) must be ruptured to obtain an interconnected cluster of free space 1370, 1375, 1380 (e.g., an open channel of free space) from the outer surface 1352 of the drug-containing solid 1351 to a point or position (or to any point) in the free space 1370, 1375, 1380. However, it may be necessary to rupture one or more walls (e.g., walls comprising the three dimensional structural framework 1354 of elements) to obtain an interconnected cluster of free space (e.g., an open channel of free space) from a point or position within a free space to another point or position in a free space.

In some embodiments, however, at least one free space is enclosed by walls to form a closed cell. In this case, less than five walls may be ruptured to obtain an interconnected cluster of free space (e.g., an open channel of free space) from the outer surface of the drug-containing solid to any point or position in the internal structure. A non-limiting example illustrating a structure where free spaces or "cells" are enclosed by walls is given in FIG. 12 of the U.S. application Ser. No. 15/482,776 titled "Fibrous dosage form".

Typically, moreover, for dissolution fluid to percolate into the interior of the structure the channel size or diameter (e.g., channel width, or pore size, or free spacing, or effective free spacing) must be on the micro- or macro-scale. Thus, in some embodiments, the effective free spacing, $\lambda_{f,e}$, between elements or segments across the open pore network (e.g., the pore size or pore diameter at any point in the open pore network, or the pore size or pore diameter throughout the open pore network) is greater than 1 µm. This includes, but is not limited to $\lambda_{f,e}$ greater than 1.25 µm, or greater than 1.5 µm, or greater than 1.75 µm, or greater than 2 µm, or greater than 5 µm, or greater than 7 µm, or greater than 10 µm, or greater than 15 µm, or greater than 20 µm, or greater than 25 µm, or greater than 30 µm, or greater than 40 µm, or greater than 50 µm.

Because the dosage form volume is generally limited, however, the drug and excipient masses that can be loaded in the dosage form may be too small if the effective free spacing is too large. Thus, in some embodiments, the effective free spacing across the open pore network may be in the ranges 1 µm-5 mm, 1 µm-3 mm, 1.25 µm-5 mm, 1.5 µm-5 mm, 1.5 µm-3 mm, 5 µm-2.5 mm, 10 µm-2 mm, 10 µm-4 mm, 5 µm-4 mm, 10 µm-3 mm, 15 µm-3 mm, 20 µm-3 mm, 30 µm-4 mm, 40 µm-4 mm, or 50 µm-4 mm.

In some embodiments, moreover, the effective free spacing between segments or elements across the one or more free spaces (e.g., across all free spaces of the dosage form) is in the range 1 µm-3 mm. This includes, but is not limited to an effective free spacing between segments or elements across the one or more free spaces in the ranges 1 µm-2.5 mm, or 1 µm-2 mm, or 2 µm-3 mm, or 2 µm-2.5 mm, or 5 µm-3 mm, or 5 µm-2.5 mm, or 10 µm-3 mm, or 10 µm-2.5 mm, or 15 µm-3 mm, or 15 µm-2.5 mm, or 20 µm-3 mm, or 20 µm-2.5 mm. The effective free spacing may be determined experimentally from microstructural images (e.g., scanning electron micrographs, micro computed tomography scans, and so on) of the drug-containing solid. Non-limiting examples describing and illustrating how an effective free spacing may be determined from microstructural images are described and illustrated in the U.S. application Ser. No. 15/482,776 titled "Fibrous dosage form".

It may be noted, moreover, that in some embodiments herein the free spacing or effective free spacing between elements or segments across the three dimensional structural framework or across one or more open pore networks is precisely controlled. A definition of the term "precisely controlled" is given later in this section of the specification.

Furthermore, the free spacing between elements and the surface composition of elements are generally designed to enable percolation of physiological, body, or dissolution fluid into the dosage form structure upon immersion of the dosage form in said fluid. Thus, in some embodiments the free spacing between segments and the composition of the surface of the one or more elements are so that the percolation time of physiological/body fluid into one or more interconnected free spaces of the drug-containing solid is no greater than 200 seconds under physiological conditions. This includes, but is not limited to a percolation time of physiological/body fluid into one or more interconnected free spaces of the drug-containing solid no greater than 100, or no greater than 50 seconds, or no greater than 25 seconds, or no greater than 10 seconds under physiological conditions.

In addition, in some embodiments, upon immersion of the drug-containing solid in a physiological fluid, said fluid percolates more than 40 percent of the free spaces of said drug-containing solid in no more than 600 seconds of immersion.

In some embodiments, moreover, upon immersion of the drug-containing solid in a physiological fluid, said fluid percolates more than 60 percent of the free spaces of said drug-containing solid in no more than 300 seconds of immersion.

In some embodiments, furthermore, upon immersion of the drug-containing solid in a physiological fluid, said fluid percolates more than 50 percent of the free spaces of said drug-containing solid in no more than 100 seconds of immersion.

After percolation, the dissolution fluid interdiffuses with the elements. For achieving a specific surface area (i.e., surface area-to-volume ratio) large enough to guarantee rapid expansion, rapid formation of a viscous medium, and/or rapid dissolution/disintegration of dosage forms, in some embodiments the one or more elements (e.g., fibers, etc.) have an average thickness, $h_0$, no greater than 2.5 mm. This includes, but is not limited to $h_0$ no greater than 2 mm, or no greater than 1.5 mm, or no greater than 1.25 mm, or no greater than 1 mm, or no greater than 750 µm.

It may be noted, however, that if the elements are very thin and tightly packed, the spacing and free spacing between the elements can be so small that the rate at which dissolution fluid percolates or flows into the free space is limited. Furthermore, dosage forms with very thin elements may be difficult to manufacture by, for example, 3D-micro-patterning. Thus, in some embodiments the one or more elements have an average thickness, $h_0$, in the ranges of 0.1 µm-2.5 mm. 0.5 µm-2.5 mm, 1 µm-2.5 mm, 5 µm-2.5 mm, 10 µm-2.5 mm, 2.5 µm-2 mm, 5 µm-2 mm, 5 µm-1.5 mm, 5 µm-1 mm, 10 µm-2 mm, 10 µm-1 mm, 10 µm-750 µm, 20 µm-1.5 mm, or 20 µm-1 mm.

In some embodiments, moreover, the average thickness of the one or more structural elements composing (e.g., producing, making up, etc.) the three dimensional structural framework (e.g., the average thickness of the "frame" of the three dimensional structural framework) is precisely controlled.

The element thickness, h, may be considered the smallest dimension of an element (i.e., h≤w and h≤l, where h, w and l are the thickness, width and length of the element, respectively). The average element thickness, $h_0$, is the average of the element thickness along the length or width of the one or more elements. A non-limiting example for deriving the average element thickness is presented in U.S. application Ser. No. 15/482,776 titled "Fibrous dosage form".

Because the individual elements are generally thin and slender they may bend or deform due to the application of mechanical load. Thus, in some embodiments, to provide mechanical support to the structure the three dimensional structural framework of one or more structural elements may comprise contacts between elements or segments (e.g., contacts between fibers and/or fiber segments, or contacts between a fiber (or fiber segment) and a sheet (or sheet segment), or contacts between beads, and so on). Such contacts between elements include, but are not limited to point contacts or line contacts. In the invention herein, a point contact is referred to as having a contact area or contact zone (e.g., the common surface of the two elements or segments in contact) that extends over a length and width no greater than 2.5 mm. A line contact is referred to as having a contact area or contact zone that extends over a contact length far greater than the contact width. The contact width is typically no greater than 2.5 mm. Moreover, at the contact (e.g., at the contact zone of a point contact or at the contact zone of a line contact), elements or segments may be deformed. The geometry of said elements or segments at or near the contact then is different form the geometry elsewhere. In some embodiments, at the contact an element is "flat" or "flattened".

Figure 14:
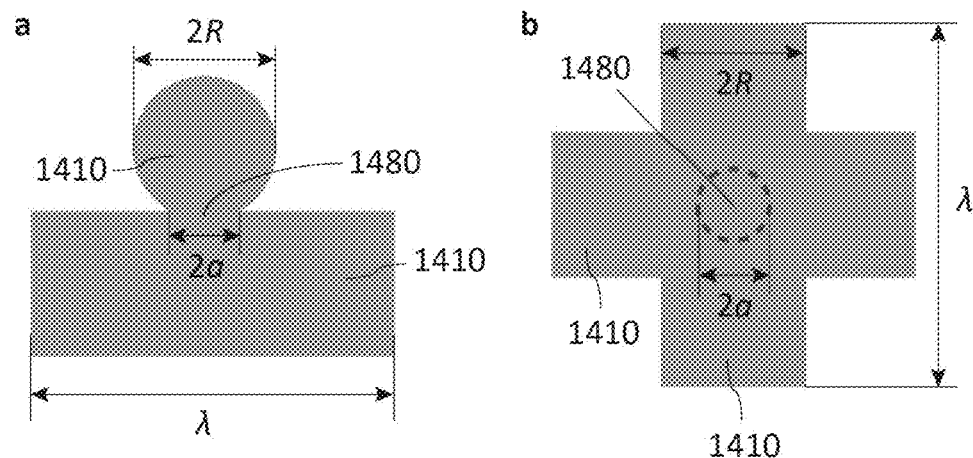
FIG. 14 is a non-limiting schematic of a point contact according to the invention herein.
Figure 15:
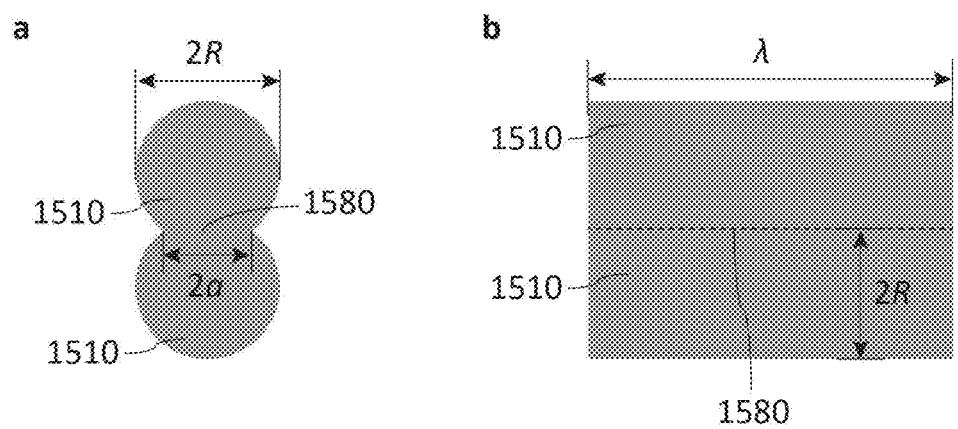
FIG. 15 is a non-limiting schematic of a line contact according to the invention herein.

FIG. 14 is a non-limiting example of a point contact 1480 between two orthogonally aligned fiber segments 1410. FIG. 14a is the front view and FIG. 14b the top view of the two segments. The contact area is circular. The diameter of the circle or "contact width", 2a, is designated in the Figure. FIG. 15 is a non-limiting example of a line contact 1580 between two unidirectionally aligned fiber segments 1510. FIG. 15a is the front view and FIG. 15b the top view. As shown in the Figure the contact width, 2a, is much smaller than the contact length, λ. For further information related to point contacts and line contacts, see, e.g., K. L. Johnson, "Contact mechanics", Cambridge University Press, 1985.

In some embodiments, the number of point contacts in the three dimensional structural framework is at least 10. This includes, but is not limited to a number of point contacts in the three dimensional structural framework at least 20, or at least 50, or at least 75, or at least 100, or at least 125, or at least 150, or at least 175, or at least 200, or at least 250, or at least 300. In some embodiments, moreover, the number of point contacts in the three dimensional structural framework is precisely controlled. In some embodiments, moreover, the number of line contacts in the three dimensional structural framework is at least 10. In some embodiments, moreover, the number of line contacts in the three dimensional structural framework is no greater than 10. In some embodiments, moreover, the number of line contacts in the three dimensional structural framework is precisely controlled.

At the contact zone (e.g., at one or more point contacts or at one or more line contacts, etc.) two elements or segments may be bonded, which is understood herein as "fixed", "joined", "attached", etc. Generally, the bond strength is a fraction of the bulk strength of the contacting elements or segments. Said fraction is typically no greater than 1. This includes but is not limited to a bond strength no greater than 0.8, or no greater than 0.6, or no greater than 0.4, or no greater than 0.2, or no greater than 0.1, or in the ranges 0.001-1, 0.001-0.95, 0.001-0.9, 0.005-1, 0.005-0.95, or 0.01-0.9 times the strength of the bulk of elements or segments. For further information about determining and measuring strength of solid materials, see, e.g., J. M Gere, S. Timoshenko, "Mechanics of materials", fourth edition, PWS Publishing Company, 1997: M. F. Ashby, "Materials selection in mechanical design", fourth edition, Butterworth-Heinemann, 2011: K. L. Johnson, "Contact mechanics", Cambridge University Press, 1985.

Thus, in some embodiments, the three dimensional structural framework of one or more elements is a solid forming a continuous structure wherein at least one element or at least one segment of an element is bonded to another element or another segment of an element. This includes, but is not limited to a three dimensional structural framework of one or more elements forming a continuous solid structure wherein at least two elements or at least two segments of an element, or at least three elements or at least three segments of an element, or at least four elements or at least four segments of an element, or at least five elements or at least five segments of an element, are bonded to another element or another segment of an element.

As the inter-fiber contacts may provide mechanical support to the three dimensional structural framework of elements (e.g., the three dimensional structural network of one or more fibers, etc.), they may also hold up disintegration and dissolution of the structure upon immersion in a dissolution medium. Thus, in some embodiments, a contact width, 2a, between two elements (or two segments) is no greater than 2.5 mm. This includes, but is not limited to a contact width between two elements (or two segments) no greater than 2 mm, or no greater than 1.75 mm, or no greater than 1.5 mm. In other examples without limitation, a contact width, 2a, between two elements (or two segments) may be no greater than 1.1 times the thickness of the contacting elements (or segments) at the position of the contact. This includes, but is not limited to a contact width, 2a, between two elements (or two segments) no greater than 1 time, or no greater 0.8 times, or no greater than 0.6 times the thickness of the contacting elements (or segments) at the position of the contact. Further, in some embodiments, average contact width, 2a, between two elements (or two segments) is no greater than 2.5 mm. This includes, but is not limited to an average contact width between two elements (or two segments) no greater than 2 mm, or no greater than 1.75 mm, or no greater than 1.5 mm.

Moreover, in some embodiments, the contact width of contacts between elements or segments in a dosage form or drug-containing solid or three dimensional structural framework of elements is precisely controlled. In some embodiments, furthermore, the number of contacts between elements (e.g., fibers, fiber segments, beads, sheets, etc.) or segments in a dosage form or drug-containing solid or three dimensional structural framework is precisely controlled.

The dosage form properties (e.g., the uniformity of fluid percolation into the drug-containing solid, the uniformity of dosage form expansion, the drug release rate, etc.) can be optimized if the microstructural parameters are precisely controlled. In the invention herein, the terms "precisely controlled" and "ordered" or "orderly arranged" are used interchangeably. A variable or a parameter (e.g., the contact width, the element thickness, the spacing between elements, etc.) is precisely controlled if it is deterministic and not stochastic (or random). A variable or parameter may be deterministic if, upon multiple repetitions of a step that includes said variable (e.g., if multiple dosage forms are produced under identical or almost identical conditions), the standard deviation of the values of said variable is smaller than the average value. This includes, but is not limited to a standard deviation of the values of said variable smaller than half the average value, or smaller than one third of the average value, or smaller than a quarter of the average value, or smaller than one fifth or the average value, or smaller than one sixth, or smaller than one seventh, or smaller than one eight, or smaller than one ninth, or smaller than one tenth, or smaller than $1/12$, or smaller than $1/15$, or smaller than $1/20$, or smaller than 1/25 of the average value of said variable, or smaller than 1/30 of the average value of said variable.

In some embodiments, the three dimensional structural framework comprises stacked layers (or plies) of particles, fibers, or sheets, or any combinations thereof. In some embodiments, moreover, one or more layers or plies are bonded to the layers above or below said one or more layers.

In some embodiments, the three dimensional structural framework of one or more elements comprises stacked layers of one or more particles, and wherein a particle in a layer is bonded to at least one particle adjacent to said particle in said layer. This includes, but is not limited to a three dimensional structural framework of one or more elements comprising stacked layers of one or more particles, and wherein at least two particles, or at least three particles, or at least four particles, or at least five particles, or at least six particles in a layer are bonded to at least a particle adjacent to said particles in said layer.

In some embodiments, moreover, the three dimensional structural framework comprises stacked layers of one or more particles, and wherein a particle in a layer is bonded to at least one particle in a layer or plie above or below said layer. This includes, but is not limited to a three dimensional structural framework comprising stacked layers of one or more particles, and wherein at least two particles, or at least three particles, or at least four particles, or at least five particles, or at least six particles in a layer are bonded to at least a particle in a layer or plie above or below said layer.

In some embodiments, the three dimensional structural framework comprises stacked layers of one or more sheets, and wherein a sheet is separated from an adjacent sheet by one or more particles between said sheets. In some embodiments, moreover, the three dimensional structural framework comprises stacked layers of one or more sheets, and wherein a sheet is separated from an adjacent sheet by at least one fiber between said sheets.

Figure 16:
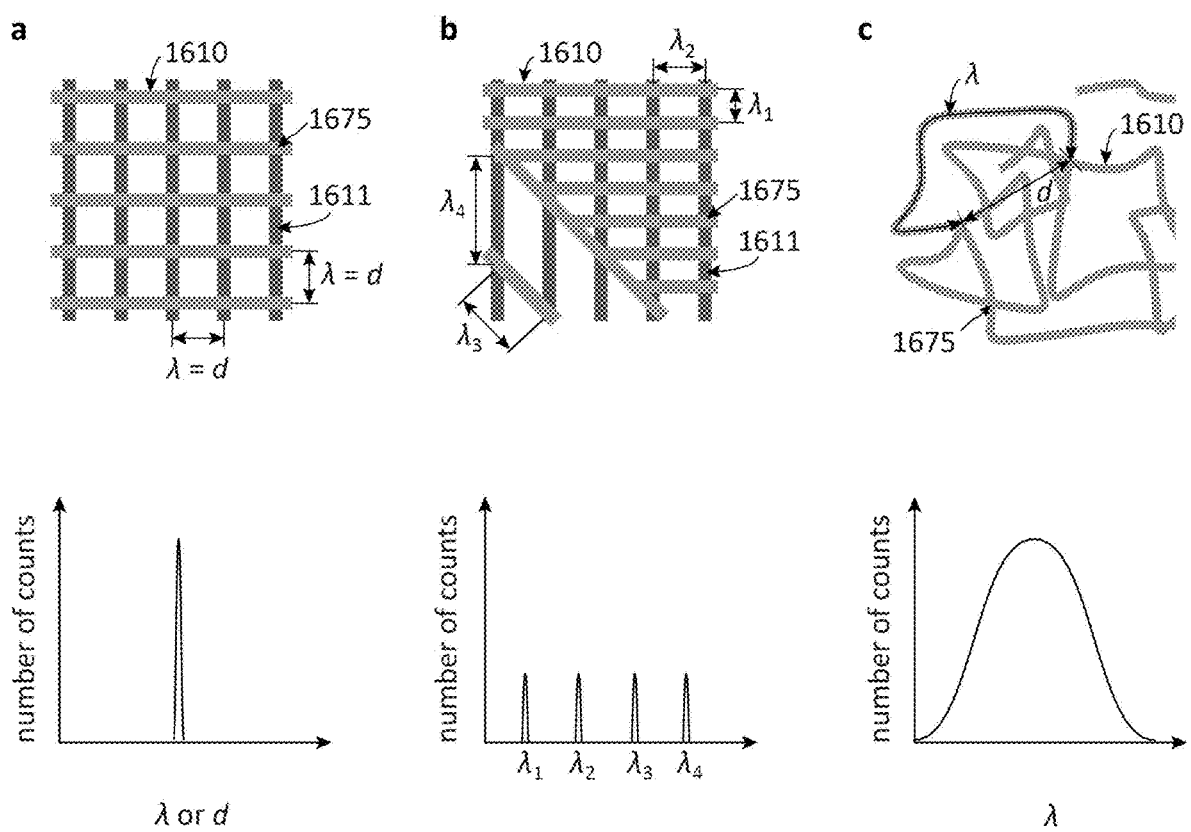
FIG. 16 illustrates non-limiting microstructural parameters of dosage forms herein.

FIG. 16a presents a non-limiting example of the top view of the microstructure of a three dimensional structural framework comprising two criss-crossed stacked layers of fibrous structural elements (e.g., fibers). The fibers in the bottom layer are aligned unidirectionally (e.g., parallel). The fibers in the top layer are aligned unidirectionally, too. The fibers in the two layers are aligned orthogonally to each other (e.g., the fibers in the top layer are aligned orthogonally to the fibers in the bottom layer and vice versa). Thus, the structural framework may be essentially considered a network comprising nodes or vertices at the inter-fiber point contacts and edges defined by the fiber segments between adjacent nodes or vertices. In the specific example of FIG. 16a the distance, $\lambda$, of fiber segments between adjacent point contacts is uniform or constant across the framework.

In some embodiments, therefore, a structural framework comprises a fibrous network having inter-fiber point contacts and fiber segments between adjacent contacts, and wherein the length of fiber segments between adjacent point contacts is uniform across the fibrous network. In some embodiments of the invention herein, a variable (e.g., a length, distance, width, angle, concentration, etc.) is uniform across the structural framework (e.g., across the fibrous network) if the standard deviation of multiple (e.g., multiple, randomly selected, e.g., at least three or at least 4 or at least 5 or at least 6 or at least 10 or at least 20 randomly selected) counts of said variable across the structural framework is less than the average value. This includes, but is not limited to a standard deviation of multiple (e.g., multiple, randomly selected, e.g., at least three or at least 4 or at least 5 or at least 6 or at least 10 or at least 20 randomly selected) counts of said variable across the structural framework less than half the average value, or less than one third of the average value, or less than a quarter of the average value, or less than one fifth of the average value, or less than one sixth of the average value, or less than one eight of the average value, or less than one tenth of the average value, or less than one fifteenth of the average value. The term "uniform" is also referred to herein as "constant" or "almost constant" or "about constant".

The graph of FIG. 16a plots the number of fiber segments between adjacent point contacts versus distance, $\lambda$, of fiber segments between adjacent point contacts. The $\lambda$ values are distributed in a very narrow window or zone around the average, $\lambda_{avg}$. The standard deviation of the $\lambda$ values is very small; $\lambda$ is precisely controlled. The structure is regular, deterministic, and ordered.

In some embodiments, accordingly, the structural framework comprises a fibrous network having inter-fiber point contacts and fiber segments between adjacent contacts, and wherein the length of fiber segments between adjacent point contacts is precisely controlled.

A controlled distance of fiber segments between adjacent point contacts enables controlled percolation of dissolution fluid into the structure and controlled expansion, controlled formation of a viscous medium, and controlled dissolution/disintegration of the dosage form. Thus, in some embodiments where elements comprise one or more fibers and the three dimensional structural framework of one or more fibers (e.g., a plurality of stacked layers of fibrous structural elements, a plurality of criss-crossed stacked layers of fibrous structural elements, etc.) comprises point contacts between fibers or segments, the fiber segment length, $\lambda$, between neighboring (e.g., adjacent) contacts is precisely controlled.

Moreover, in some embodiments, the structural framework comprises a fibrous network having inter-fiber point contacts and fiber segments between adjacent contacts, and wherein the length of fiber segments between adjacent point contacts on average is between 20 μm and 2.5 mm. This includes, but is not limited to an average length of fiber segments between adjacent point contacts in the ranges 20 μm-2 mm, or 30 μm-2 mm, or 30 μm-1.75 mm.

FIG. 16b shows a non-limiting example of the top view of the microstructure of another framework comprising of two criss-crossed stacked layers of fibrous structural elements (e.g., fibers). The fibers in the bottom layer are aligned unidirectionally (e.g., parallel) and equidistantly. The fibers in the top layer are not all aligned in the same direction, but they can be divided into two regions of unidirectionally aligned fibers or fiber segments. The fibers in the top layer, moreover, are aligned orgthogonally or at an angle to the fibers in the bottom layer. Thus, the structural framework may be considered a network comprising nodes or vertices at the inter-fiber point contacts and edges defined by the fiber segments between adjacent nodes or vertices. The distance, A, of fiber segments between adjacent point contacts is uniform or constant across the framework.

The graph of FIG. 16b plots the number of fiber segments between adjacent point contacts versus distance, $\lambda$, of fiber segments between adjacent point contacts. The $\lambda$ values are distributed in a very narrow window or zone around four average values, $\lambda_{1,avg}$, $\lambda_{2,avg}$, $\lambda_{3,avg}$, and $\lambda_{4,avg}$. The standard deviation of the $\lambda$ values is very small: $\lambda_1$, $\lambda_2$, $\lambda_3$, and $\lambda_4$ are precisely controlled. The structure is regular, deterministic, and ordered.

FIG. 16c shows a non-limiting example of the top view of the microstructure of a framework comprising a random or almost random arrangement of fibrous structural elements (e.g., fibers). The structural framework may be considered a network comprising nodes or vertices at the inter-fiber point contacts and edges defined by the fiber segments between adjacent nodes or vertices.

The graph of FIG. 16c plots the number of fiber segments between adjacent point contacts versus distance, $\lambda$, of fiber segments between adjacent point contacts. The $\lambda$ values are distributed in a broad window or zone around the average values, $\lambda_{avg}$. The standard deviation of the $\lambda$ values is much larger than in the previous cases.

Figure 17:
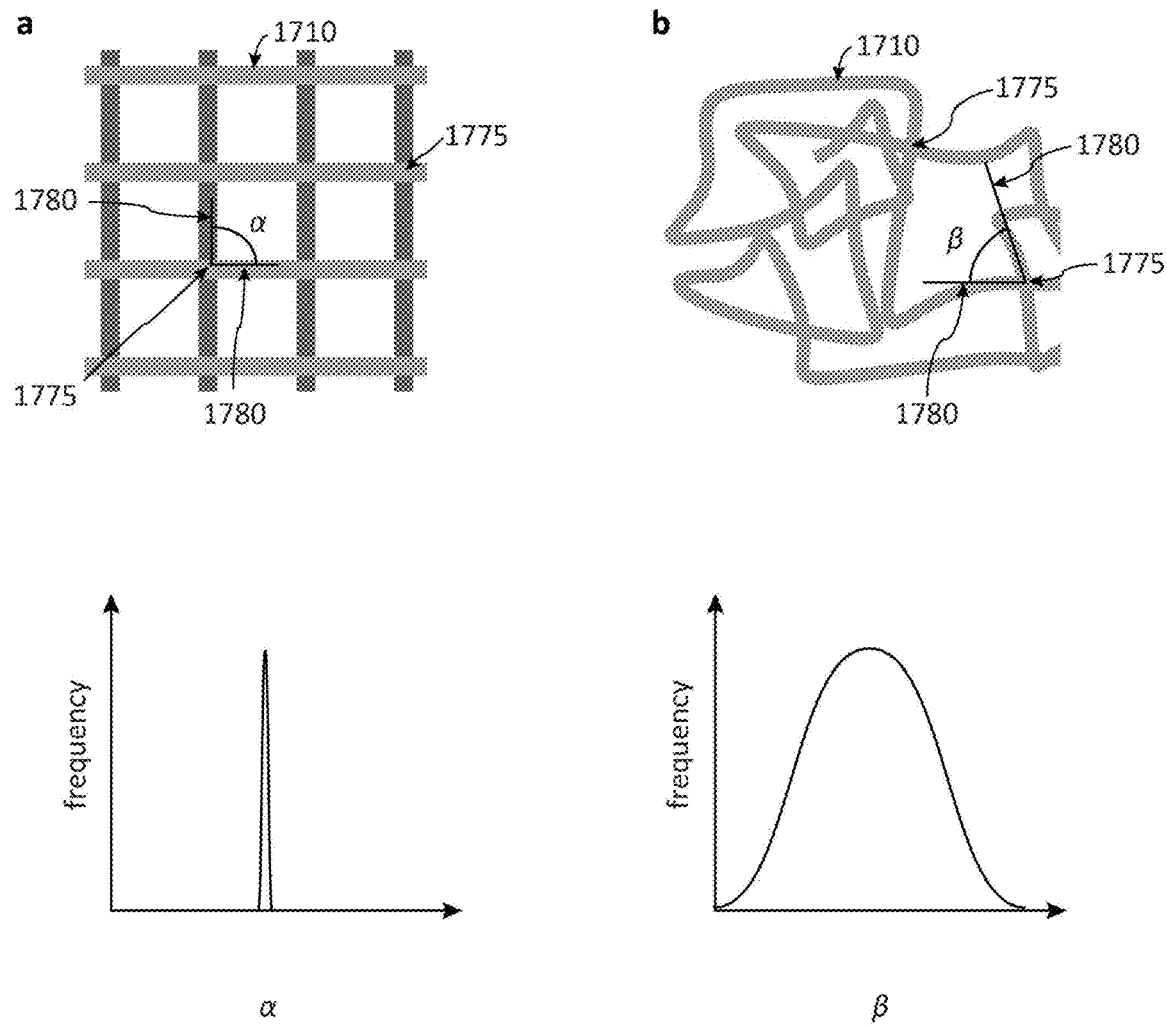
FIG. 17 is another non-limiting illustration of microstructural parameters of dosage forms herein.

FIG. 17a presents a non-limiting example of the top view of the microstructure of two criss-crossed stacked layers of fibrous structural elements (e.g., fibers). The fibers in the bottom layer are aligned unidirectionally (e.g., parallel). The fibers in the top layer are aligned unidirectionally, too, and orthogonally to the fibers in the bottom layer. The two layers are bonded at inter-fiber point contacts. Thus, at the inter-fiber point contacts the tangent to the two contacting fibers or fiber segments forms an angle, $\alpha$. In the non-limiting example shown in FIG. 17a the distance, $\lambda$, of fiber segments between point contacts is uniform or constant across the framework. Thus the angle, $\alpha$, formed by the tangents of two contacting fiber segments (e.g., the angle of intersection) at the contact is about 90°.

The graph of FIG. 17a plots the number of angles of intersection formed by intersecting fiber segments at point contacts versus angle of intersection, $\alpha$. The $\alpha$ values are distributed in a very narrow window or zone around the average, $\alpha_{avg}$. The standard deviation of the $\alpha$ values is very small: $\alpha$ is precisely controlled. The structure is regular, deterministic, and ordered.

FIG. 17b shows a non-limiting example of the top view of the microstructure of a framework comprising a random or almost random arrangement of fibrous structural elements (e.g., fibers). Fibrous elements or segments are bonded to other fibrous elements or segments at inter-fiber point contacts. At the inter-fiber point contacts intersecting fibers or fiber segments forms an angle of intersection, $\alpha$.

The graph of FIG. 17b plots the number of angles of intersection formed by two intersecting fiber segments at point contacts versus angle of intersection, $\alpha$. Because the structure is random the $\alpha$ values are distributed in a broad window or zone around the average, $\alpha_{avg}$. The standard deviation of the $\alpha$ values is much greater than in the previous cases.

In some embodiments, therefore, the three-dimensional structural framework of one or more elements comprises a fibrous network having inter-fiber point contacts defined by intersecting fibers or fiber segments, and wherein the angle of intersection at said point contacts is precisely controlled across said fibrous network.

In some embodiments, the three-dimensional structural framework of one or more elements comprises a fibrous network having inter-fiber point contacts defined by intersecting fibers or fiber segments, and wherein the angle of intersection at said point contacts is uniform across said fibrous network.

Generally, moreover, said angle of intersection is greater than 0 degrees (e.g., greater than 0 degrees on average across the structural framework). This includes, but is not limited to an angle of intersection greater than 5 degrees, or greater than 10 degrees, or greater than 15 degrees, or greater than 20 degrees, or greater than 25 degrees, or greater than 30 degrees, or greater than 35 degrees, or greater than 40 degrees, or at least 45 degrees (e.g., on average across the structural framework). In preferred embodiments said angle of intersection is about 90 degrees (e.g., on average across the structural framework).

In some embodiments, furthermore, the three-dimensional structural framework of one or more elements comprises a fibrous network having inter-fiber point contacts defined by intersecting fibers or fiber segments, and wherein the angle of intersection at said point contacts is between 40 and 90 degrees on average. This includes, but is not limited to an average angle of intersection at between intersecting fibers or intersecting fiber segments in the ranges 50-90, or 60-90, or 70-90, or 80-90 degrees.

In some embodiments, moreover, the volume fraction of elements having at least one sparingly-soluble active ingredient dissolved as molecules or dispersed as nanometer-scale aggregates in a water-soluble excipient matrix is no greater than 0.8 (e.g., in the ranges 0.1-0.8, 0.2-0.8, 0.3-0.8, 0.35-0.8, 0.4-0.8) with respect to the volume of the drug-containing solid. Furthermore, in some embodiments, the volume fraction of elements having at least one sparingly-soluble active ingredient dissolved as molecules or dispersed as nanometer-scale aggregates in a water-soluble excipient matrix that is further soluble in gastric acid is no greater than 0.8 (e.g., in the ranges 0.1-0.8, 0.2-0.8, 0.3-0.8, 0.35-0.8, 0.4-0.8) with respect to the volume of the drug-containing solid.

Further non-limiting embodiments of the dosage form structure are presented in U.S. application Ser. No. 15/482,776 titled "Fibrous dosage form", U.S. application Ser. No. 15/964,058 titled "Method and apparatus for the manufacture of fibrous dosage forms", the U.S. application Ser. No. 15/964,063 and titled "Dosage form comprising two-dimensional structural elements", and the International Application No. PCT/US19/19004 titled "Expanding structured dosage form". More examples of how the elements may be structured or arranged in the three dimensional structural framework of one or more solid elements would be obvious to a person of ordinary skill in the art. All of them are within the spirit and scope of this invention.

c) Nano-Structure and Composition of Drug-Containing Solid

In some embodiments, the solubility of one or more sparingly-soluble drugs in a physiological/body fluid (e.g., gastric fluid or simulated gastric fluid or simulated gastric fluid having a pH value no greater than 4) under physiological conditions is no greater than 1 mg/ml. This includes, but is not limited to a solubility of one or more sparingly-soluble drugs in a physiological/body fluid (e.g., gastric fluid or simulated gastric fluid or simulated gastric fluid having a pH value no greater than 4) under physiological conditions no greater than 0.5 mg/ml, or no greater than 0.2 mg/ml, or no greater than 0.1 mg/ml, or no greater than 0.075 mg/ml.

In some embodiments, at least one water-soluble polymeric carrier comprises an amorphous molecular structure (e.g., an amorphous arrangement of molecules).

In some embodiments, moreover, at least one sparingly water-soluble drug is dissolved in said amorphous molecular structure. If the drug is soluble in the carrier excipient, the carrier excipient may form a thermodynamically stable solid solution of dispersed, sparingly-soluble drug molecules and carrier excipient. If the solubility of drug molecules in said amorphous molecular structure is lower than the concentration of drug molecules in said amorphous molecular structure, the drug molecules may be "kinetically frozen" in the carrier excipient. The drug-excipient solid solution with "kinetically frozen" drug molecules in carrier excipient may be "stable" as long as the temperature of the solid solution is maintained below or far below (e.g., at least 10 degrees Celsius, or at least 20 degrees Celsius, or at least 30 degrees Celsius, or at least 40 degrees Celsius below) the glass transition temperature. Thus, in some embodiments, the glass transition temperature of a drug-excipient solid solution is greater than 10 degrees Celsius, or greater than 20 degrees Celsius, or greater than 30 degrees Celsius, or greater than 40 degrees Celsius, or greater than 50 degrees Celsius.

To ensure that dissolution fluid penetrates into the structural framework after dissolution fluid percolated the free spaces, in some embodiments at least one carrier excipient is absorptive of a physiological/body fluid under physiological conditions. In the invention herein, a carrier excipient is absorptive of a physiological/body fluid if the effective diffusivity of physiological/body fluid in said carrier excipient (and/or an element or segment comprising said excipient) is greater than $0.5 \times 10^{-11}$ m$^2$/s under physiological conditions. In other examples without limitation, the effective diffusivity of physiological/body fluid in an absorptive carrier excipient (and/or an element or segment comprising said excipient) may be greater than $1 \times 10^{-11}$ m$^2$/s, greater than $3 \times 10^{-11}$ m$^2$/s, greater than $6 \times 10^{-11}$ m$^2$/s, or greater than $8 \times 10^{-11}$ m$^2$/s under physiological conditions.

Alternatively, for absorptive excipients where diffusion of physiological/body fluid to the interior is not Fickian, a rate of penetration may be specified. In some embodiments, the rate of penetration of a physiological/body fluid into a solid, absorptive excipient (and/or an element) is greater than an average thickness of the one or more drug-containing elements divided by 3600 seconds (i.e., $h_0/3600$ μm/s). In other examples without limitation, rate of penetration may be greater than $h_0/1800$ μm/s, greater than $h_0/1200$ μm/s, greater than $h_0/800$ μm/s, or greater than $h_0/600$ μm/s.

For determining the effective diffusivity (and/or the rate of penetration) of dissolution medium in a solid, absorptive excipient (and/or an element) the following procedure may be applied. An element (e.g an element or segment of the dosage form structure or an element or segment that just consists of the absorptive excipient) may be fixed at both ends and placed in a still dissolution medium at 37° C. The time $t_1$ for the element to break apart or deform substantially may be recorded. (By way of example but not by way of limitation, a deformation of an element may be considered substantial if either the length, width, or thickness of the element differs by more than 10 to 20 percent from its initial value. In elements with weight fraction, $w_e$, or volume fraction, $\varphi_e$, of absorptive/swellable excipient smaller than 0.4, a deformation of an element or segment may be considered substantial if either the length, width, or thickness of the element or segment differs by more than $25 \times \varphi_e$ percent or $25 \times w_e$ percent from its initial value.) The effective diffusivity, $D_{eff}$, may then be determined according to $D_{eff} = h_{init}^2/4t_1$ where him is the initial element or segment thickness (e.g., the thickness of the dry element). Similarly, the rate of penetration of a physiological/body fluid into the element or segment is equal to $h_{init}/2t_1$. Further non-limiting examples for deriving the effective diffusivity or rate of penetration are presented in U.S. application Ser. No. 15/482,776 titled "Fibrous dosage form".

For achieving rapid erosion of solid elements after contact with physiological/body fluids, in some embodiments at least one strength-enhancing constituent or carrier excipient has a solubility greater than 0.1 g/l in physiological/body fluids under physiological conditions. This includes, but is not limited to a solubility of at least one strength-enhancing constituent or carrier excipient in a physiological/body fluid greater than 0.5 g/l, or greater than 1 g/l, or greater than 5 g/l, or greater than 10 g/l, or greater than 20 g/l, or greater than 30 g/l, or greater than 50 g/l, or greater than 70 g/l, or greater than 100 g/l.

For polymers that form viscous solutions when combined with a dissolution medium, the 'solubility' in the context of this invention is the polymer concentration in physiological/body fluid at which the average shear viscosity of the polymer-physiological/body fluid solution is 5 Pa·s in the shear rate range 1-100 1/s under physiological conditions. The pH value of the physiological/body fluid may thereby be adjusted to the specific physiological condition of interest. By contrast, for a material that does not form a viscous solution when combined with a dissolution medium, the solubility herein is the ratio of the maximum mass of said material that can be dissolved in a given volume of dissolution medium at equilibrium divided by said volume of the medium. It may, for example, be determined by optical methods.

In some embodiments herein, the diffusivity of a dissolved or solvated molecule of at least one strength-enhancing constituent in a physiological/body fluid may be greater than $0.5 \times 10^{-12}$ m$^2$/s under physiological conditions. This includes, but is not limited to a diffusivity of a dissolved molecule of at least one strength-enhancing constituent in a physiological/body fluid greater than $1 \times 10^{-12}$ m$^2$/s, or greater than $2 \times 10^{-12}$ m$^2$/s, or greater than $4 \times 10^{-12}$ m$^2$/s, or greater than $6 \times 10^{-12}$ m$^2$/s, or greater than $8 \times 10^{-12}$ m$^2$/s under physiological conditions.

Non-limiting examples of excipients that satisfy some or all the requirements of the amorphous solid constituent (e.g., the carrier excipient) include hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, hydroxyethyl cellulose, methyl cellulose, hydroxypropyl methyl ether cellulose, starch, chitosan, pectin, polymethacrylates (e.g., poly(methacrylic acid, ethyl acrylate) 1:1, or butylmethacrylat-(2-dimethylaminocthyl)methacrylat-methylmathacrylat-copolymer), vinylpyrrolidone-vinyl acetate copolymer, carbopol (e.g., acrylic acid crosslinked with allyl sucrose or allyl pentaerythritol), among others.

In some embodiments, moreover, the molecular weight of at least one water-soluble polymer carrier is between 2 kg/mol and 1000 kg/mol. This includes, but is not limited to a molecular weight of at least one water-soluble polymer carrier in the range 2-700 kg/mol, or 2-500 kg/mol, or 2-400 kg/mol, or 2-300 kg/mol, or 2-200 kg/mol.

For enhancing drug solubility in the water-penetrated three dimensional structural framework, element, and segment, as well as in the dissolution fluid the structural framework or at least one element or one or more elements comprise an amphiphilic excipient. An amphiphilic molecule is referred to as possessing at least hydrophilic and hydrophobic properties. A non-limiting example of an amphiphilic excipient is a copolymer (e.g., a polymer made of at least two monomer) having at least a hydrophobic branch (e.g., an arrangement of hydrophobic monomers) and at least a hydrophilic branch (e.g., an arrangement of hydrophilic monomers).

In some embodiments, at least one amphiphilic polymer self-assembles in aqueous solutions to form regions of heterogeneous degree of hydrophobicity or hydrophilicity. In some embodiments, the amphiphilic polymer self-assembles as micelles in aqueous solutions, and wherein the critical micelle concentration is smaller than 1 mg/ml. It may be noted that the terms "self-assemblages", "micelles", "aggregates formed by the amphiphilic polymer", and "dendrimers" are used interchangeably herein. They are understood as self-assemblages of an amphiphilic polymer in aqueous solutions. Said self-assemblages comprise regions of heterogeneous degree of hydrophobicity or hydrophilicity.

In some embodiments, the micelles or aggregates formed by the amphiphilic polymer must be permeable across the gastrointestinal wall. Thus, in some embodiments the molecular weight of at least one amphiphilic polymer is smaller than 500 kg/mol (e.g., smaller than 250 kg/mol, or smaller than 100 kg/mol, or smaller than 50 kg/mol, or smaller than 20 kg/mol, or smaller than 10 kg/mol). In some embodiments, the molecular weight of at least one amphiphilic polymer is in the range 0.1 kg/mol-50 kg/mol (e.g., 0.1-25 kg/mol. 0.1-10 kg/mol. 0.1-5 kg/mol. 0.1-3 kg/mol. 0.1-2 kg/mol).

Figure 18:
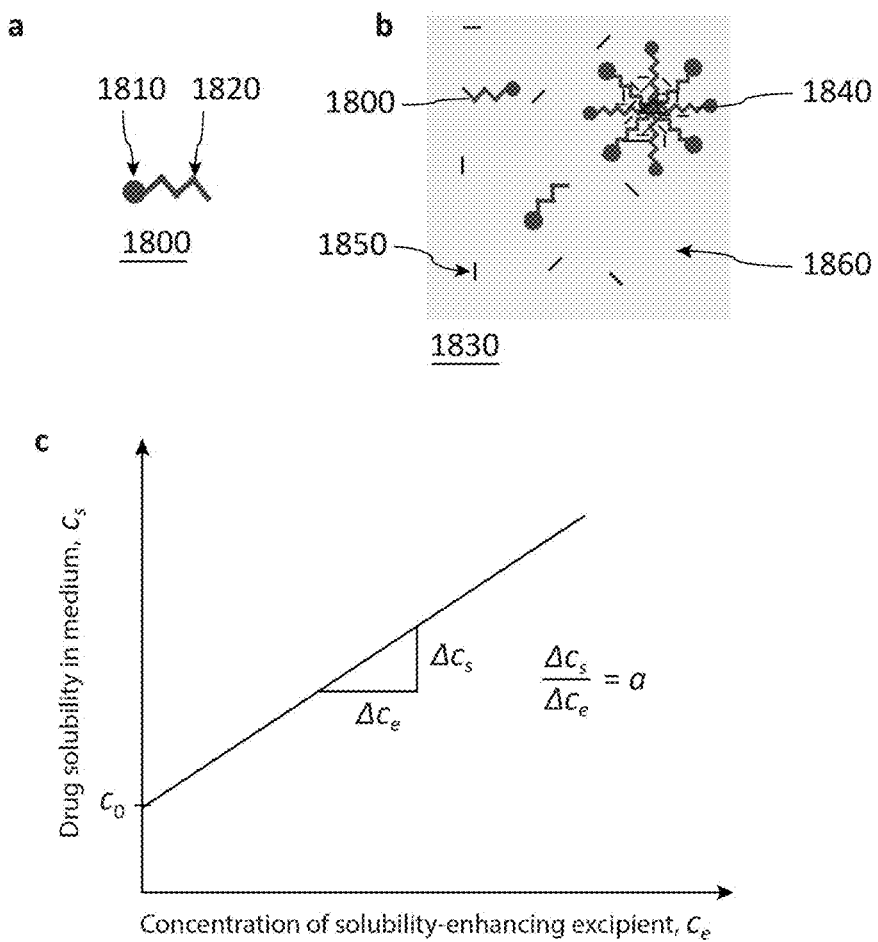
FIG. 18 schematically illustrates (a) a non-limiting amphiphilic molecule, (b) formation of micelles in aqueous solutions and accumulation of drug molecules in said micelles, and (c) drug solubility in an aqueous solution or medium versus concentration of amphiphilic or solubility-enhancing excipient.

FIG. 18a presents a non-limiting schematic of a solubility-enhancing constituent (or solubility-enhancing excipient) comprising an amphiphilic polymer molecule 1800 of at least a hydrophilic branch or block 1810 and at least a hydrophobic branch or block 1820. Upon immersion in a drug-containing aqueous solution 1830 the amphiphilic molecules 1800 may self-assemble to form self-assemblages or micelles 1840 comprising a hydrophobic core and a hydrophilic shell as shown schematically in FIG. 18b. The solubility of drug molecules 1850 in the hydrophobic core may be much greater than that in the 'pure' dissolution fluid 1860 (e.g., the dissolution fluid without any excipient). Thus, as the drug molecules 1850 accumulate in the core, the "overall solubility" or "average solubility" or "solubility" of the drug in the drug-excipient-dissolution fluid solution 1830 is enhanced. FIG. 18c presents a non-limiting curve of the drug solubility in the drug-excipient-dissolution fluid solution 1830 versus concentration of the solubility-enhancing excipient 1800. The drug solubility increases linearly with excipient concentration in the given range. The slope of the curve is a.

In some embodiments, a slope a of the drug solubility versus excipient concentration curve in an aqueous solution is greater than 0.001. This includes but is not limited to a slope a of the drug solubility versus excipient concentration curve in an aqueous medium greater than 0.002, or greater than 0.003, or greater than 0.004, or greater than 0.005, or greater than 0.007, or greater than 0.01, or greater than 0.015, or greater than 0.02.

In some embodiments, a slope, a, of the drug solubility versus concentration of solubility-enhancing constituent in an aqueous solution is greater than $0.05 \times c_0$, 0.05 times the drug solubility in said aqueous solution without excipient. This includes but is not limited to a slope a of the drug solubility versus excipient concentration curve in an aqueous medium greater than $0.1 \times c_0$, or greater than $0.2 \times c_0$, or greater than $0.3 \times c_0$, or greater than $0.4 \times c_0$, or greater than $0.5 \times c_0$.

In some embodiments, the amphiphilic excipient is selected from the group comprising polyoxyl stearate, polyethylene glycol methyl ether-block-polylactide-co-glycolide, polyethylene glycol-polylactic acid (PEG-PLA) copolymer, poloxamer, lauroyl macrogol-32 glyceride, dendrimers (e.g., polyamidoamine dendrimer or a dendrimer consisting of an ethylene diamine core or a dendrimer comprising a repetitive branching of amido amine or a dendrimer comprising a primary amine surface) and others.

In some embodiments, the weight fraction of sparingly-soluble drug (e.g., the weight fraction of sparingly-soluble drug in the form of dissolved molecules in a water-soluble polymer carrier, or the weight fraction sparingly-soluble drug in the form of nanometer-scale aggregates dispersed in a water-soluble polymer carrier, or the weight fraction of sparingly-soluble drug in the form of molecules dissolved in or nanometer-scale aggregates dispersed in a water-soluble polymer carrier) in an element (e.g., a fiber, sheet, bead etc.) with respect to the total weight of said element (e.g., the total weight of said fiber, sheet, etc.) is no greater than 0.8. This includes, but is not limited to a drug weight fraction in an element with respect to the total weight of said element no greater than 0.7, or no greater than 0.6, or no greater than 0.5, or no greater than 0.4.

In some embodiments, moreover, the weight fraction of sparingly-soluble drug (e.g., the weight fraction of sparingly-soluble drug in the form of dissolved molecules in a water-soluble polymer carrier, or the weight fraction sparingly-soluble drug in the form of nanometer-scale aggregates dispersed in a water-soluble polymer carrier, or the weight fraction of sparingly-soluble drug in the form of molecules dissolved in or nanometer-scale aggregates dispersed in a water-soluble polymer carrier) in the three-dimensional structural framework with respect to the total weight of said framework is no greater than 0.8. This includes, but is not limited to a drug weight fraction in an element with respect to the total weight of said element no greater than 0.7, or no greater than 0.6, or no greater than 0.5, or no greater than 0.4.

In some embodiments, the weight fraction of a sparingly-soluble drug dissolved in one or more elements with respect to the total weight of said sparingly-soluble drug in said one or more elements is greater than 0.2. This includes, but is not limited to a weight fraction of a sparingly-soluble drug dissolved in one or more elements with respect to the total weight of said sparingly-soluble drug in said one or more elements greater than 0.3, or greater than 0.4, or greater than 0.5, or greater than 0.6, or greater than 0.7, or greater than 0.8, or greater than 0.9, or greater than 0.95.

In some embodiments, the weight fraction of a sparingly-soluble drug dispersed as nanometer-scale aggregates in one or more elements with respect to the total weight of said sparingly-soluble drug in said one or more elements is greater than 0.2. This includes, but is not limited to a weight fraction of a sparingly-soluble drug dispersed as nanometer-scale aggregates in one or more elements with respect to the total weight of said sparingly-soluble drug in said one or more elements greater than 0.3, or greater than 0.4, or greater than 0.5, or greater than 0.6, or greater than 0.7, or greater than 0.8, or greater than 0.9.

In some embodiments, the weight fraction of a sparingly-soluble drug in the form of dissolved molecules or dispersed nanometer-scale aggregates in one or more elements with respect to the total weight of said sparingly-soluble drug in said one or more elements is greater than 0.2. This includes, but is not limited to a weight fraction of a sparingly-soluble drug in the form of dissolved molecules or dispersed nanometer-scale aggregates in one or more elements with respect to the total weight of said sparingly-soluble drug in said one or more elements greater than 0.3, or greater than 0.4, or greater than 0.5, or greater than 0.6, or greater than 0.7, or greater than 0.8, or greater than 0.9, or greater than 0.95.

In some embodiments, the weight fraction of the excipient that is soluble in water or physiological fluid in one or more elements or in the three dimensional structural framework is greater than 0.3. This includes, but is not limited to a weight fraction of water-soluble excipient in one or more elements or in the three dimensional structural framework greater than 0.4, or greater than 0.5, or greater than 0.6, or greater than 0.7.

In some embodiments, the weight fraction of water-soluble polymer carrier in an element with respect to the total weight of said element is greater than 0.15. This includes, but is not limited to a weight fraction of water-soluble polymer carrier in an element with respect to the total weight of said element greater than 0.2, or greater than 0.25, or greater than 0.3, or greater than 0.35.

In some embodiments, moreover, the weight fraction of water-soluble polymer carrier in an element with respect to the total weight of said element is in the range 0.15-0.9. This includes, but is not limited to a weight fraction of water-soluble polymer carrier in an element with respect to the total weight of said element in the range 0.15-0.85, or 0.15-0.8, or 0.15-0.75, or 0.15-0.7, or 0.15-0.65, or 0.2-0.85, or 0.25-0.85.

In some embodiments, the drug molecules or nanometer-scale aggregates are uniformly (e.g., spatially uniformly) or almost uniformly dispersed across a structural element or the three dimensional structural framework. In the invention herein, a drug is understood uniformly or spatially uniformly dispersed or distributed in an element or framework if the drug concentration across said element or framework (e.g., across the body of said element or framework) is constant or almost constant.

In some embodiments, moreover, the concentration of sparingly-soluble drug is uniform (e.g., constant) across the water-soluble or gastric acid-soluble excipient matrix of an element or the three dimensional structural framework.

In some embodiments, wherein the excipient comprises one or more water-soluble polymer carriers (e.g., strength-enhancing constituents), the weight fraction of water-soluble polymer carrier (e.g., the weight fraction of one or more water-soluble polymer carriers, or one or more strength-enhancing constituents) in one or more elements or in the three-dimensional structural framework with respect to the total weight of said one or more elements or said three dimensional structural framework is greater than 0.1. This includes, but is not limited to a weight fraction of water-soluble polymer carrier in one or more elements or in the three dimensional structural framework with respect to the total weight of said one or more elements or said three dimensional structural framework greater than 0.15, or greater than 0.2, or greater than 0.25, or greater than 0.3, or greater than 0.35, or greater than 0.4, or in the ranges 0.15-0.95, 0.15-0.9, 0.2-0.9, 0.25-0.9, or 0.2-0.85.

In some embodiments, wherein the excipient comprises one or more amphiphilic, solubility-enhancing constituents, the weight fraction of amphiphilic, solubility-enhancing constituent (e.g., the weight fraction of one or more amphiphilic, solubility-enhancing constituents) in one or more elements or in the structural framework with respect to the total weight of said one or more elements or the structural framework is greater than 0.05. This includes, but is not limited to a weight fraction of amphiphilic, solubility-enhancing constituent in one or more elements or the structural framework with respect to the total weight of said one or more elements or said structural framework greater than 0.1, or greater than 0.15, or greater than 0.2, or greater than 0.25, or in the range 0.05-0.8, or in the range 0.05-0.7, or in the range 0.1-0.5, or in the range 0.05-0.6, or in the range 0.1-0.7, or in the range 0.15-0.5, or in the range 0.15-0.6.

In some embodiments, moreover, the amphiphilic polymer is dissolved as molecules or dispersed as nanometer-scale aggregates in a water-soluble polymer carrier. In some embodiments, the amphiphilic polymer is dispersed as particles of number-average size no greater than 50 µm (e.g., no greater than 40 µm, or no greater than 30 µm, or no greater than 20 µm, or no greater than 10 µm) in a water-soluble polymer carrier.

In some embodiments, the weight fraction of an amphiphilic excipient dissolved in one or more elements with respect to the total weight of said amphiphilic excipient in said one or more elements is greater than 0.2. This includes, but is not limited to a weight fraction of amphiphilic excipient dissolved in one or more elements with respect to the total weight of said amphiphilic excipient in said one or more elements greater than 0.3, or greater than 0.4, or greater than 0.5, or greater than 0.6, or greater than 0.7, or greater than 0.8, or greater than 0.9, or greater than 0.95.

In some embodiments, the weight fraction of an amphiphilic excipient dispersed as nanometer-scale aggregates in one or more elements with respect to the total weight of said amphiphilic excipient in said one or more elements is greater than 0.2. This includes, but is not limited to a weight fraction of an amphiphilic excipient dispersed as nanometer-scale aggregates in one or more elements with respect to the total weight of said amphiphilic excipient in said one or more elements greater than 0.3, or greater than 0.4, or greater than 0.5, or greater than 0.6, or greater than 0.7, or greater than 0.8, or greater than 0.9.

In some embodiments, the weight fraction of an amphiphilic excipient in the form of dissolved molecules or dispersed nanometer-scale aggregates in one or more elements with respect to the total weight of said amphiphilic excipient in said one or more elements is greater than 0.2. This includes, but is not limited to a weight fraction of an amphiphilic excipient in the form of dissolved molecules or dispersed nanometer-scale aggregates in one or more elements with respect to the total weight of said amphiphilic excipient in said one or more elements greater than 0.3, or greater than 0.4, or greater than 0.5, or greater than 0.6, or greater than 0.7, or greater than 0.8, or greater than 0.9, or greater than 0.95.

In some embodiments, the weight fraction of an amphiphilic excipient in the form of dispersed particles of number-average size no greater than 50 µm (e.g., no greater than 40 µm, or no greater than 30 pun, or no greater than 20 µm, or no greater than 10 µm) in one or more elements with respect to the total weight of said amphiphilic excipient in said one or more elements is greater than 0.2. This includes, but is not limited to a weight fraction of an amphiphilic excipient in the form dispersed particles of number-average size no greater than 50 µm (e.g., no greater than 40 µm, or no greater than 30 µm, or no greater than 20 µm, or no greater than 10 µm) in one or more elements with respect to the total weight of said amphiphilic excipient in said one or more elements greater than 0.3, or greater than 0.4, or greater than 0.5, or greater than 0.6, or greater than 0.7, or greater than 0.8, or greater than 0.9, or greater than 0.95.

In some embodiments, the concentration of amphiphilic polymer is uniform across an element. In some embodiments, the concentration of amphiphilic polymer is uniform across the water-soluble or gastric-acid-soluble excipient matrix of one or more elements or the three dimensional structural framework. In some embodiments, the concentration of amphiphilic polymer is uniform across a region of one or more elements comprising a composition of a sparingly-soluble drug and a water-soluble polymer carrier. In some embodiments, the concentration of amphiphilic polymer is uniform across the three dimensional structural framework. In some embodiments, the concentration of amphiphilic polymer is uniform across a region of the three dimensional structural framework comprising a composition of a sparingly-soluble drug and a water-soluble polymer carrier.

In some embodiments of the invention herein, the concentration of a substance is uniform across a region of the structural framework if the standard deviation of multiple (e.g., multiple, randomly selected, e.g., at least three or at least 4 or at least 5 or at least 6 or at least 10 or at least 20 randomly selected) concentration samples from said region is less than the average concentration. This includes, but is not limited to a standard deviation of multiple (e.g., multiple, randomly selected, e.g., at least three or at least 4 or at least 5 or at least 6 or at least 10 or at least 20 randomly selected) concentration samples from said region less than half, or less than one third, or less than a quarter, or less than one fifth, or less than one sixth, or less than one eight, or less than one tenth, or less than one fifteenth of the average concentration.

In some embodiments, moreover, the weight fraction of amphiphilic polymer across a region (e.g., a part, or a fraction, or a section, or all) of one or more elements comprising a composition of a sparingly-soluble drug and a water-soluble polymer carrier is greater than 0.05 (e.g., with respect to the total weight of said region). This includes, but is not limited to a weight fraction of amphiphilic polymer across a region (e.g., a part, or a fraction, or a section, or all) of one or more elements comprising a composition of a sparingly-soluble drug and a water-soluble polymer carrier greater than 0.05, or greater than 0.1, or greater than 0.15, or in the ranges 0.1-0.8, 0.1-0.75, or 0.15-0.8 (e.g., with respect to the total weight of said region).

In some embodiments, moreover, at least a sparingly-soluble drug, at least a water-soluble polymer carrier, and at least an amphiphilic excipient are blended through the body of one or more elements. In some embodiments, at least a sparingly-soluble drug, at least a water-soluble polymer carrier, and at least an amphiphilic excipient are blended through the body of the structural framework.

It may be obvious to a person of ordinary skill in the art that a solubility-enhancing, amphiphilic excipient molecule may comprise multiple hydrophilic blocks or regions and/or multiple hydrophobic blocks or regions. Furthermore, it may be obvious to a person of ordinary skill in the art that additional excipients having additional functionalities may be added to the dosage form or one or more elements. Moreover, it would be obvious to a person of ordinary skill in the art that one excipient material (e.g., one constituent) may assume or have multiple functions or functionalities. All such excipients, excipient combinations, or additional functionalities obvious to a person of ordinary skill in the art are within the spirit and scope of this disclosure.

d) Expansion Properties Drug-Containing Solid and Dosage Form

Figure 19:
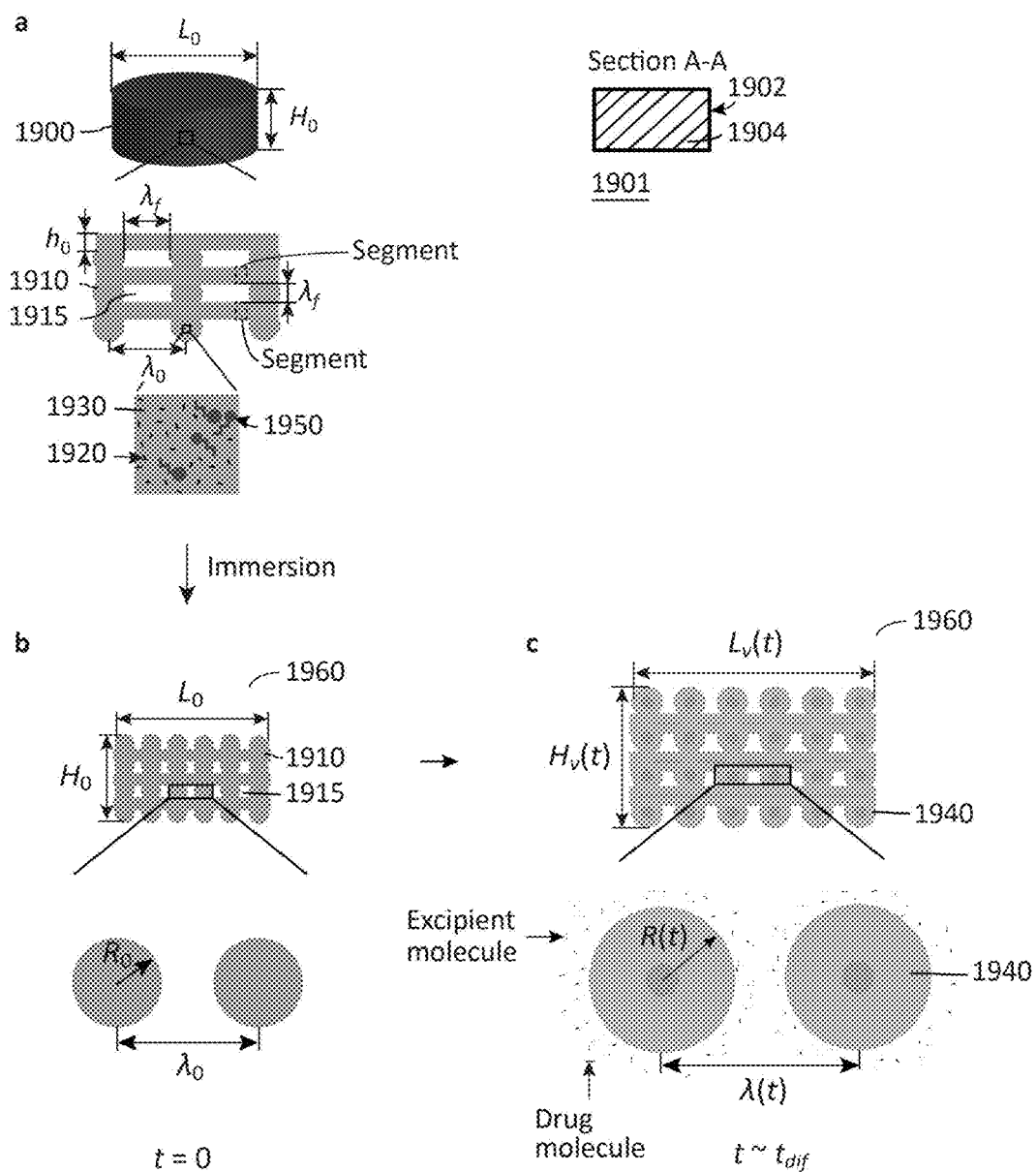
FIG. 19 presents non-limiting schematics of (a) the macro-, micro-, and molecular structure of a dosage form herein, (b) the structure of said dosage form at time t=0 min after immersion in a dissolution fluid, and (c) the structure of said expanded dosage form at time t~$t_{dif}$ after immersion in a dissolution fluid.

FIG. 19 presents a non-limiting example of a pharmaceutical dosage form 1900 comprising a drug-containing solid 1901 having an outer surface 1902 and an internal three dimensional structural framework 1904 of one or more substantially orderly arranged structural elements 1910. The framework 1904 is contiguous with and terminates at said outer surface 1902. The structural elements 1910 comprise segments spaced apart from adjoining segments 1910, thereby defining free spaces 1915. A plurality of adjacent free spaces 1915 combine to define one or more interconnected free spaces 1915 forming an open pore network that extends over a length at least half the thickness of the drug-containing solid 1901. The structural elements 1910 further comprise at least one sparingly-soluble active ingredient (e.g., at least one sparingly soluble drug) dissolved as drug molecules 1920 or dispersed as nanometer-scale aggregates in an excipient matrix 1930, 1950. Thus the drug forms a solid solution or a solid dispersion with said excipient matrix 1930, 1950. The excipient matrix 1930, 1950 comprises at least a water-soluble polymer carrier 1930 to carry the dissolved sparingly-soluble drug molecules 1920 or dispersed aggregates in the three dimensional structural framework of elements 1910. The excipient matrix 1930, 1950 further comprises at least an amphiphilic polymer 1950 for enhancing drug solubility in aqueous solutions.

Upon immersion in a dissolution fluid said open pore network permits percolation of physiological fluid 1960 into the drug-containing solid 1901, and enables uniform wetting of the structural framework by said fluid. In the invention herein, a surface (e.g., a surface of the three dimensional structural framework) is "wetted by a fluid" if said fluid contacts (e.g., is in contact with) said surface. A surface is "uniformly wetted" by a fluid if at least 30-60 percent of the area of said surface is in contact (e.g., in direct contact) with said fluid. In preferred embodiments, upon immersion of the drug-containing solid in a physiological fluid at least 60 percent (e.g., at least 70 percent or at least 80 percent) of the surface of the three dimensional structural framework is in direct contact with said fluid.

The drug-containing solid with uniformly wetted three-dimensional structural framework (e.g., the wet elements 1910 or wet drug-containing solid 1901) then transitions from solid 1930 to a viscous medium 1940, thereby expanding in all dimensions as shown schematically in the non-limiting FIG. 19b. In the non-limiting example of FIG. 19b, the length, $L_v$, and the thickness, $H_v$, of the expanding drug-containing solid are greater than the initial length, $L_0$, and the initial thickness, $H_0$.

It may be noted that the drug-containing solid may be a "solid", a combination of a "solid" and a "viscous medium", a "viscous medium", a combination of a "solid" and a dilute solution or dispersion, or a combination of a "viscous medium" and a dilute solution or dispersion while transitioning to a viscous medium. Moreover, the terms "expanding in all dimensions", "expand in all dimensions", or "expansion in all dimension" are understood as an increase in a length of a sample (e.g., the length, and/or width, and/or thickness, etc. of said sample) and an increase in volume of said sample. Thus, pure shear deformation is not considered "expansion in all dimensions" herein.

In some embodiments herein, therefore, the drug-containing solid or three-dimensional structural framework expands in all dimensions while transitioning to viscous. In some embodiments, moreover, the drug-containing solid or three-dimensional structural framework expands due to the penetration of physiological/body fluid into the three dimensional structural framework of one or more elements or into a water-soluble polymer carrier. The expansion of the drug-containing solid can be quite substantial. Thus, in some embodiments, at least one dimension of the drug-containing solid (e.g., a side length of the drug-containing solid, the thickness of the drug-containing solid, etc.) expands to at least 1.12 times the initial value (e.g., the initial length) while transitioning to a viscous medium. This includes, but is not limited to at least one dimension of the drug-containing solid expanding to at least 1.15 times, or at least 1.17 times, or at least 1.2 times, or at least 1.22 times, or at least 1.25 times, or at least 1.27 times, or at least 1.3 times, or at least 1.35 times, or at least 1.4 times, or at least 1.5 times, or at least 1.6 times, or at least 1.7 times the initial value while transitioning to a fluidic or viscous medium.

Furthermore, in some embodiments the drug-containing solid expands to at least 1.3 times its initial volume while transitioning to a viscous medium. This includes, but is not limited to a drug-containing solid that expands to at least 1.4 times, or at least 1.5 times, or at least 1.6 times, or at least 1.7 times, or at least 1.8 times, or at least 1.9 times, or at least 2 times its initial volume while transitioning to a viscous medium.

The rate of expansion generally depends on the rate at which dissolution fluid is absorbed by the structural framework (e.g., by the excipient), and the presence and stringency of constraints to expansion. The absorption rate of dissolution fluid by the framework is typically increased if the specific surface area (e.g., the surface area to volume ratio) of the framework is increased. Thus, if the elements are thin, the surface area to volume ratio is large, and the rate at which dissolution fluid is absorbed by the framework should be fast.

Constraints to expansion often originate from non-uniformities in the dissolution fluid concentration across the three dimensional structural framework. By way of example but not by way of limitation, a wet element or segment may absorb dissolution fluid, but expansion of said wet element or segment may be constrained if it is connected (e.g., attached) to a dry solid element or segment that does not expand. Thus, to minimize constraints to expansion, uniform wetting of elements in the structural framework is crucial. Uniform wetting is enabled, among others, by interconnected free spaces (e.g., by interconnected free spaces forming an open pore network into which dissolution fluid may percolate).

The dosage forms according to the invention herein comprise a structural framework of thin elements with hydrophilic surface composition surrounded by interconnected free spaces that form an open pore network. Thus the expansion rate can be substantial.

In some embodiments, accordingly, at least one dimension (e.g., a side length or the thickness) of the drug-containing solid expands to at least 1.12 times the initial value (e.g., the initial length) as it transitions to a fluidic or viscous medium within no more than 30 minutes of immersion in a physiological or body fluid under physiological conditions. This includes, but is not limited to at least one dimension of the drug-containing solid reaching a length at least 1.12 times the initial length within no more than 20 minutes, or within no more than 15 minutes, or within no more than 10 minutes, or within no more than 5 minutes of immersion in a physiological or body fluid under physiological conditions. This also includes, but is not limited to at least one dimension of the drug-containing solid expanding to a length at least 1.15 times the initial length, or at least 1.2 times the initial length, or at least 1.25 times the initial length, or at least 1.3 times the initial length, or at least 1.4 times the initial length, or at least 1.5 times the initial length, or at least 1.6 times the initial length within no more than 20 minutes after immersion in a physiological or body fluid under physiological conditions.

Furthermore, in some embodiments the drug-containing solid expands to at least 1.3 times its initial volume within no more than 20 minutes of immersing in a physiological or body fluid under physiological conditions. This includes, but is not limited to a drug-containing solid that expands to at least 1.4 times, or at least 1.5 times, or at least 1.6 times, or at least 1.7 times, or at least 1.8 times, or at least 1.9 times, or at least 2 times its initial volume within no more than 20-30 minutes of immersing in a physiological or body fluid under physiological conditions.

In some embodiments, moreover, the drug-containing solid expands isotropically while transitioning to a viscous medium. For further information related to isotropic expansion of a drug-containing solid, see, e.g., the International Application No. PCT/US19/19004 filed on Feb. 21, 2019 and titled "Expanding structured dosage form".

e) Drug Release and Mechanical Properties of Drug-Containing Solid and Dosage Form In some embodiments, the drug-containing solid dissolves or disintegrates during or after transitioning to a viscous medium. Thus, in some embodiments, eighty percent of the drug content in the drug-containing solid is released in less than 45 minutes after immersion in a physiological or body fluid under physiological conditions. This includes, but is not limited to a drug-containing solid that releases eighty percent of the drug content in less than 40 minutes, or in less than 35 minutes, or in less than 30 minutes, or in less than 25 minutes, or in less than 20 minutes, or in less than 15 minutes, or in less than 10 minutes, or in 1-45 minutes, 1-30 minutes, 2-45 minutes, or 2-30 minutes after immersion in a physiological fluid under physiological conditions.

In some embodiments, moreover, upon immersion of the drug-containing solid in a physiological/body fluid, where the drug mass in the drug-containing solid per unit volume of the dissolution fluid is greater than the terminal drug solubility, the fluid supersaturates with drug. Thus, in some embodiments, a sparingly-soluble drug supersaturates in a physiological/body fluid upon immersion of the dosage form in said fluid under physiological conditions, where the mass of said sparingly-soluble drug in the dosage form is greater than the product of solubility and fluid volume.

In some embodiments, moreover, a sparingly-soluble drug supersaturates in a physiological/body fluid to a maximum supersaturation at least 1.5 upon immersion of the dosage form in said fluid under physiological conditions where the product of solubility and fluid volume is smaller than 0.5 times the mass of said sparingly-soluble drug in the dosage form.

In some embodiments, the tensile strength of at least one element is greater than 0.01 MPa (e.g., greater than 0.05 MPa or greater than 0.1 MPa). In some embodiments, the tensile strength of the drug containing solid or three dimensional structural framework is greater than 0.01 MPa (e.g., greater than 0.05 MPa or greater than 0.1 MPa).

Aspects of the Method

Figure 20:
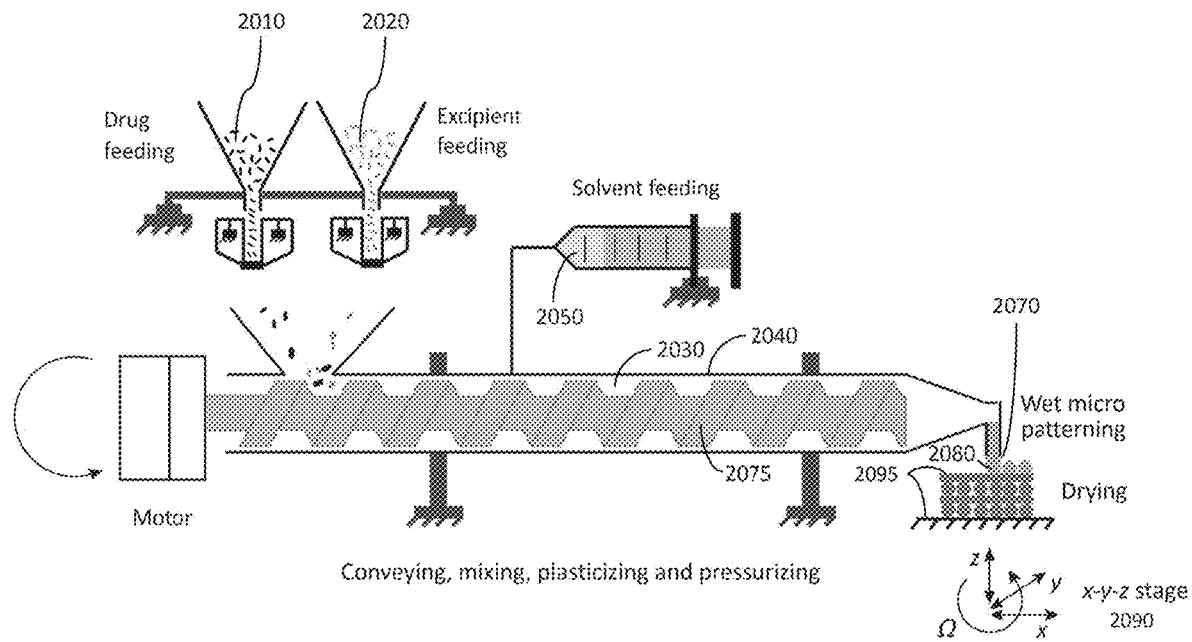
FIG. 20 is a non-limiting schematic of a solvent-based method of manufacturing dosage forms according to this invention.
Figure 20:
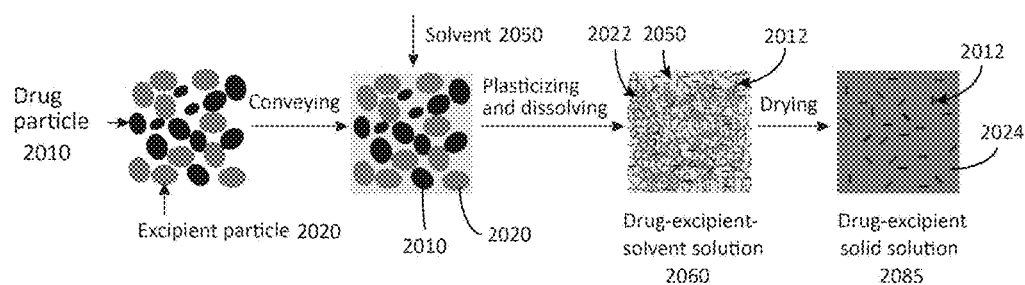

FIG. 20 presents a non-limiting example of a method of manufacturing the dosage forms disclosed. Granules of at least one sparingly-soluble drug 2010 and at least one water-soluble excipient 2020 are injected (e.g., fed, delivered, etc.) into an extrusion channel 2030 having a cross section extending along its length inside a housing 2040. Furthermore, at least one solvent 2050 is injected into said extrusion channel 2030. The solvent 2050 solvates the least one injected excipient granule 2020 and the least one sparingly-soluble drug granule 2010 dissolves (e.g., is soluble) in said solvated excipient to form a plasticized solution 2060 of sparingly-soluble drug molecules 2012, water-soluble excipient molecules 2022, and solvent 2050. The plasticized solution 2060 is conveyed towards an exit port 2070 of the extrusion channel 2030 by applying mechanical work on the plasticized solution 2060. Then the plasticized solution 2060 is extruded through an exit port 2070 to form at least one plasticized element 2080. At least one plasticized element 2080 is subsequently structured to a three dimensional structural framework of one or more drug-containing elements. One or more drug-containing elements are then solidified to form a solid solution 2085 of sparingly-soluble drug molecules 2012 (or drug nano-particles or other nanometer-scale aggregates of drug and excipient) embedded in a solid matrix of water-soluble excipient 2024.

In some embodiments, the method of manufacturing the dosage forms disclosed further comprises injecting or feeding at least one amphiphilic polymer into an extrusion channel 2030.

In some embodiments, mechanical work is applied on the plasticized solution 2060 by a conveying element 2075. In some embodiments, said conveying element 2075 comprises at least one screw or at least one piston.

In some embodiments, moreover, plasticized solution or dispersion is extruded through at least one exit port of the extrusion channel by an advancing piston.

In some embodiments, at least one plasticized element 2080 is a plasticized fiber. Furthermore, in some embodiments at least one drug-containing element is a drug-containing fiber.

In some embodiments, moreover, plasticized solution or dispersion is extruded through at least one exit port of the extrusion channel designed to form a fibrous extrudate comprising at least one plasticized fiber having a fiber thickness less than 2.5 mm (e.g., less than 2 mm, or less than 1.5 mm, or in the ranges 1 µm-2.5 mm; 2.5 µm-2 mm; 5 µm-1.5 mm; or 10 µm-1.5 mm).

Moreover, in some embodiments structuring at least one plasticized element 2080 to a three dimensional structural framework or network of one or more elements is performed using a translating or rotating stage 2090. By way of example but not by way of limitation, one or more plasticized elements 2080 may be structured to a three dimensional structural framework or network of elements by 3D-patterning said one or more plasticized elements 2080 on a substrate 2095 defined by or attached to a translating or rotating stage 2090. It may be noted that the terms "stage", "x-y-z stage", "translating or rotating stage", and "translating stage" are used interchangeably in this disclosure.

Figure 21:
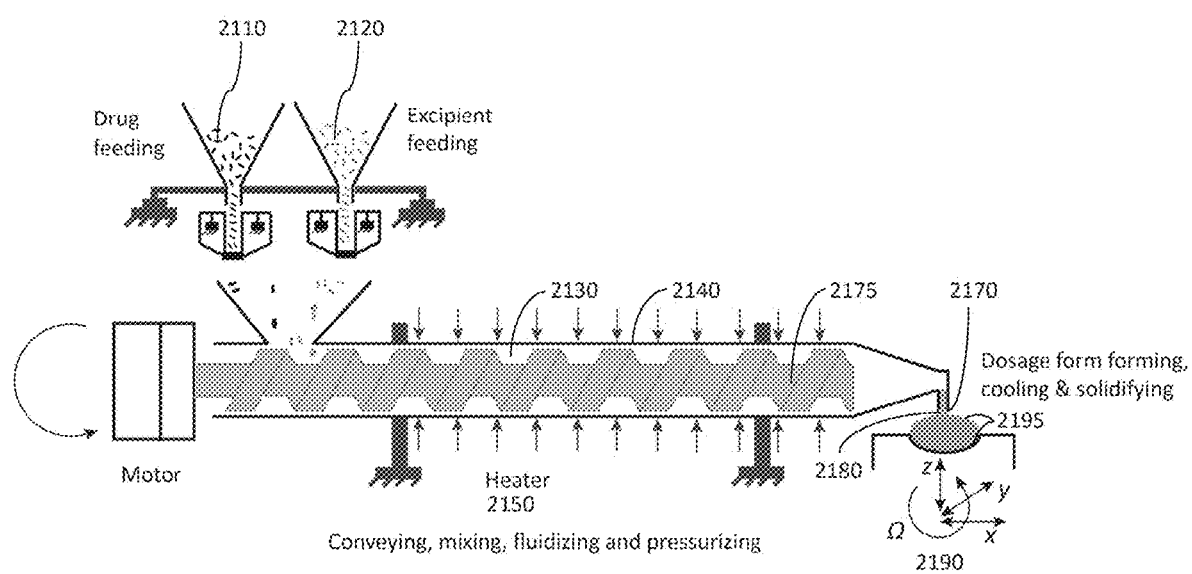
FIG. 21 is another schematic of a method of manufacturing dosage forms according to this invention.
Figure 21:
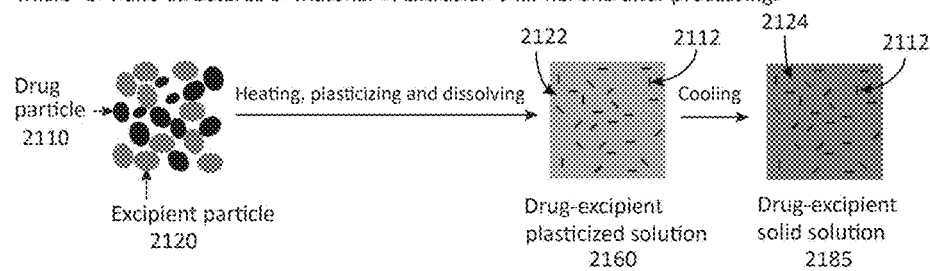

FIG. 21 presents another non-limiting example of a method of manufacturing the dosage forms disclosed. Granules of at least one sparingly-soluble drug 2110 and at least one thermoplastic, water-soluble excipient 2120 in which said sparingly-soluble drug 2110 is soluble are injected into an extrusion channel 2130 having a cross section extending along its length inside a housing 2140. The injected granules 2110, 2120 are heated to plasticize at least one thermoplastic, water-soluble excipient granule 2120. At least one sparingly-soluble drug granule dissolves in said plasticized excipient to form a plasticized solution 2160 of plasticized excipient 2122 and drug molecules 2112. The plasticized solution 2160 is conveyed towards an exit port 2170 of the extrusion channel 2130 by applying mechanical work on the plasticized solution 2160. The plasticized solution 2160 is further extruded through an exit port 2170 to form at least one plasticized element 2180. At least one plasticized element 2180 is then structured to a three dimensional structural framework of one or more drug-containing elements. The elements are subsequently solidified by cooling to below their melting temperature forming a solid solution 2185 of drug molecules 2112 (or drug nano-particles or other nanometer-scale aggregates of drug and excipient) embedded in a water-soluble, solid excipient matrix 2124.

In some embodiments, the method of manufacturing the dosage forms disclosed further comprises injecting or feeding at least one amphiphilic polymer into an extrusion channel 2130.

In some embodiments, the method of manufacturing the dosage forms disclosed further comprises blending at least a water-soluble polymer carrier, at least an amphiphilic polymer, and at least a sparingly-soluble drug to form a uniform mixture or plasticized solution or dispersion.

In some embodiments, mechanical work is applied on the plasticized solution 2160 by a conveying element 2175. In some embodiments, said conveying element 2175 comprises at least one screw or at least one piston.

In some embodiments, moreover, plasticized solution or dispersion is extruded through at least one exit port of the extrusion channel by an advancing piston.

In some embodiments, at least one plasticized element 780 is a plasticized fiber. Furthermore, in some embodiments at least one drug-containing element is a drug-containing fiber.

In some embodiments, moreover, plasticized solution or dispersion is extruded through at least one exit port of the extrusion channel designed to form a fibrous extrudate comprising at least one plasticized fiber having a fiber thickness less than 2.5 mm (e.g., less than 2 mm, or less than 1.5 mm, or in the ranges 1 µm-2.5 mm; 2.5 µm-2 mm; 5 µm-1.5 mm; or 10 µm-1.5 mm).

Moreover, in some embodiments structuring at least one plasticized element 2180 to a three dimensional structural framework or network of one or more elements is performed using a translating or rotating stage 2190. By way of example but not by way of limitation, one or more plasticized elements 2180 may be structured to a three dimensional structural framework or network of elements by 3D-patterning said one or more plasticized elements 2180 on a substrate 2195 defined by or attached to a translating or rotating stage 2190.

Figure 22:
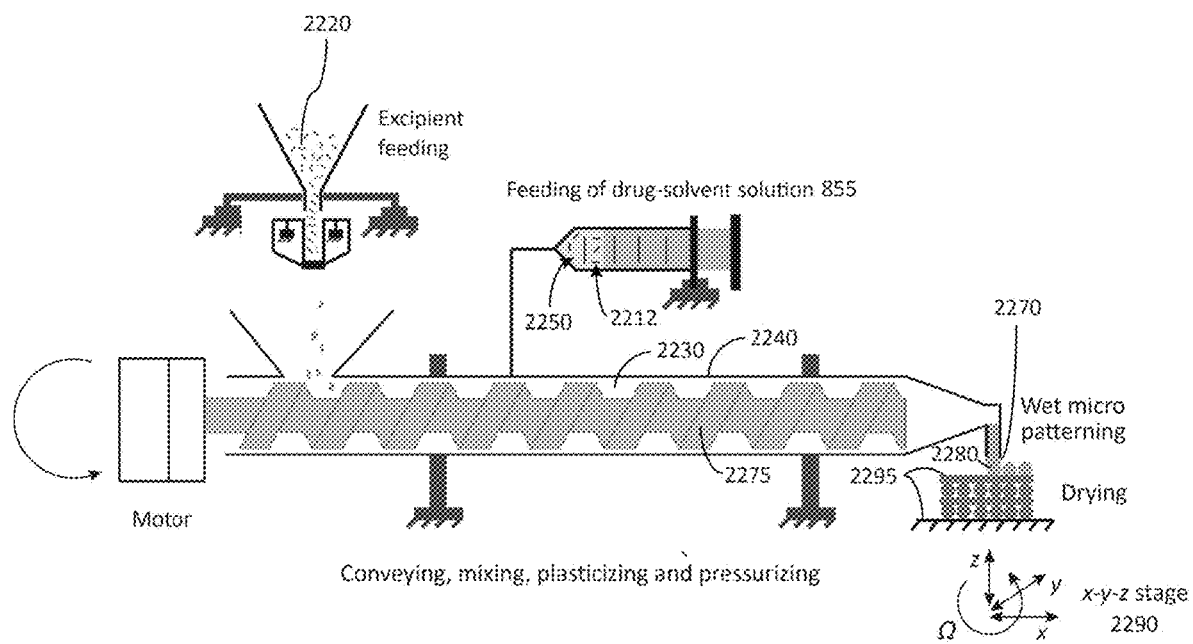
FIG. 22 is another schematic of a solvent-based method of manufacturing dosage forms according to this invention.
Figure 22:
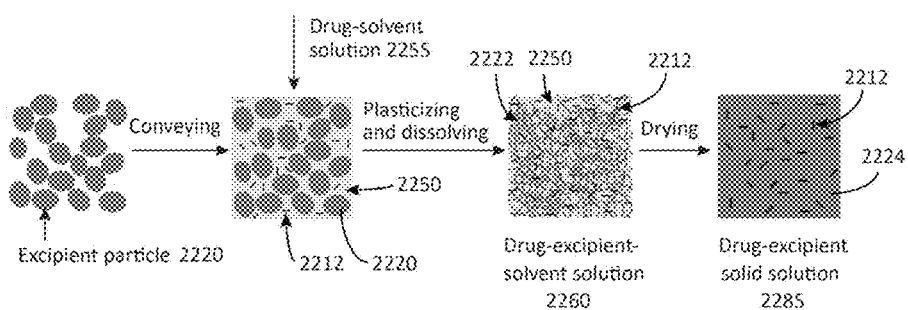

FIG. 22 shows another non-limiting example of a method of manufacturing the dosage forms disclosed. Granules of at least one water-soluble excipient 2220 are injected into an extrusion channel 2230 having a cross section extending along its length inside a housing 2240. Furthermore, at least one drug-solvent solution 2255 comprising solvent 2250 and dissolved molecules of at least one sparingly-soluble drug 2212 is injected into said extrusion channel 2230. The drug-solvent solution 2255 further solvates the least one injected, water-soluble excipient granule 2220 to form a plasticized solution 2260 of sparingly-soluble drug molecules 2212, water-soluble excipient molecules 2222, and solvent 2250. The plasticized solution 2260 is conveyed towards an exit port 2270 of the extrusion channel 2230 by applying mechanical work on the plasticized solution 2260. Then the plasticized solution 2260 is extruded through an exit port 2270 to form at least one plasticized element 2280. At least one plasticized element 2280 is subsequently structured to a three dimensional structural framework of one or more drug-containing elements. One or more drug-containing elements are then solidified to form a solid solution 2290 of sparingly-soluble drug molecules 2212 (or drug nanoparticles or other nanometer-scale aggregates of drug and excipient) embedded in a solid matrix of water-soluble excipient 2224.

In some embodiments, the method of manufacturing the dosage forms disclosed further comprises injecting or feeding at least one amphiphilic polymer into an extrusion channel 2230.

In some embodiments, the method of manufacturing the dosage forms disclosed further comprises blending at least a water-soluble polymer carrier, at least an amphiphilic polymer, and at least a sparingly-soluble drug to form a uniform mixture or plasticized solution or dispersion.

In some embodiments, mechanical work is applied on the plasticized solution 2260 by a conveying element 2275. In some embodiments, said conveying element 2275 comprises at least one screw or at least one piston.

In some embodiments, moreover, plasticized solution or dispersion is extruded through at least one exit port of the extrusion channel by an advancing piston.

In some embodiments, at least one plasticized element 880 is a plasticized fiber. Furthermore, in some embodiments at least one drug-containing element is a drug-containing fiber.

In some embodiments, moreover, plasticized solution or dispersion is extruded through at least one exit port of the extrusion channel designed to form a fibrous extrudate comprising at least one plasticized fiber having a fiber thickness less than 2.5 mm (e.g., less than 2 mm, or less than 1.5 mm, or in the ranges 1 μm-2.5 mm; 2.5 μm-2 mm; 5 μm-1.5 mm; or 10 μm-1.5 mm).

Furthermore, in some embodiments structuring at least one plasticized element 2280 to a three dimensional structural framework or network of one or more elements is performed using a translating or rotating stage 2290. By way of example but not by way of limitation, one or more plasticized elements 2280 may be structured to a three dimensional structural framework or network of elements by 3D-patterning said one or more plasticized elements 2280 on a substrate 2295 defined by or attached to a translating or rotating stage 2290.

Figure 23:
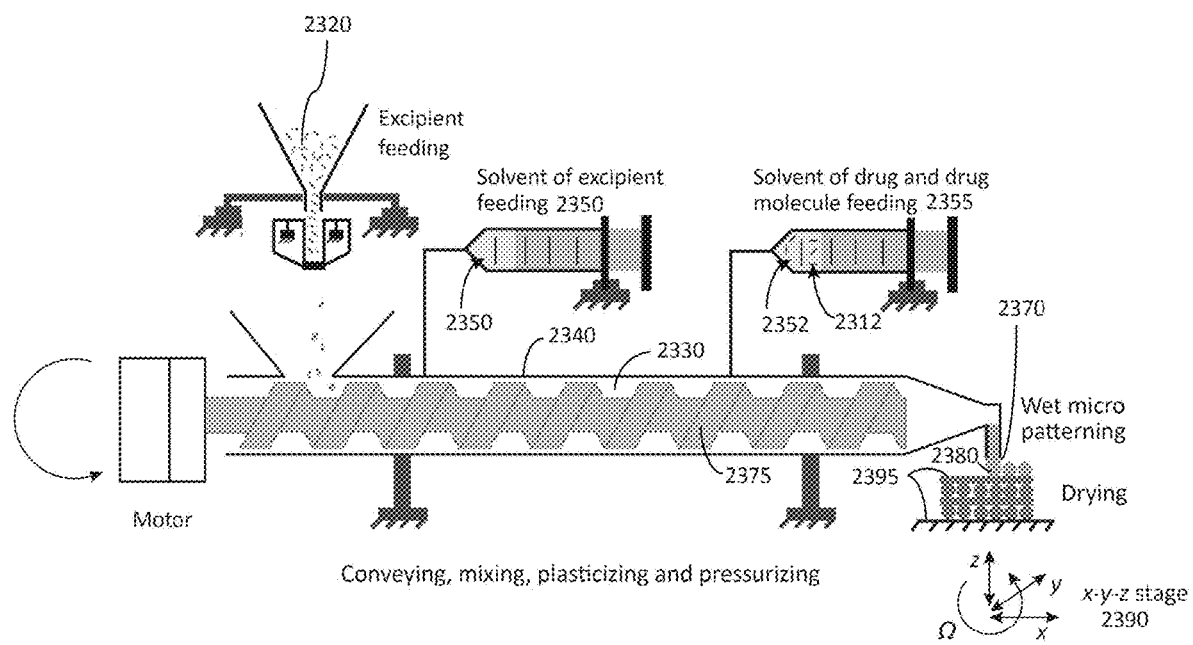
FIG. 23 shows yet another schematic of a solvent-based method of manufacturing dosage forms according to this invention.
Figure 23:
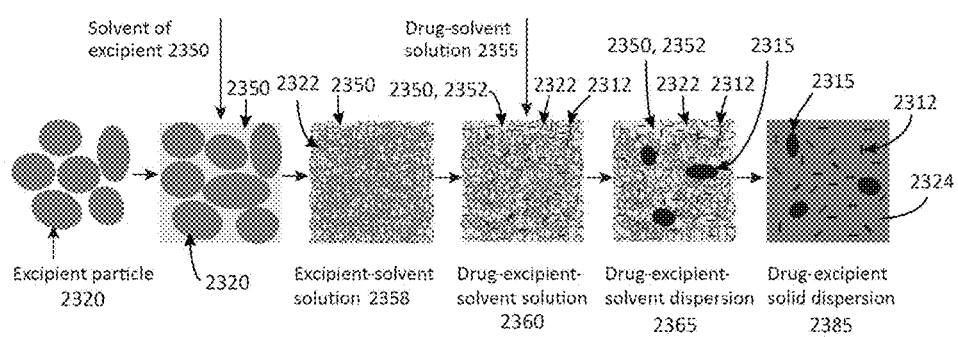

FIG. 23 presents another non-limiting example of a method of manufacturing the dosage forms disclosed. Granules of at least one water-soluble excipient 2320 are injected into an extrusion channel 2330 having a cross section extending along its length inside a housing 2340. Furthermore, at least a first solvent 2350 in which at least one injected excipient 2320 is soluble is injected into the extrusion channel 2330. In some embodiments, an injected excipient 2320 and first solvent 2350 may form a plasticized excipient-solvent solution 2358 comprising solvated molecules of at least one excipient 2322 and first solvent 2350. Moreover, at least a drug-solvent solution 2355 comprising a second solvent 2352 and dissolved molecules of at least one sparingly-soluble drug 2312 is injected into said extrusion channel 2330 to form a plasticized drug-excipient-solvent solution 2360. The plasticized drug-excipient-solvent solution 2360 is also referred to herein as "plasticized solution". The plasticized solution 2360 is conveyed towards an exit port 2370 of the extrusion channel 2330 by applying mechanical work on the plasticized solution 960. Within the plasticized solution 2360, drug molecules may aggregate as particles (e.g., drug particles, etc.) 2315 to form a drug-excipient-solvent dispersion 2365. In the context herein, both a "plasticized drug-excipient-solvent solution 2360" and a "plasticized drug-excipient-solvent dispersion 2365" are referred to as "plasticized mixture". The plasticized mixture is extruded through an exit port 2370 to form at least one plasticized element 2380. At least one plasticized element 2380 is subsequently structured to a three dimensional structural framework of one or more drug-containing elements. One or more drug-containing elements are then solidified to form a solid solution or a solid dispersion 2385 of sparingly-soluble drug molecules 2312 or sparingly-soluble agglomerates of drug molecules 2315 embedded in a solid matrix of water-soluble excipient 2324.

In some embodiments, the method of manufacturing the dosage forms disclosed further comprises injecting or feeding at least one amphiphilic polymer into an extrusion channel 2330.

In some embodiments, the method of manufacturing the dosage forms disclosed further comprises blending at least a water-soluble polymer carrier, at least an amphiphilic polymer, and at least a sparingly-soluble drug to form a uniform mixture or plasticized solution or dispersion.

In some embodiments, mechanical work is applied on the plasticized mixture by a conveying element 2375. In some embodiments, said conveying element 2375 comprises at least one screw or at least one piston.

In some embodiments, moreover, plasticized solution or dispersion is extruded through at least one exit port of the extrusion channel by an advancing piston.

In some embodiments, at least one plasticized element 980 is a plasticized fiber. Furthermore, in some embodiments at least one drug-containing element is a drug-containing fiber.

In some embodiments, moreover, plasticized solution or dispersion is extruded through at least one exit port of the extrusion channel designed to form a fibrous extrudate comprising at least one plasticized fiber having a fiber thickness less than 2.5 mm (e.g., less than 2 mm, or less than 1.5 mm, or in the ranges 1 μm-2.5 mm; 2.5 μm-2 mm; 5 μm-1.5 mm; or 10 μm-1.5 mm).

Thus, in some embodiments the diameter or size of hydraulic diameter or effective diameter of the exit port is less than 2.5 mm (e.g., less than 2 mm, or less than 1.5 mm, or in the ranges 1 μm-2.5 mm; 2.5 μm-2 mm; 5 μm-1.5 mm; or 10 μm-1.5 mm).

Furthermore, in some embodiments structuring at least one plasticized element 2380 to a three dimensional structural framework or network of one or more elements is performed using a translating or rotating stage 2390. By way of example but not by way of limitation, one or more plasticized elements 2380 may be structured to a three dimensional structural framework or network of elements by 3D-patterning said one or more plasticized elements 2380 on a substrate 2395 defined by or attached to a translating or rotating stage 2390.

It may be obvious to a person of ordinary skill in the art that many more examples of the method to manufacture the disclosed dosage form could be presented. By way of example but not by way of limitation, another non-limiting example to produce the dosage form is to prepare a filament comprising dispersed drug molecules in an excipient (e.g., by extrusion). Said filament could then be 3D-printed (or 3D-patterned or 3D-micro-patterned) to a dosage form comprising a solid-solution framework of one or more drug-containing elements. Moreover, in some embodiments, plasticized matrix or plasticized solution (e.g., comprising drug, excipient, and solvent) is fed into an extrusion channel, conveyed towards an exit port of said extrusion channel, and patterned to a fibrous structure. For further details/examples, see, e.g., the U.S. application Ser. No. 15/964,058 titled "Method and apparatus for the manufacture of fibrous dosage forms. Any more examples of methods to manufacture the dosage form disclosed obvious to a person of ordinary skill in the art are included in the scope of this invention.

Embodiments of the Method of Manufacture

Figure 24:
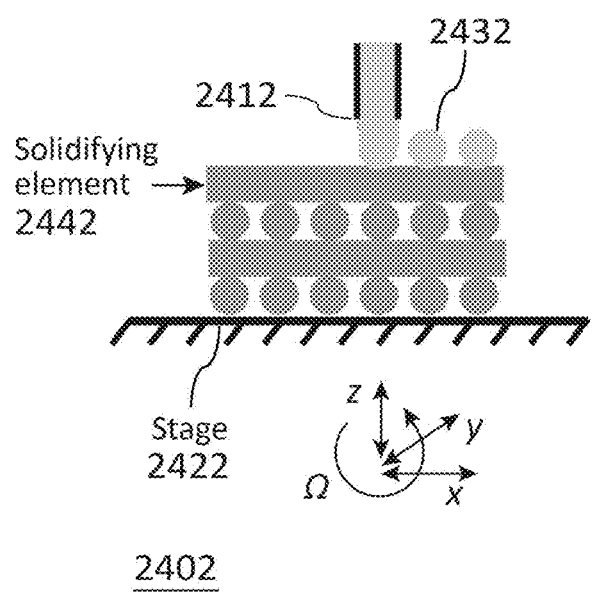
FIG. 24 is a non-limiting schematic illustrating 3D-micro-patterning of elements on a moving substrate or stage to form a three-dimensional structural framework.

FIG. 24 presents a non-limiting schematic 2402 of how one or more plasticized elements 2432 may be structured to a three dimensional structural framework of one or more elements. One or more plasticized elements 2432 are 3D-patterned on a substrate defined by a stage 2422 or attached to a stage 2422. The distance between the exit port 2412 and the deposition location of a plasticized element 2432 effluent from said exit port 2412 is small and controlled during 3D-patterning. Thus the one or more plasticized elements 2432 effluent from the exit port 2412 do not bend randomly (or almost randomly) before deposition. The deposition location of the one or more plasticized elements 2432 effluent from the exit port 2412 can be precisely controlled as shown. Such precise control of the plasticized fibers' deposition location enables the manufacture of dosage forms with precisely controlled microstructure.

In some embodiments, therefore, the structuring of at least one plasticized element to a three dimensional structural network of one or more elements is performed by 3D-patterning said at least one plasticized fiber on a substrate.

In some embodiments, moreover, the substrate is defined by or attached to a movable stage.

In some embodiments, the stage is movable (e.g., translatable and/or rotatable) in at least two directions relative to the at least one exit port for depositing one or more plasticized fibers along a path defined by the motion of said stage.

In some embodiments, the stage is movable (e.g., translatable and/or rotatable) in at least three directions relative to the at least one exit port for depositing one or more plasticized fibers along a path defined by the motion of said stage.

In some embodiments, two directions in which the stage is movable span a plane oriented at an angle to the central axis of the extruded fiber to pattern said fiber on a substrate defined by or attached to said stage, and wherein said stage is further movable in a third direction oriented at an angle to said plane to control the distance between said substrate and an exit port.

Furthermore, for achieving precise control of a plasticized element's deposition location, in some embodiments the distance between an exit port and the deposition location of a plasticized element effluent from said exit port is no greater than 7 mm during 3D-patterning. This includes, but is not limited to a distance between an exit port and the deposition location of a plasticized element effluent from said exit port no greater than 6 mm, or no greater than 5 mm, or no greater than 4 mm, or no greater than 3 mm, or no greater than 2 mm. Furthermore, in some embodiments the distance between an exit port and a deposition location of a plasticized element on a substrate is no greater than ten times the thickness of said element. This includes, but is not limited to a distance between an exit port and a deposition location of an element on a substrate no greater than 9 times, or no greater than 8 times, or no greater than 7 times, or no greater than 6 times, or no greater than 5 times the thickness of said element. It may be noted that the deposition location of a plasticized element can be the surface of a substrate (e.g., the top surface of an x-y-z stage or the top surface of a deposited fibrous bed or structure, etc.).

Moreover, for achieving precisely controlled patterns of one or more elements, the velocity of a substrate with respect to an exit port may be of the order of the velocity of an extrudate effluent from an exit port (e.g., the velocity of a plasticized element that exits an exit port or the velocity of an extrudate). Thus, in some embodiments the velocity of a substrate with respect to an exit port, $v_{st}$, is in the range 0.1-10 times the velocity of an extrudate, $v_e$. This includes, but is not limited to $v_{st}$ in the range 0.2-5 times $v_e$, or $v_{st}$ in the range 0.3-3 times $v_e$, or $v_{st}$ in the range 0.5-2 times $v_e$. It may be obvious to a person of ordinary skill in the art that the path and velocity of a substrate with respect to an exit port may be computer-controlled.

In addition to the requirements on the kinematics of a substrate with respect to an exit port, a plasticized element should be viscous enough to ensure that a precise pattern is preserved. Thus, in some embodiments the shear viscosity of a plasticized matrix or element is greater than 0.1 Pa·s at a shear rate no greater than 10 1/s. This includes, but is not limited to a shear viscosity of a plasticized matrix or element greater than 0.5 Pa·s, or greater than 1 Pa·s, or greater than 5 Pa·s, or greater than 10 Pa·s, or greater than 20 Pa·s, or greater than 50 Pa·s, or greater than 100 Pa·s, or greater than 200 Pa·s, or greater than 500 Pa·s at a shear rate no greater than 10 1/s.

In some embodiments, the viscosity of a plasticized element is controlled by the weight fraction of solvent in said element. Thus, in some embodiments, the weight fraction of solvent in a plasticized element is no greater than 0.925. This includes, but is not limited to a weight fraction of solvent in a plasticized element no greater than 0.9, or no greater than 0.85, or no greater than 0.8, or no greater than 0.75, or no greater than 0.7, or no greater than 0.65, or no greater than 0.6.

In some embodiments, an inter-fiber spacing, and/or a fiber thickness, and/or the position of an inter-fiber contact, and/or the contact width of an inter-fiber contact can be precisely (or deterministically) controlled in a fibrous dosage form prepared by the method herein.

After patterning on a substrate, a plasticized element may be solidified. In the invention herein, solidification of a plasticized element is referred to as increasing the viscosity of said plasticized element by at least two times. This includes, but is not limited to increasing the viscosity of said plasticized element by at least three times, or by at least four times, or by at least five times, or by at least six times, or by at least seven times, or by at least ten times, or by at least 20 times. In the extreme case, the viscosity of a solidified element is very large and may be considered "infinite". In this extreme case, the solidified element can be considered an "elastic" material.

A plasticized element may be solidified by various ways. By way of example but not by way of limitation, depending on the composition of said plasticized element, solidification may be by evaporating solvent, or by cooling (e.g., by cooling the plasticized element to below its melting temperature), or by cross-linking some of the constituents.

It may be noted that an apparatus capable of producing the dosage forms disclosed by performing any of the methods disclosed in this specification or in the cited references is also claimed herein.

Further non-limiting embodiments of methods and apparatuses for the manufacture of the dosage form disclosed are presented in U.S. application Ser. No. 15/482,776 titled "Fibrous dosage form", U.S. application Ser. No. 15/964,058 titled "Method and apparatus for the manufacture of fibrous dosage forms", and U.S. application Ser. No. 15/964,063 and titled "Dosage form comprising two-dimensional structural elements".

EXPERIMENTAL EXAMPLES

The following examples present ways by which the fibrous dosage forms may be prepared and analyzed, and will enable one of skill in the art to more readily understand the principle thereof. The following examples are presented by way of illustration and are not meant to be limiting in any way.

Single Fiber Experiments

Example 1: Preparation of Solid-Solution Single Fibers

As-received ibuprofen drug particles (BASF, Ludwigshafen, Germany) were first dissolved in the solvent DMSO. The solution was then combined with the excipient, either hydroxypropyl methylcellulose (HPMC) with a molecular weight of 10 kg/mol or a mixture of 67 wt % HPMC and 33 wt % polyoxyl stearate (Tradename: Gelucire 48/16, Gattefosse). The mixture was extruded by a desktop extruder to form a uniform, viscous fiber. The volume of solvent in the viscous fiber per unit mass of HPMC was 1.25 l/kg. The drug weight fraction with respect to the combined mass of drug and excipient, $w_d$, ranged from 0.025 to 0.4. The viscous fiber was then deposited on a flat surface and warm air at a temperature of 60° C., and a velocity of 2.3 m/s was blown on it to evaporate the solvent. The fiber was dried for 35 minutes.

Example 2: Fiber Drying Experiments

For estimating the drying time, a viscous HPMC-ibuprofen fiber with drug weight fraction, $w_d$=0.025, was prepared as above and deposited in a weighing boat. The fiber was then exposed to a stream of air at a temperature of 60° C., and velocity of 2.3 m/s. The weight of the fiber was measured at different times after exposure to the air stream. The fraction of residual solvent at time t was determined as $[w(t)-w_\infty]/[w_0-w_\infty]$, where w(t) is the weight of the fiber at time t, $w_0$ the initial weight of the wet fiber, and $w_\infty$ the weight of dry fiber.

Figure 25:
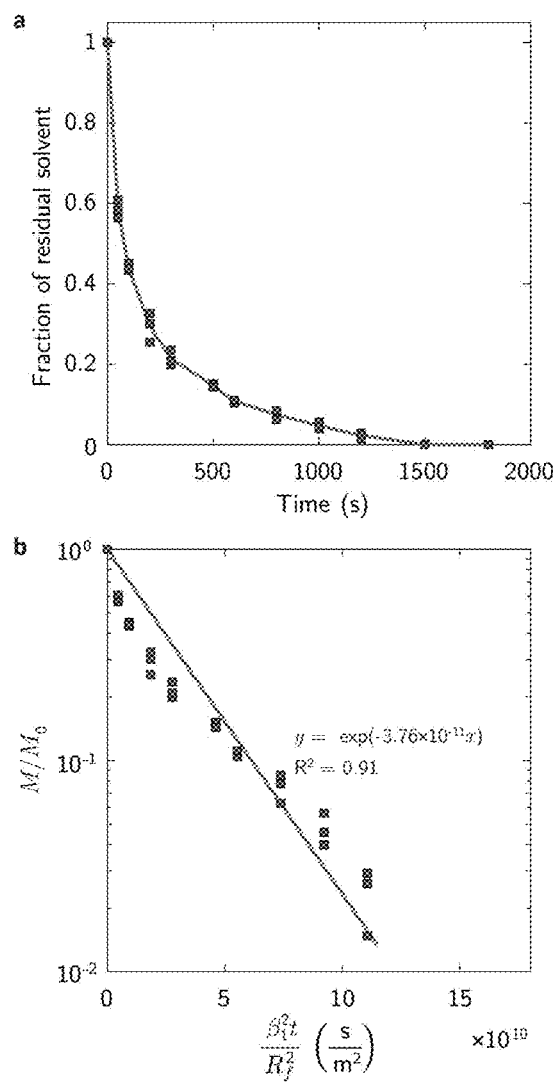
FIG. 25 shows results of drying rate of HPMC-2.5 wt % ibuprofen fibers: (a) fraction of residual solvent versus time, and (b) semi-log plot of the fraction of residual solvent, $M(t)/M_0$, versus $\beta_1^2 t/R_f^2$.

FIG. 25a shows the fraction of residual solvent in the fiber (the ratio of the mass of solvent in the wet HPMC-ibuprofen fibers at time t, M(t), and that initially, $M_0$) versus time after exposure to a hot air stream (temperature=60° C., velocity=2.3 m/s). Initially, $M(t)/M_0$ decreased rapidly with time, and then gradually approached the final value zero.

It was previously reported that if evaporation of the solvent is diffusion-controlled in the interior, $M(t)/M_0$ may be expressed as:

$$\frac{M(t)}{M_0} \cong \exp(-\beta_1^2 D_l t/R_f^2) \quad (17)$$

where $\beta_1$ is a constant (about 2.4 in diffusion-controlled evaporation), DI the diffusion coefficient of solvent in the fiber, and Ry the initial radius of the wet fiber.

FIG. 15b, a semi-log plot of $M(t)/M_0$ versus $\beta_1^2 t/R_f^2$, validates the model. $M(t)/M_0$ decays exponentially with $D_t$=3.76×10$^{-11}$ m²/s. Minor deviations from the model may be due to structural changes in the fiber during drying.

Example 3: Scanning Electron Microscopy (SEM)

The micro- and nano-structures of the fibers were imaged using a Zeiss Merlin High Resolution SEM with a GEMINI column. Prior to imaging the cross sections, the fibers were cut with a thin blade (MX35 Ultra, Thermo Scientific, Waltham, MA). Imaging was done with an in-lens secondary electron detector. Low-magnification images were taken at an accelerating voltage of 5 kV and a probe current of 95 pA. High-magnification images were taken at 1 kV and 80 pA, respectively.

Ibuprofen particles were imaged with the same microscope. The as-received particles were sieved with a 200 mesh screen (size of openings: 74 µm) before imaging. The microscope was operated at an accelerating voltage of 1 kV and a probe current of 80 pA.

Figure 26:
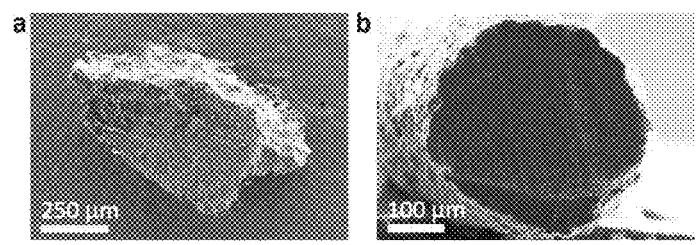
FIG. 26 presents results of scanning electron micrographs of particles and fibers: (a) drug particle and (b) cross-section of a fiber.

FIG. 26a is a scanning electron micrograph of the drug particles. The particles were non-spherical, and their size was roughly 20 µm. FIG. 26b is a representative low-magnification image of the cross-section of a dried HPMC-ibuprofen fiber with $w_d$=0.025. The structure was uniform and minimally-porous at this scale. The radius of the fiber was about 179 µm and the circular shape was preserved upon drying.

Figure 27:
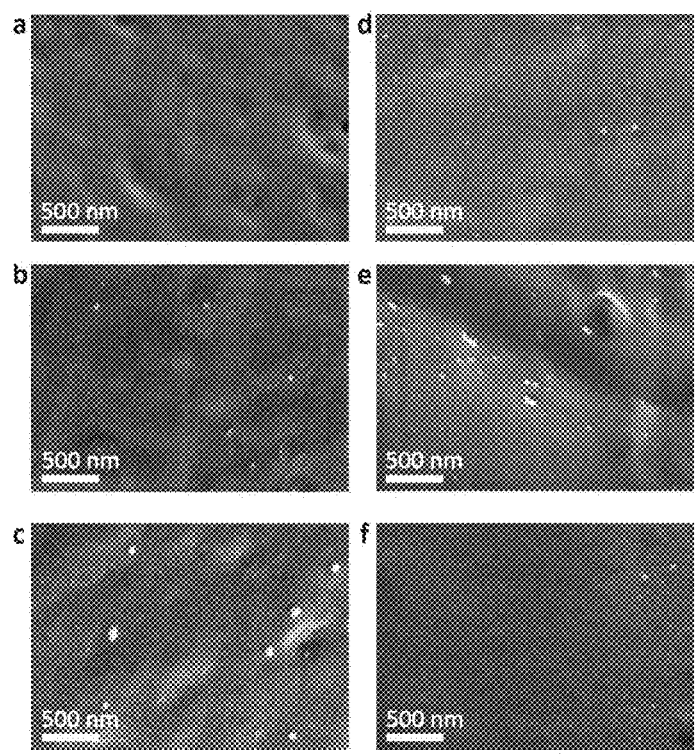
FIG. 27 displays non-limiting scanning electron micrographs of the nano-structures of fibers: (a-c) fibers of HPMC excipient and ibuprofen drug with a drug weight fraction of (a) 0, (b) 0.1, and (c) 0.4; (d-f) HPMC-polyoxyl stearate-ibuprofen fibers with a drug weight fraction of (d) 0, (e) 0.1, and (f) 0.4.

FIG. 27a is a high-magnification image of the cross-section of a fiber that consists of only the HPMC excipient, i.e., without any drug. The structure was uniform at this scale. FIGS. 27b and 27c are high-magnification images of the cross-sections of single fibers comprising ibuprofen and HPMC with drug weight fractions, $w_d$=0.1 and $w_d$=0.4, respectively. Some drug particles could be seen and their size was 50-80 nm. The volume fraction of the particles was less than 0.01, much smaller than the weight fractions of drug in the fibers (0.1 and 0.4). This suggests that most of the drug was molecularly dissolved in the excipient.

FIG. 27d is a high-magnification image of the cross-section of a fiber of 67 wt % HPMC and 33 wt % polyoxyl stearate, without any drug. Small nano-particles of polyoxyl stearate embedded in the HPMC matrix could be seen at this scale. The nano-structures of the HPMC-polyoxyl stearate-ibuprofen fibers, shown in FIGS. 27e and 27f, were similar to the structure of the excipient. This suggests that in the HPMC-polyoxyl stearate-ibuprofen fibers, too, over 90% of the drug was present in molecular form.

Example 4: Differential Scanning Calorimetry (DSC)

A sample (a fiber or as-received ibuprofen particles) of about 3.5 milligrams was loaded in an aluminum pan and the specific heat flow to increase the temperature from 5 to 140° C., was measured with a TA Instruments Q200 DSC. The rate of temperature rise was 10° C. per minute in all the experiments.

Figure 28:
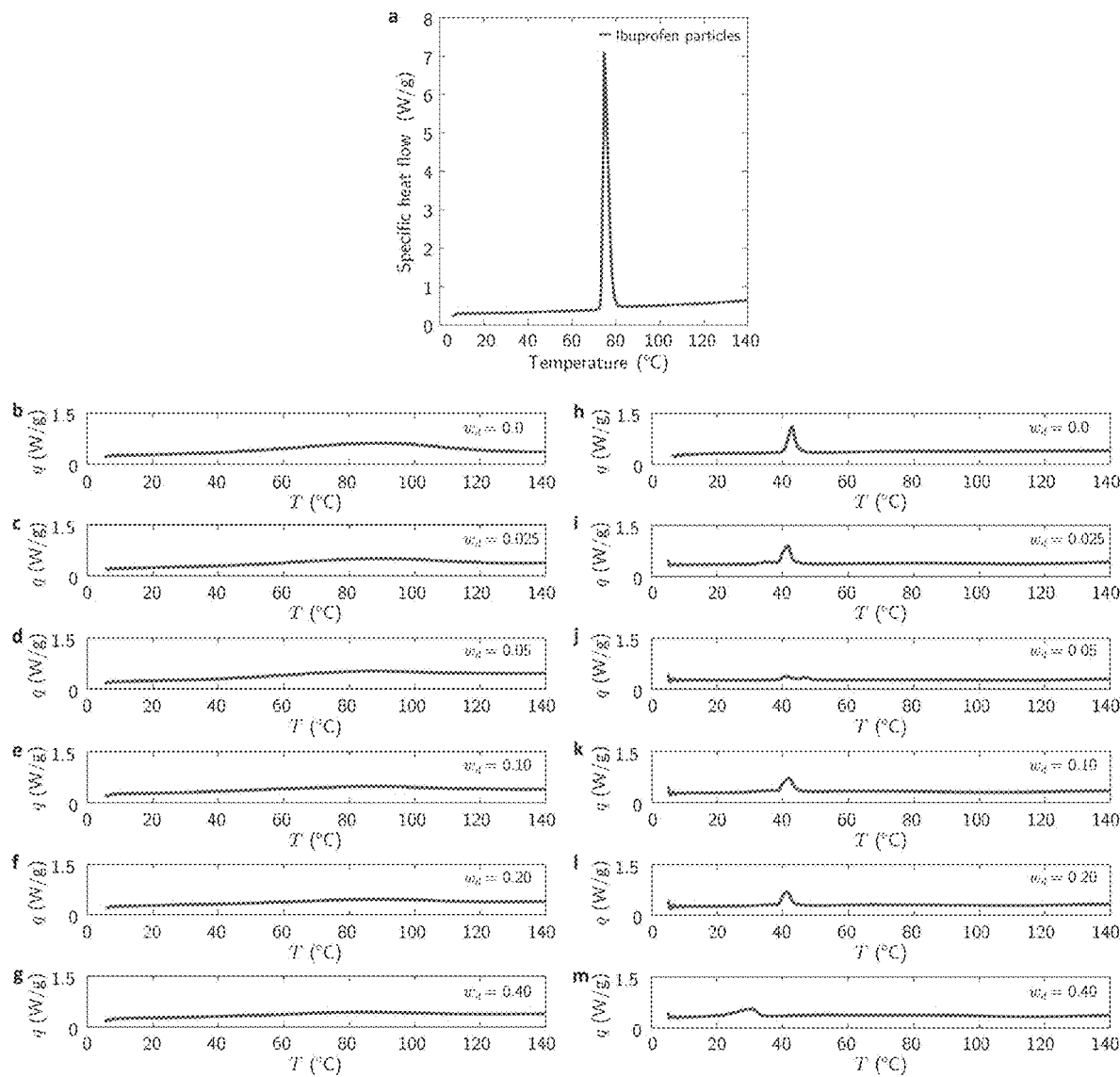
FIG. 28 presents the results of differential scanning calorigrams of the as-received drug particles and drug-laden fibers: (a) as-received ibuprofen particles, (b)-(g) fibers of HPMC and ibuprofen, and (h)-(m) HPMC-polyoxyl stearate-ibuprofen fibers. The drug weight fraction, $w_d$, in the fibers is shown in the figure windows.

FIG. 28a presents the specific heat flow into the drug particles at a rate of 10° C./min versus temperature. The specific heat flow was roughly constant below 71° C., and above 81° C., but exhibited a peak at 74.5° C., representing phase transformation from crystalline to a melt.

The differential scanning calorigrams of the HPMC and HPMC-ibuprofen fibers in the same temperature range but at a greater resolution of the heat flow are presented in FIGS. 28b-g. The heat flow was slightly increased compared with the baseline between 35 and 130° C., and exhibited a broad peak at roughly 85° C. Thus, no evidence of the presence of a crystalline drug phase was found in any of the fibers. This supports the results of the SEM images, suggesting that the drug was molecularly dispersed in the excipient.

The differential scanning calorigrams of the HPMC-polyoxyl stearate and HPMC-polyoxyl stearate-ibuprofen fibers are shown in FIGS. 28h-m. All graphs exhibited a small peak between 23 and 50° C., which was due to melting of polyoxyl stearate particles. No evidence of the presence of a crystalline drug phase was found in any of the fibers, however.

Example 5: Solubility of Drug in the Dissolution Fluid and Excipient-Fluid Solutions For determining the solubility of drug in the dissolution fluid, 1 mg ibuprofen particles were put in a UV cuvette. The cuvette was then filled with 2.5 ml of the dissolution fluid (0.1 M HCl in deionized water at 37° C.). The concentration of dissolved drug was monitored by UV absorption using a Perkin Elmer Lambda 1050 Spectrophotometer. Between measurements, the cuvette was flipped at a frequency of 0.5 Hz to stir the solution. The temperature of the solution in the cuvette was maintained at 37° C., during the experiment. When the drug concentration in the solution reached its equilibrium value the drug solubility was recorded.

The solubility of drug in excipient-dissolution fluid solutions was determined by immersing 1.5 mg of the ibuprofen particles and different amounts (1.5-200 mg) of excipient in 2.5 ml dissolution fluid. The excipient was either HPMC or a mixture of 67 wt % HPMC and 33 wt % polyoxyl stearate. The dissolution fluid was 0.1 M HCl in deionized water. The solution was allowed to equilibrate at 37° C. in the UV cuvette, and the equilibrium drug concentration, or solubility, was measured by UV absorption with the spectrophotometer above.

Figure 29:
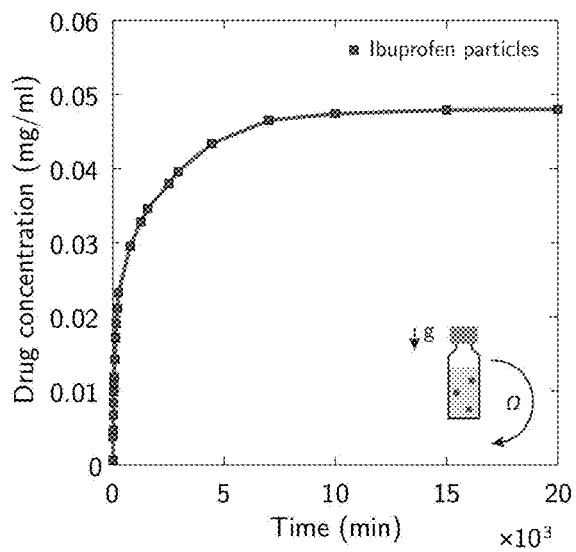
FIG. 29 is a plot of the ibuprofen concentration versus time after immersion of 1 mg ibuprofen particles (particle size: 500 µm) in 2.5 ml stirred dissolution fluid.

FIG. 29 is a plot of the concentration of dissolved drug versus time after immersion of 1 mg ibuprofen particles in 2.5 ml of stirred dissolution fluid. The drug concentration increased to 0.04 mg/ml in 3000 minutes (50 h), and then to the solubility $c_0$=0.05 mg/ml by 15,000 minutes (250 h).

Figure 30:
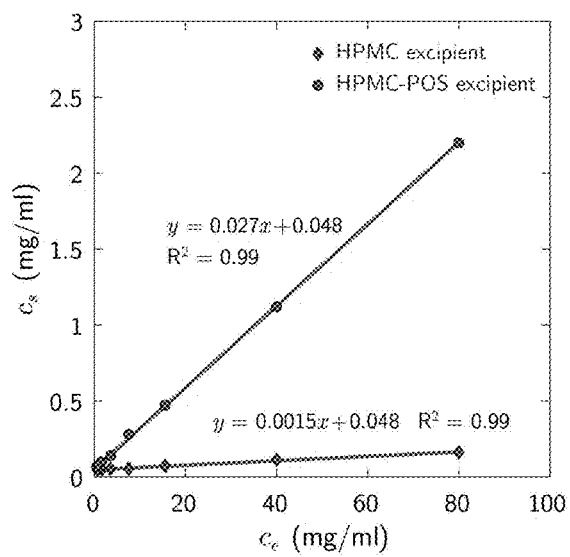
FIG. 30 presents the results of ibuprofen solubility versus concentration of excipient in the dissolution fluid. The excipient was either HPMC (bottom line) or 67 wt % HPMC and 33 wt % polyoxyl stearate (top line). The dissolution fluid was 0.1 M HCl in deionized water.

FIG. 30 presents the solubility, $c_s$, of ibuprofen in the dissolution fluid-excipient solutions versus the excipient concentration, $c_e$. The solubility depended linearly on the excipient concentration. For the HPMC excipient, $c_s$=0.0015$c_e$+0.05; for the HPMC-polyoxyl stearate excipient, $c_s$=0.027$c_e$+0.05. Thus the rate of solubility increase with excipient concentration was by a factor 20 greater for the HPMC-polyoxyl stearate excipient compared with HPMC alone.

Example 6: Imaging Fiber Disintegration in the Dissolution Fluid

For imaging fiber disintegration in the dissolution fluid the fiber was first attached to a sample holder using a drop of Loctite Super Glue. The fiber-loaded sample holder was then immersed in the dissolution fluid (0.1 M HCl in deionized water at 37° C.). The weight of drug in the fiber was less than 0.6 mg, and the volume of the dissolution fluid was 800 ml. Thus, the drug concentration in the fluid was less than 0.6/800=7.5×10$^{-4}$ mg/ml, much smaller than the drug solubility (0.05 mg/ml, as derived in example 5). The disintegrating fibers were imaged by a Nikon DX camera. Images of the disintegrating fibers were captured in both still (unstirred) and stirred (with a paddle rotating at 50 rpm) fluids.

Figure 31:
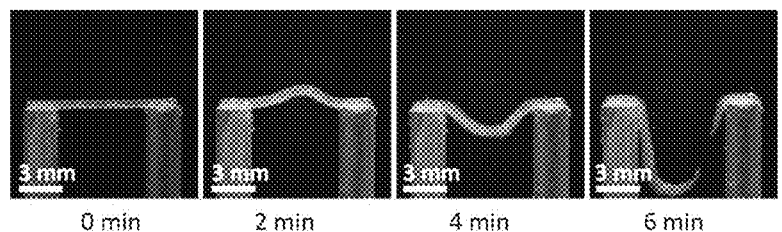
FIG. 31 displays the disintegration of an HPMC-ibuprofen fiber with drug weight fraction, $w_d$=0.05, in still dissolution fluid.

FIG. 31 is a series of images of a disintegrating HPMC-ibuprofen fiber with drug weight fraction, $w_d$=0.05, in still (unstirred) fluid. The fiber transitioned to viscous from the surface inwards. After about six minutes, it broke away from the support and fell down. The times to break the HPMC-polyoxyl stearate-ibuprofen fibers in still dissolution fluid were roughly the same, about 6 minutes.

Figure 32:
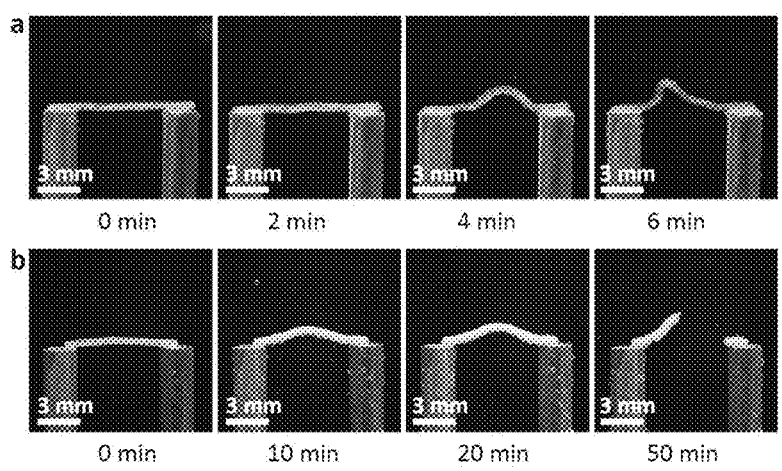
FIG. 32 shows the disintegration of HPMC-ibuprofen fibers in a stirred fluid: (a) $w_d$=0.05 and (b) $w_d$=0.4.

Representative images of HPMC-ibuprofen fibers after immersion in a stirred dissolution fluid are shown in FIG. 32. FIG. 32$a$ is a series of images of the disintegrating single fiber with drug weight fraction, $w_d$=0.05. Soon after immersion, the solid fiber transitioned to viscous (from the surface inwards). After about six minutes, the fiber broke away from its support and fell down. Afterwards it rapidly dissolved in the dissolution fluid.

The disintegration process of an HPMC-ibuprofen fiber with drug weight fraction 0.4 is presented in FIG. 32$b$. This fiber also transitioned to a viscous mass, from the surface inwards. The fiber broke away from its support about 50 minutes after immersion, a far longer time than that of the $w_d$=0.05 fiber. After breakage, the fiber continued to erode until it disappeared about 2-3 hours after immersion. Thus the disintegration time of the $w_d$=0.4 fiber was about 20-30 times longer time than that of the $w_d$=0.05 fiber.

Figure 33:
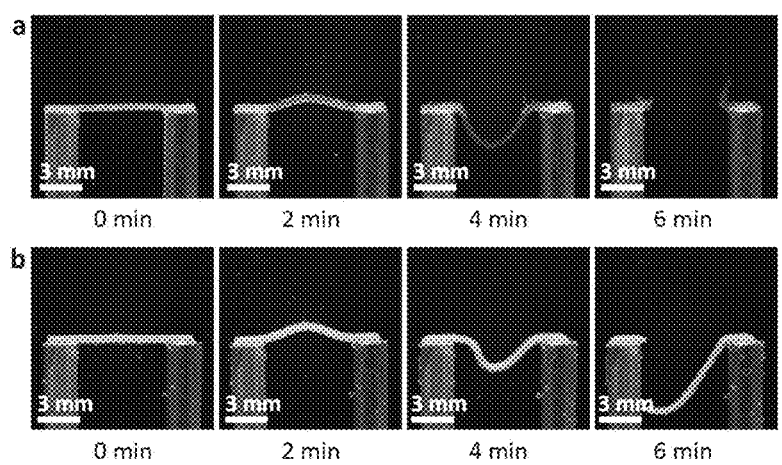
FIG. 33 presents the disintegration of HPMC-polyoxyl stearate-ibuprofen fibers in a stirred fluid: (a) $w_d$=0.05 and (b) $w_d$=0.4.

Images of disintegrating HPMC-polyoxyl stearate-ibuprofen fibers in stirred medium are shown in FIG. 33. FIG. 33$a$ presents a fiber with drug weight fraction, $w_d$=0.05, and FIG. 33$b$ a fiber with $w_d$=0.4. Both fibers transitioned from solid to viscous and broke away from their support about 5-6 minutes after immersion. In contrast to the HPMC-ibuprofen fibers, the disintegration rate of the HPMC-polyoxyl stearate-ibuprofen fibers did not depend strongly on the drug weight fraction.

Example 7: Drug Release into a Dissolution Fluid of Large Volume

For determining the drug release rate by the fibers into a stirred medium with drug concentration much smaller than the solubility, the experimental setup and conditions described above in example 6 were applied. The drug concentration in the dissolution fluid was measured versus time by UV absorption using a Perkin Elmer Lambda 1050 Spectrophotometer.

Figure 34:
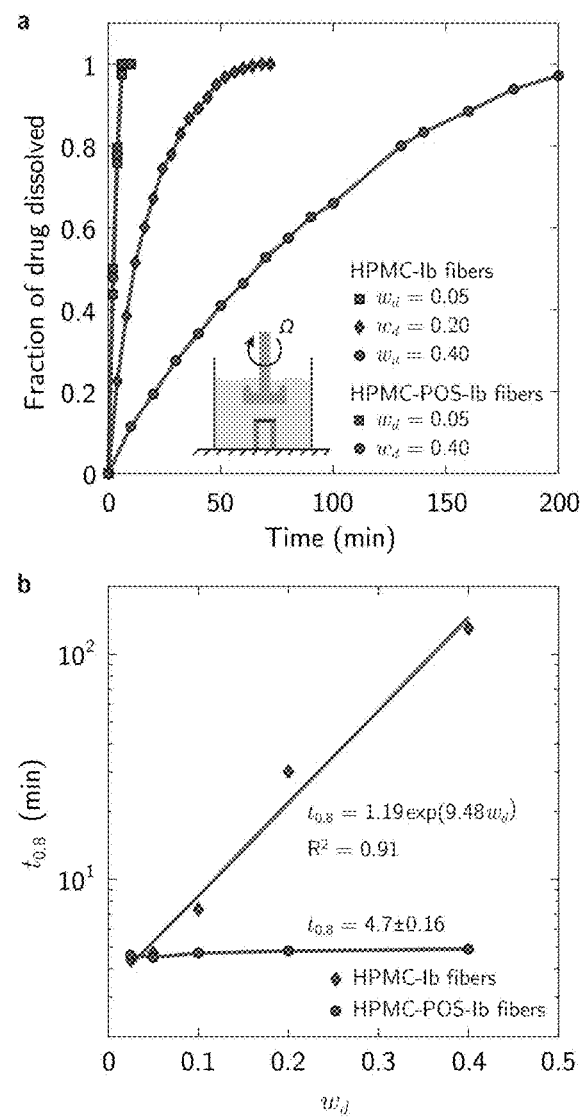
FIG. 34 presents results of drug release by solid-solution fibers containing 1 mg drug into a stirred fluid of large volume (500 ml): (a) fraction of drug dissolved versus time by select fibers, and (b) time to release 80% of the fiber's drug content, $t_{0.8}$, versus drug weight fraction, $w_d$. The ratio of the immersed drug mass and the volume of the dissolution fluid was less than $7.5 \times 10^{-4}$ mg/ml. This is much smaller than the drug solubility (0.05 mg/ml)

FIG. 34 presents the drug release behavior of the fibers in a dissolution fluid of large volume. FIG. 34$a$ shows that drug was released continuously until the fibers were dissolved, and FIG. 34$b$ plots the time to release 80% of the drug, $t_{0.8}$, versus $w_d$. $t_{0.8}$ of the HPMC-ibuprofen fibers increased exponentially with $w_d$. The corresponding values of the HPMC-polyoxyl stearate-ibuprofen fibers, however, were roughly constant.

The drug dissolution times were about the same as the disintegration times of the fibers from the non-limiting example 6.

Example 8: Drug Release and Precipitation in a Dissolution Fluid of Small Volume For immediate delivery into the blood stream, however, the concentration of a sparingly-soluble drug in the gastrointestinal fluid must be about or greater than the solubility. Thus, the drug release and precipitation rates in a saturating or supersaturating dissolution fluid were determined by first putting 1 mg of drug embedded in a fiber into a UV cuvette. The cuvette was then filled with 2.5 ml of the dissolution fluid (0.1 M HCl in deionized water at 37° C.). The concentration of dissolved drug was monitored by UV absorption using the spectrophotometer above. The cuvette was flipped between measurements at a frequency of 0.5 Hz to stir the solution. The temperature of the solution was maintained at 37° C., during the experiment.

Figure 35:
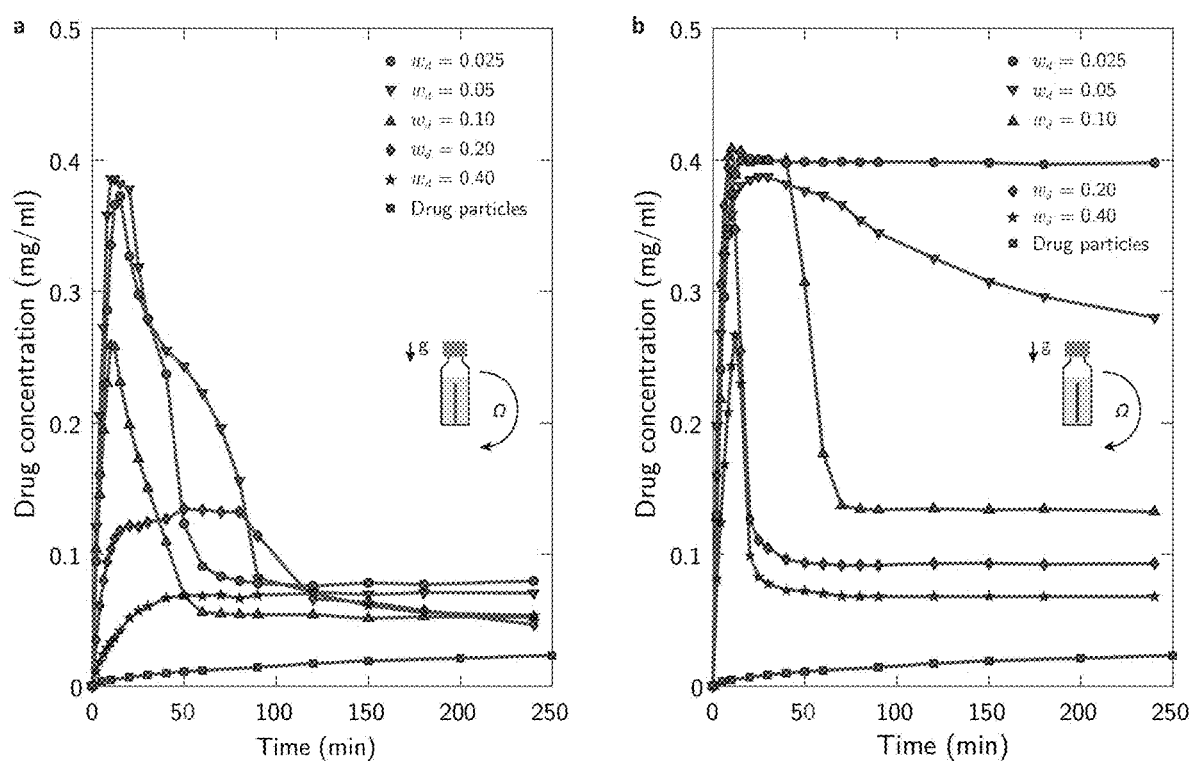
FIG. 35 shows results of drug concentration in the dissolution fluid versus time after immersion of fibers consisting of excipient and drug at various weight fractions: (a) HPMC-ibuprofen fibers, and (b) HPMC-polyoxyl stearate-ibuprofen fibers. The length of the fibers was so chosen that the initial drug content in all the fibers was 1 mg. The volume of the dissolution fluid was 2.5 ml. Thus, the ratio of the initial drug mass in the fibers and the volume of the dissolution fluid was 0.4 mg/ml.

FIG. 35$a$ presents the concentration of dissolved drug versus time after immersion of HPMC-ibuprofen fibers containing 1 mg of ibuprofen into 2.5 ml of dissolution fluid (0.4 mg/ml). The results are divided into two different groups depending on the drug weight fraction, $w_d$, in the fibers.

For $w_d \leq 0.1$, the drug concentration raised to a maximum, $c_{max}=0.26$-$0.39$ mg/ml almost immediately (within 10-15 minutes) after immersion. Thus, 65-98 percent of the drug was dissolved by that time. The solution was supersaturated, and the maximum supersaturation, $S_{max}=c_{max}/c_s=4.9$-$6.5$. Past the maximum the drug concentration decreased towards the solubility in the dissolution fluid (0.05-0.08 mg/ml). The 'final' concentrations were reached at about 60-90 minutes.

For $w_d > 0.1$, however, the drug concentration raised much slower, and the maximum drug concentration was decreased. For the fiber with $w_d = 0.4$, for example, $c_{max}=0.07$ mg/ml at $t_{cmax}=120$ minutes. Thus, only 18 percent of the immersed drug was ever dissolved. The drug concentration essentially plateaued towards the solubility (0.05 mg/ml).

FIG. 35b plots the concentration of dissolved drug versus time after immersing HPMC-polyoxyl stearate-ibuprofen fibers containing 1 mg of dispersed ibuprofen into 2.5 ml of gently stirred dissolution fluid. The solubility of drug in the dissolution fluid is increased substantially due to the presence of dissolved polyoxyl stearate. Thus, the data could be divided into the following two groups depending on the relative amounts of drug and excipient in the fibers.

For all other fibers the immersed excipient mass was less, and the immersed drug mass per unit volume of the solution was greater than the solubility. Even so, the drug concentration raised to a maximum of 0.27-0.4 mg/ml within 10-15 minutes. Thus, 68-100 percent of the drug was dissolved by that time. Past the maximum the drug concentration decreased and approached the solubility (0.07-0.28 mg/ml) after 30-70 minutes.

The drug release and concentration data for all fibers tested are summarized in Table 1.

Experiments on 3D-Micro-Patterned Dosage Forms

Example 9: Preparation of 3D-Micro-Patterned Dosage Forms

Ibuprofen drug particles were first dissolved in DMSO at a concentration of 123 mg drug/ml DMSO. The solution was then combined with the excipient (67 wt % hydroxypropyl methyl cellulose (HPMC) with a molecular weight of 10 kg/mol and 33 wt % polyoxyl stearate) at a concentration of 1.11 g excipient/ml DMSO. The mixture was extruded through a desktop extruder to form a uniform, viscous paste.

Figure 36:
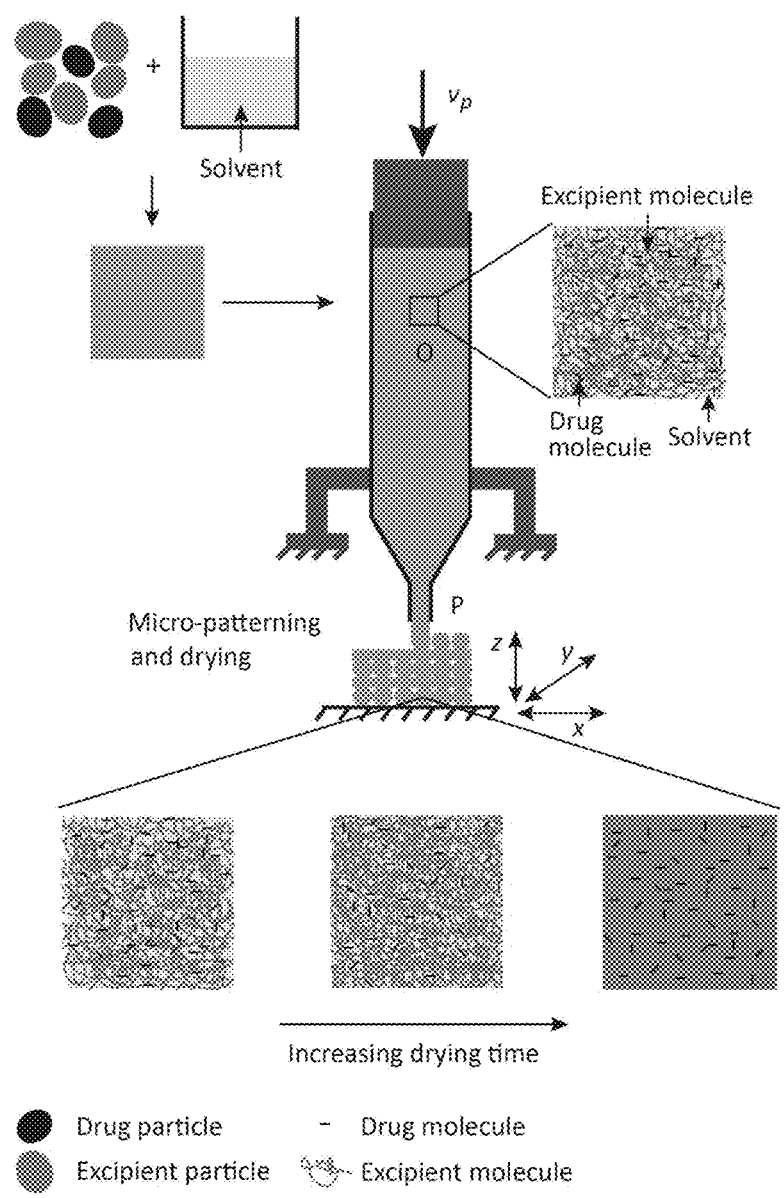
FIG. 36 is a schematic of the 3D-micro-patterning process for producing solid-solution fibrous dosage forms.

As shown schematically in FIG. 36, the as-prepared drug-excipient-solvent paste was then filled in a syringe at point O, and was extruded through a hypodermic needle at P. The extruded wet fiber was then patterned to a wet fibrous

TABLE 1

Drug release properties of drug particles and fibers.

| | $w_d$ | $l_f$ (mm) | $V_f$ (mm³) | $t_{cmax}$ (min) | $c_{max}$ (mg/ml) | $f_{max}$ | $S_{max}$ | $c_{240}$ (mg/ml) | $c_{s,\infty}$ (mg/ml) | $c_{e,\infty}$ (mg/ml) |
|---|---|---|---|---|---|---|---|---|---|---|
| | | | | Ibuprofen (drug) particles | | | | | | |
| A | — | — | — | — | 0.05 | 0.12 | 1.00 | 0.05 | 0.05 | 0.0 |
| | | | | HPMC-ibuprofen fibers | | | | | | |
| B | 0.025 | 346 | 34.8 | 15 | 0.38 | 0.93 | 5.26 | 0.08 | 0.07 | 15.6 |
| C | 0.05 | 173 | 17.4 | 12 | 0.39 | 0.97 | 6.53 | 0.07 | 0.06 | 7.6 |
| D | 0.1 | 86 | 8.7 | 10 | 0.26 | 0.65 | 4.86 | 0.05 | 0.05 | 3.6 |
| E | 0.2 | 43 | 4.3 | 50 | 0.13 | 0.34 | 2.66 | 0.05 | 0.05 | 1.6 |
| F | 0.4 | 22 | 2.2 | 120 | 0.07 | 0.18 | 1.43 | 0.05 | 0.05 | 0.6 |
| | | | | HPMC-polyoxyl stearate-ibuprofen fibers | | | | | | |
| G | 0.025 | 346 | 34.8 | 15 | 0.40 | 1.00 | 1.00 | 0.40 | 0.47 | 15.6 |
| H | 0.05 | 173 | 17.4 | 20 | 0.39 | 0.97 | 1.54 | 0.28 | 0.25 | 7.6 |
| I | 0.1 | 86 | 8.7 | 15 | 0.41 | 1.01 | 2.79 | 0.14 | 0.15 | 3.6 |
| J | 0.2 | 43 | 4.3 | 8 | 0.39 | 0.99 | 4.33 | 0.09 | 0.09 | 1.6 |
| K | 0.4 | 22 | 2.2 | 12 | 0.27 | 0.67 | 4.16 | 0.07 | 0.06 | 0.6 |

$w_d$: drug weight fraction in dry fiber;
$l_f$: fiber length;
$V_f$: fiber volume;
$t_{cmax}$: time to reach maximum drug concentration;
$c_{max}$: maximum drug concentration in supersaturated fluid;
$f_{max}$: fraction of drug dissolved at maximum concentration;
$S_{max}$: maximum supersaturation;
$c_{240}$: drug concentration at 240 minutes;
$c_{s,\infty}$: drug solubility after fiber dissolution;
$c_{e,\infty}$: excipient concentration after fiber dissolution.
The data are extracted from the results plotted in FIGS. 29, 30, and 35.
The drug mass in each fiber was 1 mg.
The fiber volume is estimated as follows: $V_f = 1$ mg/$w_d\rho_f$ where the fiber density, $\rho_f \approx 1150$ kg/m³.
The volume of the dissolution fluid was 2.5 ml (2,500 mm³).

For $w_d=0.025$, the mass of excipient that dissolved in the dissolution medium upon immersion of the fiber was so large (39 mg) that the drug concentration was less than the solubility at any time. The drug concentration plateaued out to 0.4 mg/ml, accordingly.

dosage form with cross-ply structure. Three dosage form structures (A, B, and C) were patterned, as listed in Table 2. After patterning, warm air at a temperature of about 50° C., and a velocity of 2.3 m/s was blown on the dosage form to evaporate the solvent and solidify the structure.

The dry structures were trimmed (also referred to herein as "cut") to a square disk-shaped dosage form of nominal volume 8 mm×8 mm×3.6 mm. The dry dosage forms consisted of 10 wt % ibuprofen, 60 wt % HPMC, and 30 wt % POS.

Moreover, the fibers in the dosage form were coated with a thin hydrophilic coating. The coating was applied by dripping a few droplets of the coating solution (Polyvinyl pyrrolidone (PVP) with a molecular weight of 10 kg/mol, mannitol, and ethanol; concentration of PVP: 10 mg/ml ethanol; concentration of mannitol: 20 mg/ml ethanol) on the dosage form and drying immediately after by blowing warm air at 50° C., and 2.3 m/s.

Single fibers of the same composition were prepared as detailed above. The drug weights in the dry fibers with designations D, E, and F were the same as those in dosage forms A, B, and C, respectively, Table 2.

TABLE 2

Nominal microstructural parameters of the wet fibers and wet dosage forms, and the composition of dry fibers and fibrous dosage forms by weight.

| | $R_n$ (μm) | $\lambda_n$ (μm) | $R_n/\lambda_n$ | $M_{df}$ (mg) | $M_d$ (mg) | $M_e$ (mg) |
|---|---|---|---|---|---|---|
| Fibrous dosage forms | | | | | | |
| A | 130 | 900 | 0.14 | 80 | 8.0 | 72.0 |
| B | 130 | 500 | 0.26 | 144 | 14.4 | 129.6 |
| C | 130 | 385 | 0.34 | 188 | 18.8 | 169.2 |
| Fibers | | | | | | |
| D | 130 | — | — | 80 | 8.0 | 72.0 |
| E | 130 | — | — | 144 | 14.4 | 129.6 |
| F | 130 | — | — | 188 | 18.8 | 169.2 |

$R_n$: nominal radius of wet fiber;
$\lambda_n$: nominal inter-fiber distance in wet structure;
$M_{df}$: mass of dry dosage form;
$M_d$: drug mass in dosage form;
$M_e$: excipient mass in dosage form.
The microstructural parameters of dry dosage forms differ from the nominal parameters because the dosage form shrinks during drying (Table 3, later).

Example 10: Microstructures by Scanning Electron Microsopy

The fibrous dosage forms and a single fiber were imaged by a Zeiss Merlin High Resolution SEM with a GEMINI column. Top views were imaged without any preparation of the sample. For imaging cross-sections, however, the samples were cut with a thin blade (MX35 Ultra, Thermo Scientific, Waltham, MA). Imaging was done with an in-lens secondary electron detector. The accelerating voltage was 5 kV and the probe current was 95 pA.

Figure 37:
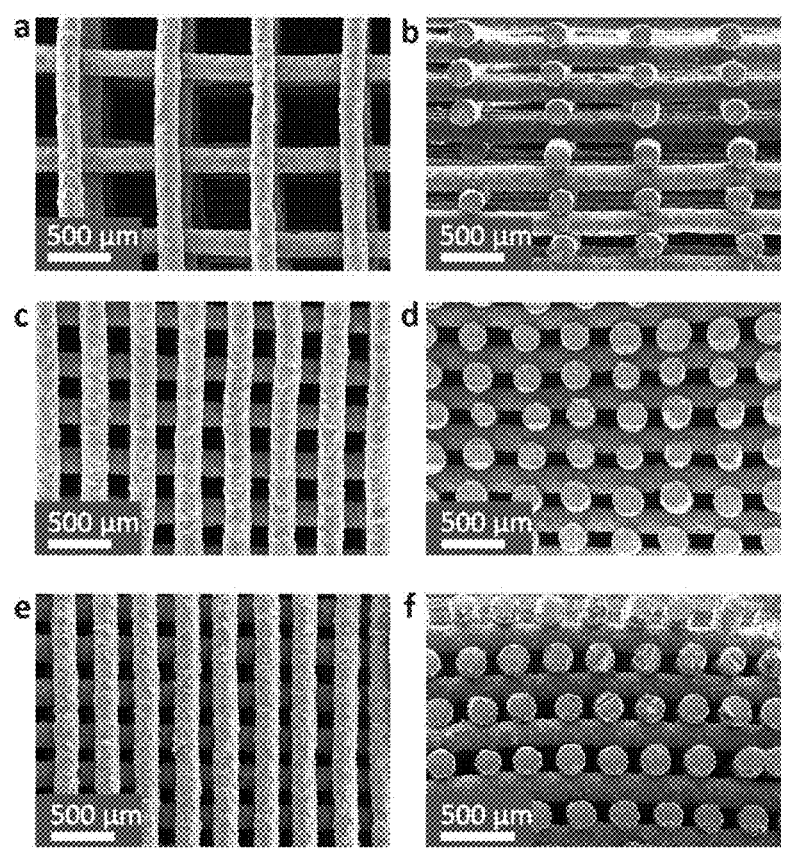
FIG. 37 displays scanning electron micrographs of the microstructure of fibrous dosage forms: (a) top view, and (b) front view of the cross-section of dosage form A; (c) top view, and (d) cross-section of dosage form B: (e) top view, and (f) cross-section of dosage form C. The microstructural parameters of the dosage forms are listed in Table 3.

Scanning electron micrographs of the fibrous dosage forms are shown in FIG. 37. FIG. 37a is the top view and FIG. 37b the front view of dosage form A. The measured radius, $R_0$=98 μm, and the inter-fiber distance, $\lambda_0$=712 μm. This is 75-79 percent of the nominal values, $R_n$=130 μm and $\lambda_n$=900 μm. Thus, the dosage forms shrinked isotropically during solvent evaporation. FIGS. 37c-37f show the microstructures of the other dosage forms. As summarized in Table 3, the ratios $R_0/R_n$ and $\lambda_0/\lambda_n$ were about the same as in the first case.

TABLE 3

Microstructural parameters of fibrous dosage forms.

| | $R_0$ (μm) | $R_0/R_n$ | $\lambda_0$ (μm) | $\lambda_0/\lambda_n$ | $R_0/\lambda_0$ | $\varphi_s$ |
|---|---|---|---|---|---|---|
| A | 98 ± 3 | 0.75 | 712 ± 45 | 0.79 | 0.14 | 0.27 |
| B | 104 ± 4 | 0.80 | 385 ± 15 | 0.77 | 0.27 | 0.53 |
| C | 97 ± 2 | 0.75 | 297 ± 20 | 0.77 | 0.33 | 0.65 |

The nominal values, $R_n$ = 130 μm, and $\lambda_n$ = 900, 500, and 385 μm, respectively, for dosage forms A, B, and C.
The data are obtained from the SEM images in FIG. 37.
The true volume fraction of solid in dry dosage forms, $\varphi_s = \xi \pi R_0/2\lambda_0$, where $\xi \approx 1.25$.

Example 11: Images of Disintegrating Dosage Forms

A dosage form was immersed in a beaker filled with 500 ml of the dissolution fluid (0.1 M HCl in deionized water at 37° C.). The fluid was stirred with a paddle rotating at 50 rpm. The disintegrating sample was continuously imaged by a Nikon DX camera.

Figure 38:
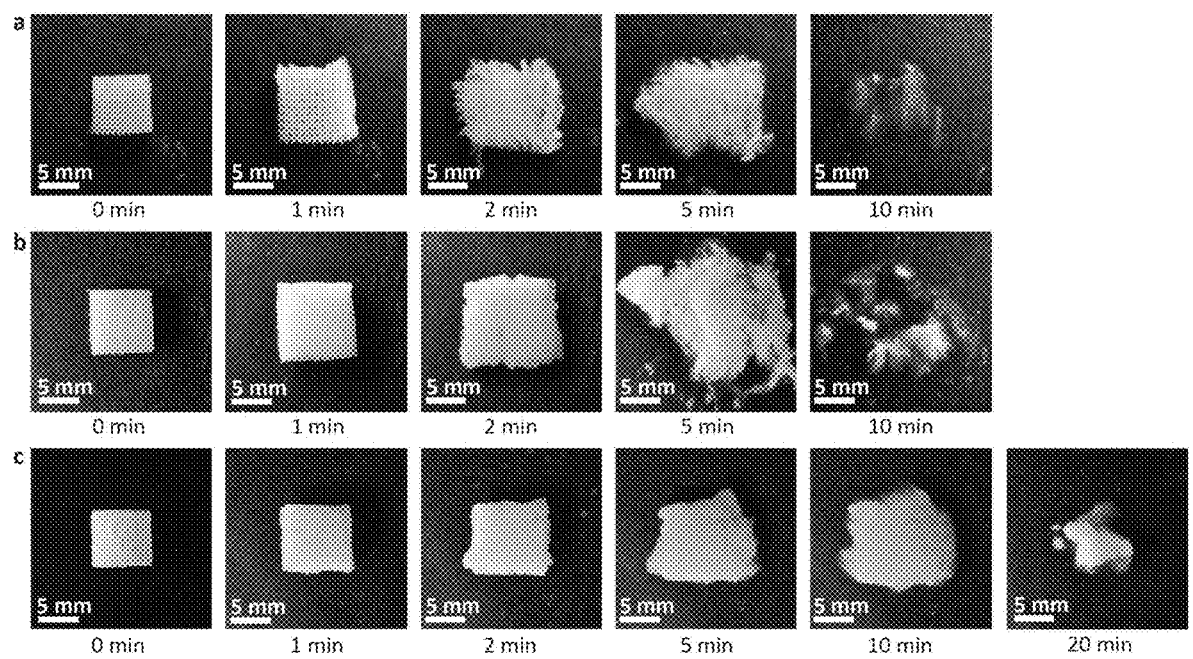
FIG. 38 shows the disintegration of fibrous dosage forms after immersion in a stirred dissolution fluid: (a) $\varphi_s$=0.27, (b) $\varphi_s$=0.53, and (c) $\varphi_s$=0.65. The microstructural parameters are listed in Table 1, and the properties in Tables 3 and 4. The volume of the dissolution fluid was 500 ml.

Images of the disintegrating fibrous dosage forms are shown in FIG. 38. In all cases, upon immersion the dissolution fluid percolated the void space almost immediately. The solid dosage forms then transitioned to viscous and expanded uniformly in all directions. As summarized in Table 4, the normalized longitudinal expansion after two minutes, $\Delta L_2/L_0$ was 0.51 ($\varphi_s$=0.27, A), 0.43 ($\varphi_s$=0.53, A), and 0.29 ($\varphi_s$=0.65, C).

After about 2-3 minutes of immersion and expansion, all three dosage forms started to deform viscously due to gravity and fluid shear. The structures collapsed and a viscous drug-excipient-dissolution fluid medium was formed along the flat surface. The viscous medium eroded into the dissolution fluid and was dissolved after about 6-10 (A), 10-15 (B), and 20-30 minutes (C).

Example 12: Drug Release into a Dissolution Fluid of Large Volume

The amount of drug released versus time in a dissolution fluid of large volume (a sink) was determined with the same experimental setup and under the same conditions as in section 2.5. The drug concentration was measured by UV absorption using a Perkin Elmer Lambda 1050 Spectrophotometer. The concentration of dissolved drug was determined by subtracting the UV absorbance at the wavelength 248 nm from the absorbance at 242 nm. The terminal drug concentration in the dissolution fluid was smaller than the solubility in all cases.

Figure 39:
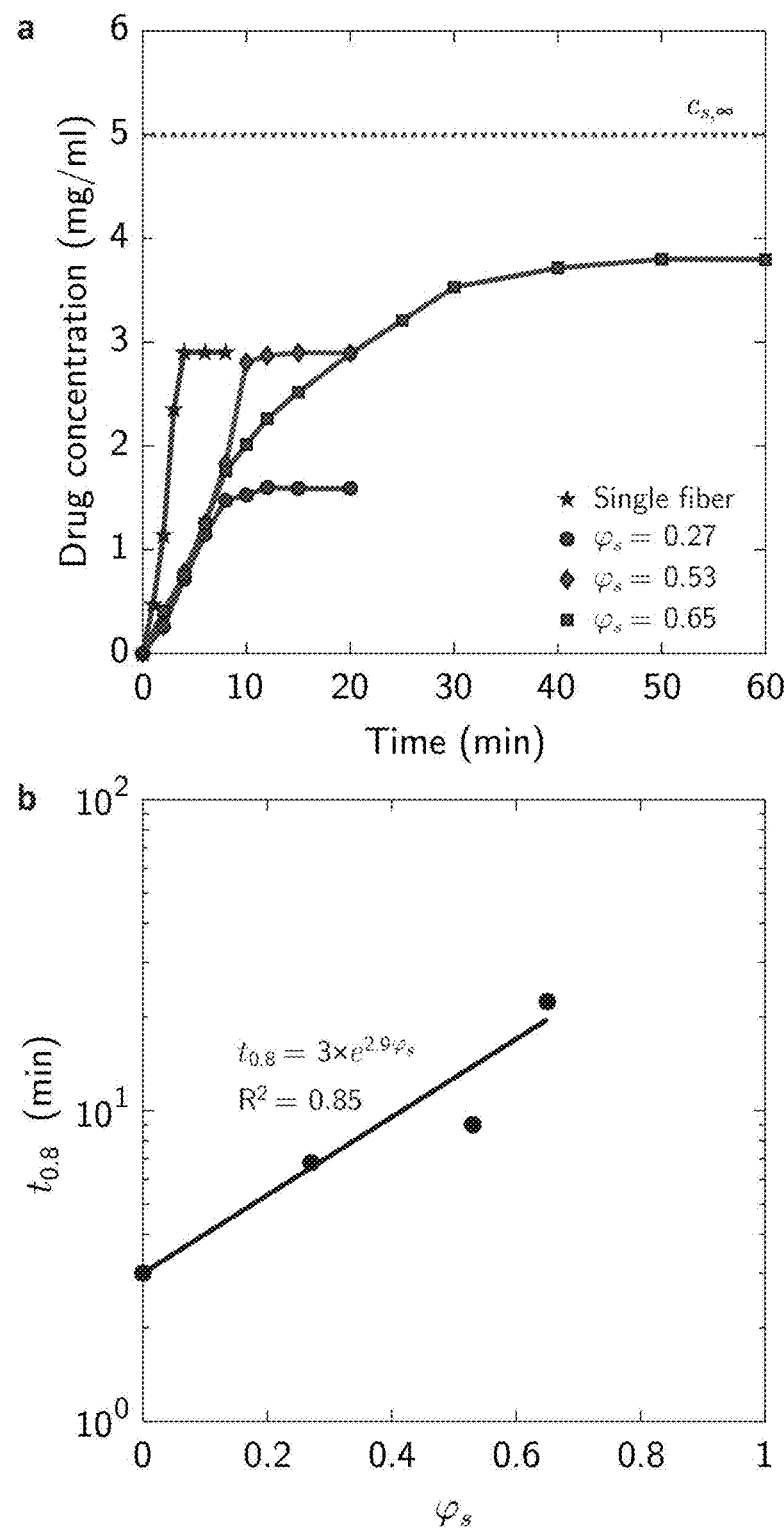
FIG. 39 presents the drug release results in a stirred dissolution fluid of large volume (500 ml): (a) Drug concentration versus time, and (b) time to dissolve 80 percent of the drug content, $t_{0.8}$, versus volume fraction of solid fibers, $\varphi_s$. The fibrous dosage forms were square disks of side length 8 mm and thickness 3.6 mm. In all cases, the drug concentration in the dissolution medium was smaller than the solubility, $c_{s,\infty} \approx 0.05$ mg/ml.

The drug concentration versus time in the large-volume (500 ml) dissolution fluid, where the drug concentration remained below the solubility, is shown in FIG. 39a. A semi-log plot of the time to dissolve 80% of the drug content, $t_{0.8}$, versus fiber volume fraction, $\varphi_s$, is presented in FIG. 39b. The $t_{0.8}$ time increased with fiber volume fraction, from 6.8 minutes for $\varphi_s$=0.27 (A) to 9 minutes ($\varphi_s$=0.53; B), and 22 minutes ($\varphi_s$=0.65; C), Table 4. The $t_{0.8}$ time of the single fiber was 3 minutes.

TABLE 4

Disintegration and drug release properties of fibrous dosage forms and single fiber after immersion in 500 ml dissolution fluid.

| | $R_0$ (μm) | $\lambda_0$ (μm) | $R_0/\lambda_0$ | $\varphi_s$ | $\Delta R_2/R_0$ | $\Delta L_2/L_0$ | $t_{0.8}$ (min) |
|---|---|---|---|---|---|---|---|
| | | | Fibrous dosage forms | | | | |
| A | 98 ± 3 | 712 ± 45 | 0.14 | 0.27 | — | 0.51 | 6.8 |
| B | 104 ± 4 | 385 ± 15 | 0.27 | 0.53 | — | 0.43 | 9.0 |
| C | 98 ± 2 | 297 ± 20 | 0.33 | 0.65 | — | 0.29 | 22.4 |
| | | | Single fiber | | | | |
| E | 102 ± 3 | — | — | — | 0.52 | 0.34 | 3.0 |

$\Delta R_2/R_0$ and $\Delta L_2/L_0$ are the normalized radial and longitudinal expansions two minutes after immersion.
$t_{0.8}$ is the time to release 80% of the drug content.
The data are from FIGS. 37, 38, 39, and 41.

Example 13: Drug Release into a Dissolution Fluid of Small Volume

In the gastrointestinal fluid, however, the mass of the sparingly-soluble drug per unit volume of the fluid is greater than the solubility. Thus, to imitate the gastrointestinal conditions, experiments were also conducted in a dissolution fluid of small volume (a non-sink). The fluid volume was 20 ml, and all other experimental conditions were the same as above (sections 2.5 and 2.6).

Figure 40:
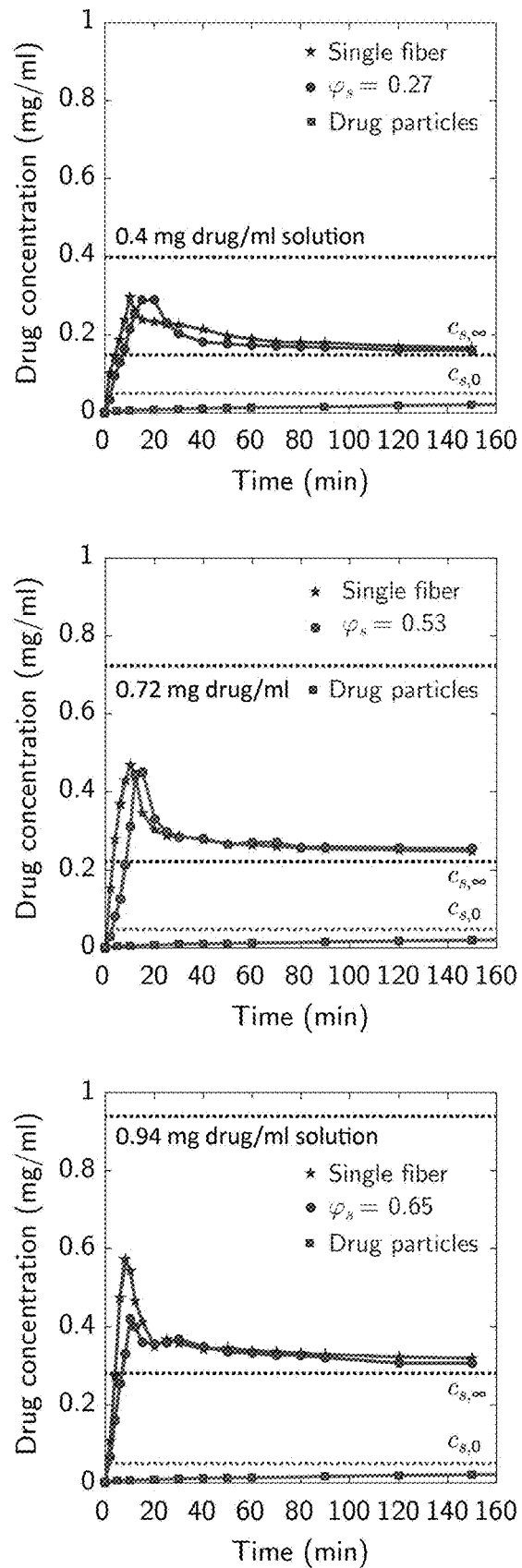
FIG. 40 shows drug concentration versus time after immersion of fibrous dosage forms (A, B, and C) and single fibers (D, E, and F) in a stirred dissolution fluid of volume 20 ml. The mass of drug in A, B, and C was 8, 14.4, and 18.7 mg, respectively. The dosage forms were square disks with side length 8 mm and thickness 3.6 mm.

FIG. 40 presents the drug concentration versus time after immersion of the fibrous dosage forms and the corresponding single fibers in a small-volume dissolution fluid (20 ml). The immersed drug masses per unit volume of the fluid were 0.4 (A), 0.72 (B), and 0.94 mg/ml (C), far greater than the solubilities in the terminal solutions, $c_{s,\infty}$, Table 5.

As shown in FIG. 40a, the drug concentration-time curve of dosage form A ($\varphi_s=0.27$) was about the same as that of single fiber D. The drug concentration increased to a maximum of 0.29 mg/ml within 10-15 minutes (Table 5). Thus, roughly 73 percent of the drug was dissolved by that time. The solution was supersaturated and the maximum supersaturation, $S_{max}$, was about 2. Past the maximum, the drug concentration decreased and approached the terminal solubility, $c_{s,\infty}=0.14$ mg/ml.

FIG. 40b presents the concentration-time curves of dosage form B ($\varphi_s=0.53$) and single fiber E. Again, the two curves were about the same. As in the previous case $S_{max}$ was about 2 after 10-15 minutes (Table 5). The terminal solubility was 0.23 mg/ml, in proportion to the immersed mass of drug and excipient greater than in the first case.

FIG. 40c shows the concentration-time curves of dosage form C ($\varphi_s=0.65$) and fiber F. Unlike in the previous cases, $S_{max}$ of the dosage form was reduced to 1.5 and was 36 percent less than that of the single fiber. The terminal solubility was 0.27 mg/ml (6 times $c_{s,0}$) for both the dosage form and the single fiber. Thus, even though the supersaturation was slightly less, dosage form C maximized the drug concentration in the dissolution fluid.

TABLE 5

Microstructural parameters and drug release properties of single fibers and fibrous dosage forms

| | Microstructural parameters | | | | Drug release properties | | | | | | |
|---|---|---|---|---|---|---|---|---|---|---|---|
| | $R_0$ (μm) | $\lambda_0$ (μm) | $R_0/\lambda_0$ | $\varphi_s$ | $M_d$ (mg) | $t_{cmax}$ (min) | $c_{max}$ (mg/ml) | $f_{max}$ | $S_{max}$ | $c_{e,\infty}$ (mg/ml) | $c_{s,\infty}$ (mg/ml) |
| | | | | | Fibrous dosage forms | | | | | | |
| A | 98 ± 3 | 712 ± 45 | 0.14 | 0.27 | 8.0 | 15 | 0.290 | 0.73 | 2.00 | 3.6 | 0.14 |
| B | 104 ± 4 | 385 ± 15 | 0.27 | 0.53 | 14.4 | 15 | 0.450 | 0.63 | 2.01 | 6.5 | 0.23 |
| C | 98 ± 2 | 297 ± 20 | 0.33 | 0.65 | 18.8 | 10 | 0.420 | 0.45 | 1.53 | 8.4 | 0.27 |
| | | | | | Single fibers | | | | | | |
| D | 102 ± 3 | — | — | — | 8.0 | 10 | 0.297 | 0.74 | 2.05 | 3.6 | 0.14 |
| E | 102 ± 3 | — | — | — | 14.4 | 10 | 0.469 | 0.65 | 2.10 | 6.5 | 0.23 |
| F | 102 ± 3 | — | — | — | 18.8 | 8 | 0.573 | 0.61 | 2.09 | 8.4 | 0.27 |

$R_0$: fiber radius;

$\lambda_0$: inter-fiber distance;

$\varphi_s$: volume fraction of fibers in solid dosage form;

$M_d$: drug mass in dosage form;

$t_{cmax}$: time to reach maximum drug concentration;

$c_{max}$: maximum drug concentration;

$f_{max}$: mass fraction of drug dissolved at maximum concentration;

$S_{max}$: maximum supersaturation;

$c_{e,\infty}$: excipient concentration after dissolution of sample;

$c_{s,\infty}$: drug solubility after dissolution of sample.

Geometry of fibrous dosage forms: square disks with side length 8 mm and thickness 3.6 mm. Nominal volume: 230 mm$^3$.

The maximum supersaturation $S_{max} = c_{max}/c_{s,\infty}$ where $c_{s,\infty} = 0.027 c_{e,\infty} \pm c_{s,0}$.

The solubility of ibuprofen in 0.1M HCl, $c_{s,0} = 0.05$ mg/ml.

The data are from FIGS. 30, 37, and 40.

Supporting Experiments

Example 14: Expansion of HPMC-POS-Ibuprofen Single Fiber

Figure 41:
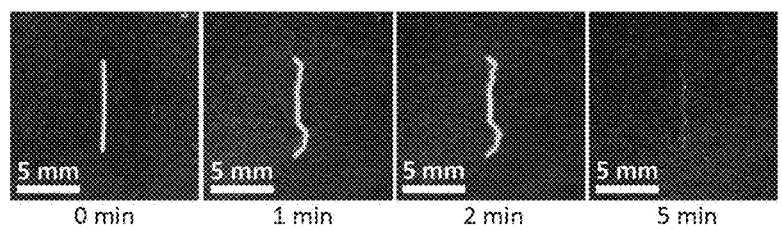
FIG. 41 presents images of HPMC-POS-ibuprofen fiber disintegration. The initial fiber length was about 7.5 mm.

HPMC-POS-ibuprofen fibers were prepared as described in example 9. FIG. 41 presents images of a disintegrating HPMC-POS-ibuprofen fiber in a stirred dissolution fluid. Upon immersion in DI water with 0.1 M HCl at 37° C., the fiber transitioned from solid to viscous and expanded both radially and longitudinally. As summarized in Table 4, at two minutes $\Delta R_2/R_0=0.52$ and $\Delta L_2/L_0=0.34$. During and after expansion the fiber eroded into the dissolution fluid. It was essentially dissolved five minutes after immersion.

Example 15: Expansion of HPMC-Ibuprofen Fiber

HPMC-ibuprofen fibers were also prepared as described in example 9, but without adding polyoxyl stearate to the formulation. The dry fiber consisted of 90 wt % HPMC and 10 wt % ibuprofen.

Figure 42:
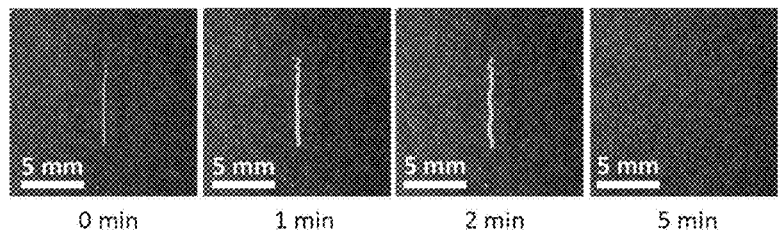
FIG. 42 shows images of HPMC-ibuprofen fiber disintegration. The initial length was about 7.5 mm.

As shown in FIG. 42, upon immersion in DI water with 0.1 M HCl at 37° C., the HPMC-ibuprofen fiber transitioned from solid to viscous and expanded. After two minutes, $\Delta R_2/R_0=0.64$ and $\Delta L_2/L_0=0.1$. Thus, unlike in the case of the HPMC-POS-ibuprofen fiber, the radial expansion was far greater than the longitudinal expansion. Therefore, the polyoxyl stearate micelles facilitated isotropic expansion of the fiber.

Example 16: Rheometry

The shear viscosity of water-penetrated HPMC excipient was determined with a shear rheometer (TA Instruments, ARG2 Rheometer, stress-controlled) equipped with a 60 mm diameter cone with an apex angle of 178°. The solutions analyzed consisted of water and HPMC (molecular weight=10 kg/mol) at a polymer concentration of 1, 2, 5, 10, and 20 wt %. The temperature during the experiments was 37° C., and the shear strain-rate range was 1-100/s.

Figure 43:
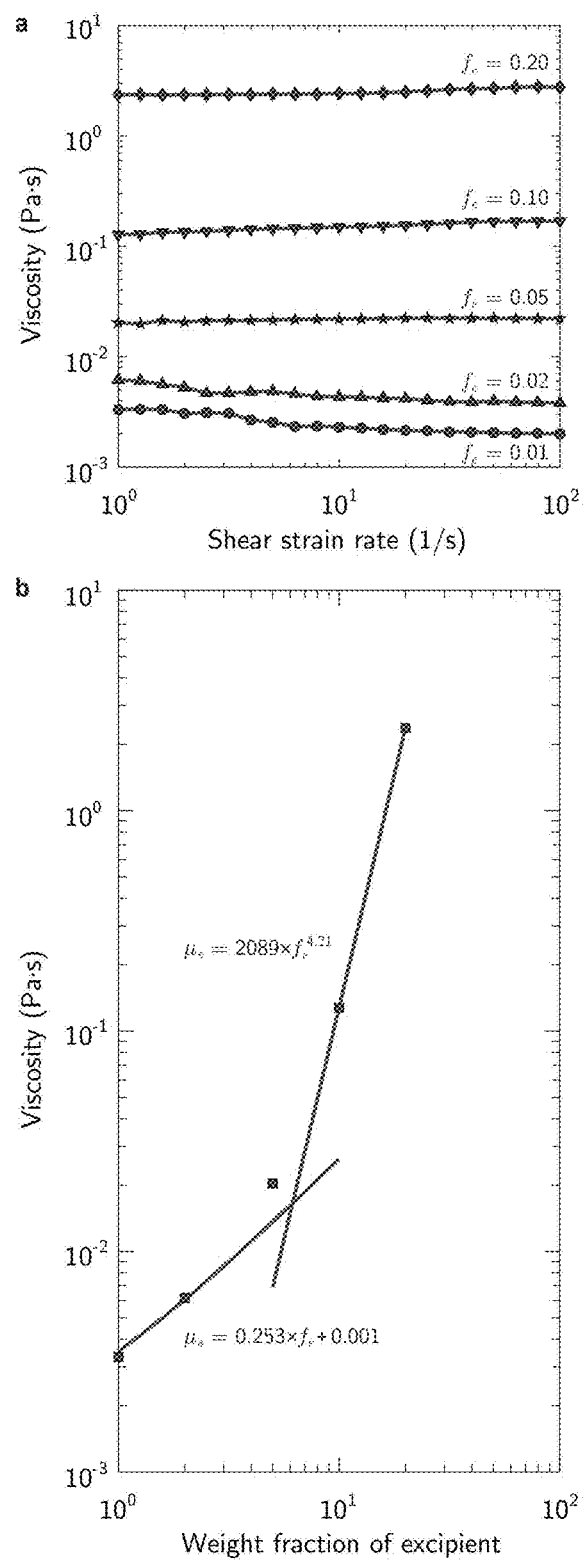
FIG. 43 presents the results of shear viscosity, $\mu_s$, of HPMC-water solutions at various weight fractions of the excipient, $f_e$: (a) viscosity versus shear rate, and (b) $\mu_s$ versus $f_e$ at a shear rate of 1/s.

FIG. 43 presents the shear viscosity, $\mu_s$, of HPMC-water solutions at various weight fractions of the excipient, $f_e$. FIG. 43a is the viscosity versus shear rate in the range 1-100/s and FIG. 43b shows $\mu_s$ versus $f_e$ at a shear rate of 1/s. In the dilute region, the viscosity followed an equation of the form of the Einstein viscosity relation, $\mu_s=0.253f_e+0.001$ Pa·s. In the semi-dilute region, $\mu_s=2089f_e4.21$. The dilute and semi-dilute regions were separated by the disentanglement weight fraction, $f_e^*=0.062$. Thus, the disentanglement concentration of the excipient, $c_e^*\approx70$ mg/ml.

Example 17: Preparation and Structure of Films Comprising Dispersed Drug Nano-Particles in an Excipient Films of dispersed drug nano-particles in an excipient were prepared as follows. HPMC-water paste was mixed with solution of dissolved ibuprofen in ethanol. The mixture was spread on a substrate and dried.

Figure 44:
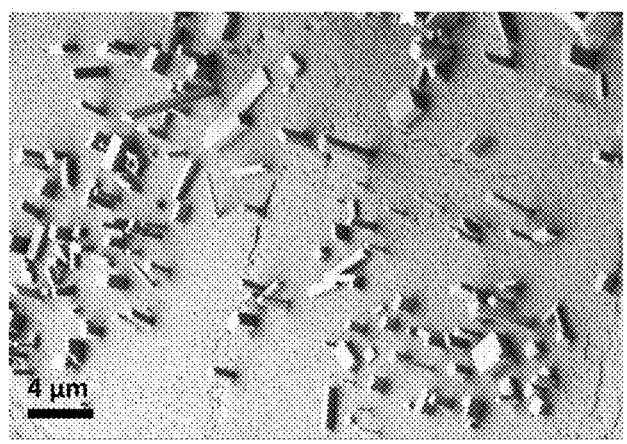
FIG. 44 presents a scanning electron micrograph of the microstructure of dispersed nano-particles of ibuprofen drug in a matrix of hydroxypropyl methylcellulose (HPMC) excipient.

FIG. 44 presents a scanning electron micrograph of the microstructure of the film. Ibuprofen nano-particles (e.g., nanometer-scale agglomerates or crystals of ibuprofen as defined herein) are embedded in a matrix of HPMC.

Application Examples

In some embodiments, the amount of active ingredient contained in a dosage form disclosed in this invention is appropriate for administration in a therapeutic regimen that shows a statistically significant probability of achieving a predetermined therapeutic effect when administered to a relevant population. By way of example but not by way of limitation, active ingredients may be selected from the group consisting of acetaminophen, aspirin, caffeine, ibuprofen, an analgesic, an anti-inflammatory agent, an anthelmintic, anti-arrhythmic, antibiotic, anticoagulant, antidepressant, antidiabetic, antiepileptic, antihistamine, antihypertensive, antimuscarinic, antimycobacterial, antineoplastic, immunosuppressant, antithyroid, antiviral, anxiolytic and sedatives, beta-adrenoceptor blocking agents, cardiac inotropic agent, corticosteroid, cough suppressant, diuretic, dopaminergic, immunological agent, lipid regulating agent, muscle relaxant, parasympathomimetic, parathyroid, calcitonin and biphosphonates, prostaglandin, radiopharmaceutical, anti-allergic agent, sympathomimetic, thyroid agent, PDE IV inhibitor, CSBP/RK/p38 inhibitor, or a vasodilator).

In conclusion, this invention discloses a dosage form with predictable structure and drug release behaviour. Both can be tailored by well-controllable parameters. This enables improved control of the drug release and drug delivery rates into the blood stream, and thus improved control of drug concentration in blood. This further enables faster and more economical development and manufacture of pharmaceutical dosage forms, and higher quality and more personalized medical treatments.

It is contemplated that a particular feature described either individually or as part of an embodiment in this disclosure can be combined with other individually described features, or parts of other embodiments, even if the other features and embodiments make no mention of the particular feature. Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

By way of example but not by way of limitation, it is contemplated that compositions, systems, devices, methods, and processes of the claimed invention encompass variations and adaptations developed using information from the embodiments described herein. Adaptation and/or modification of the compositions, systems, devices, methods, and processes described herein may be performed by those of ordinary skill in the relevant art.

Furthermore, where compositions, articles, and devices are described as having, including, or comprising specific components, or where processes and methods are described as having, including, or comprising specific steps, it is contemplated that, additionally, there are compositions, articles, and devices of the present invention that consist essentially of, or consist of, the recited components, and that there are processes and methods according to the present invention that consist essentially of, or consist of, the recited processing steps.

Similarly, where compositions, articles, and devices are described as having, including, or comprising specific compounds and/or materials, it is contemplated that, additionally, there are compositions, articles, and devices of the present invention that consist essentially of, or consist of, the recited compounds and/or materials.

It should be understood that the order of steps or order for performing certain action is immaterial so long as the invention remains operable. Moreover, two or more steps or actions may be conducted simultaneously.

The mention herein of any publication is not an admission that the publication serves as prior art with respect to any of the claims presented herein. Headers are provided for organizational purposes and are not meant to be limiting.

We claim:

1. A pharmaceutical dosage form comprising:
   a drug-containing solid having an outer surface and an internal three dimensional structural framework of one or more orderly arranged structural elements, said framework being contiguous with and terminating at said outer surface;
   said structural elements comprising particles, fibers, or sheets having segments spaced apart from adjoining segments, thereby defining free spaces, wherein a plurality of adjacent free spaces combine to define one or more interconnected free spaces forming an open pore network that extends over a length at least half the thickness of the drug-containing solid;
   said structural elements further comprising dissolved molecules or dispersed nanometer-scale aggregates of at least one sparingly-soluble active ingredient in an excipient matrix; wherein
   said excipient matrix comprises at least a water-soluble polymer carrier to carry the dissolved sparingly-soluble drug molecules and/or dispersed sparingly-soluble drug aggregates, and at least an amphiphilic polymer; whereby
   upon immersion in a physiological fluid, said open pore network enables wetting of the structural framework, so that the fluid interdiffuses with the framework, and the amphiphilic polymer self-assembles as micelles, thereby enhancing drug solubility.

2. The dosage form of claim 1, wherein one or more free spaces are filled with a gas.

3. The dosage form of claim 1, wherein free spaces are interconnected forming an open pore network that extends over a length at least equal to the thickness of the drug-containing solid.

4. The dosage form of claim 1, wherein the effective free spacing between segments across the one or more free spaces on average is in the range 1 µm-3 mm.

5. The dosage form of claim 1, wherein the free spacing between segments of the one or more structural elements is precisely controlled, so that the standard deviation of the free spacing across the three-dimensional structural framework is smaller than the average value.

6. The dosage form of claim 1, wherein the three dimensional structural framework forms a continuous structure.

7. The dosage form of claim 1, wherein at least one element or segment is bonded to another element or segment.

8. The dosage form of claim 7, wherein average contact width is no greater than 2 mm.

9. The dosage form of claim 1, wherein the one or more elements comprise an average thickness in the range 1 µm-2 mm.

10. The dosage form of claim 1, wherein the three dimensional structural framework comprises stacked layers (or plies) of particles, fibers, or sheets, or any combinations thereof.

11. The dosage form of claim 10, wherein one or more layers or plies are bonded to the layers or plies above or below said one or more layers.

12. The dosage form of claim 1, wherein the structural framework comprises a fibrous network having inter-fiber point contacts and fiber segments between adjacent contacts, and wherein the length of fiber segments between adjacent point contacts is precisely controlled, so that the standard deviation of the length of fiber segments between adjacent point contacts across the three-dimensional structural framework is smaller than the average value.

13. The dosage form of claim 1, wherein the three dimensional structural framework comprises criss-crossed stacked layers of fibers.

14. The dosage form of claim 1, wherein the weight fraction of a sparingly-soluble drug in the form of dissolved molecules or dispersed nanometer-scale aggregates in one or more elements with respect to the total weight of said sparingly-soluble drug in said one or more elements is greater than 0.6.

15. The dosage form of claim 1, wherein at least one water-soluble polymer carrier is absorptive of a physiological/body fluid, and wherein rate of penetration of the physiological/body fluid into an element or said absorptive excipient under physiological conditions is greater than the average fiber thickness divided by 3600 seconds.

16. The dosage form of claim 1, wherein at least one water-soluble polymer carrier comprises an amorphous polymer.

17. The dosage form of claim 1, wherein the least one water-soluble polymeric excipient comprises a solubility greater than 0.1 g/l in an aqueous physiological/body fluid under physiological conditions.

18. The dosage form of claim 1, wherein at least one water-soluble polymer carrier is selected from the group comprising hydroxypropyl methylcellulose, hydroxyethyl cellulose, polyvinyl alcohol, polyvinylpyrrolidone, hydroxypropyl methylcellulose acetate succinate, sodium alginate, hydroxypropyl cellulose, hydroxyethyl cellulose, methyl cellulose, hydroxypropyl methyl ether cellulose, starch, chitosan, pectin, polymethacrylates, or
   vinylpyrrolidone-vinyl acetate copolymer.

19. The dosage form of claim 1, wherein the molecular weight of at least one water-soluble polymer carrier is between 2 kg/mol and 700 kg/mol.

20. The dosage form of claim 1, wherein the weight fraction of water-soluble polymer carrier in an element with respect to the total weight of said element is greater than 0.15.

21. The dosage form of claim 1, wherein at least one amphiphilic polymer self-assembles in aqueous solutions to form regions of heterogeneous degree of hydrophobicity or hydrophilicity.

22. The dosage form of claim 1, wherein the amphiphilic polymer self-assembles as micelles in aqueous solutions, and wherein the critical micelle concentration is smaller than 1 mg/ml.

23. The dosage form of claim 1, wherein the molecular weight of at least one amphiphilic polymer is smaller than 500 kg/mol.

24. The dosage form of claim 1, wherein a slope, $\alpha$, of the drug solubility versus concentration of amphiphilic polymer in physiological/body fluid under physiological conditions is greater than 0.001.

25. The dosage form of claim 1, wherein a slope, $\alpha$, of the drug solubility versus concentration of amphiphilic polymer in physiological/body fluid under physiological conditions is greater than $0.05 \times c_0$, 0.05 times the drug solubility in said aqueous solution without excipient.

26. The dosage form of claim 1, wherein at least one amphiphilic polymer is selected from the group comprising polyoxyl stearate, polyethylene glycol methyl ether-blockpolylactide-co-glycolide, polyethylene glycol-polylactic acid (PEG-PLA) copolymer, poloxamer, lauroyl macrogol-32 glycerides, polyamidoamine.

27. The dosage form of claim 1, wherein the weight of amphiphilic polymer in at least one element divided by the weight of said element is between 0.05 and 0.7.

28. The dosage form of claim 1, wherein the amphiphilic polymer is dissolved as molecules or dispersed as nanometer-scale aggregates in a water-soluble polymer carrier.

29. The dosage form of claim 1, wherein the concentration of amphiphilic polymer is uniform across a region of an element comprising a composition of a sparingly-soluble drug and a water-soluble polymer carrier.

30. The dosage form of claim 1, wherein at least a sparingly-soluble drug, at least a water-soluble polymer carrier, and at least an amphiphilic excipient are blended through the body of one or more elements.

31. The dosage form of claim 1, wherein upon immersion in a physiological/body fluid the drug-containing solid transitions to a viscous medium, thereby expanding in all dimensions.

32. The dosage form of claim 1, wherein the drug-containing solid dissolves or disintegrates during or after transitioning to a viscous medium.

33. The dosage form of claim 1, wherein a sparingly-soluble drug supersaturates in a physiological/body fluid upon immersion of the dosage form in said fluid under physiological conditions, where the mass of said sparingly-soluble drug in the dosage form is greater than the product of solubility and fluid volume.

34. A pharmaceutical dosage form comprising:
a drug-containing solid having an outer surface and an internal three dimensional structural framework comprising a plurality of criss-crossed stacked layers of one or more fibrous structural elements, said framework contiguous with and terminating at said outer surface;
said fibrous structural elements further having segments spaced apart from like segments of adjoining elements, thereby defining free spaces, wherein a plurality of adjacent free spaces of successive layers combine to define one or more interconnected free spaces forming an open pore network;
said fibrous structural elements further comprising at least one sparingly-soluble active ingredient dissolved as molecules or dispersed as nanometer-scale aggregates in an excipient matrix;
said excipient matrix comprising least a water-soluble polymer carrier to carry the dissolved sparingly-soluble drug molecules and/or dispersed sparingly-soluble drug aggregates, and at least an amphiphilic polymer;
said amphiphilic polymer comprising dissolved molecules or dispersed particles of size no greater than 50 μm in said water-soluble polymer carrier, and having a weight fraction between 0.05 and 0.7 in at least an element;
whereby
upon immersion in a physiological fluid, said open pore network enables wetting of the structural framework, so that the fluid interdiffuses with the framework, and the amphiphilic polymer self-assembles as micelles, thereby enhancing drug solubility.

* * * * *